US005952490A

United States Patent [19]
Hanecak et al.

[11] Patent Number: 5,952,490
[45] Date of Patent: *Sep. 14, 1999

[54] OLIGONUCLEOTIDES HAVING A CONSERVED G4 CORE SEQUENCE

[75] Inventors: Ronnie C. Hanecak, San Clemente; Kevin P. Anderson; C. Frank Bennett, both of Carlsbad; Ming-Yi Chiang, Laguna Hills; Vickie L. Brown-Driver, San Diego; David J. Ecker, Leucadia; Timothy A. Vickers, Oceanside; Jacqueline R. Wyatt, Carlsbad, all of Calif.; Jean Louis Imbach, Montpellier, France

[73] Assignee: Isis Pharmaceuticals, Inc., Carlsbad, Calif.

[ * ] Notice: This patent is subject to a terminal disclaimer.

[21] Appl. No.: 08/403,888

[22] PCT Filed: Sep. 29, 1993

[86] PCT No.: PCT/US93/09297

§ 371 Date: Jun. 12, 1995

§ 102(e) Date: Jun. 12, 1995

[87] PCT Pub. No.: WO94/08053

PCT Pub. Date: Apr. 14, 1994

Related U.S. Application Data

[60] Substitute for application No. PCT/US93/09297, Sep. 29, 1993, which is a continuation-in-part of application No. 07/954,185, Sep. 29, 1992, abandoned.

[51] Int. Cl.$^6$ .................................................. C07H 21/04
[52] U.S. Cl. ........................................ 536/24.5; 536/25.5
[58] Field of Search ............................... 435/69.1, 172.1, 435/172.3, 320.1; 514/44; 536/23.1, 24.5, 25.5

[56] References Cited

U.S. PATENT DOCUMENTS

| | | | |
|---|---|---|---|
| 5,034,506 | 7/1991 | Summerton et al. | 528/391 |
| 5,514,577 | 5/1996 | Draper et al. | 435/238 |

FOREIGN PATENT DOCUMENTS

| | | |
|---|---|---|
| WO 91/16901 | 11/1991 | WIPO . |
| WO 91/16902 | 11/1991 | WIPO . |
| WO 91/18004 | 11/1991 | WIPO . |
| WO 92/03454 | 3/1992 | WIPO . |
| WO 93/18187 | 9/1993 | WIPO . |
| WO 93/23572 | 11/1993 | WIPO . |
| WO 94/07367 | 4/1994 | WIPO . |

OTHER PUBLICATIONS

Giovannangeli, et al., *Proc. Natl. Acad. Sci. USA*, 1992, 89, 8631–8635.
McShan, et al., *J. Biol. Chem.*, 1992, 267, 5712–5721.
Zahler, et al., *Nature*, 1991, 350, 718–720.
Agrawal, S., et al., "Oligodeoxynucleoside Phosphoramidates and Phosphorothioates as Inhibitors of Human Immunodeficiency Virus", *PNAS USA* 1988, 85, 7079–7083.
Agrawal, et al., "Inhibition of Human Immunodeficiency Virus in Early Infected and Chronically Infected Cells by Antisense oligodeoxynucleotides and their Phosphorothioate Analogues", *PNAS USA* 1989, 86, 7790–7794.
Bartlett, G., "Phosphorus assay in column chromatography", *J. Biol. Chem.*, 1959, 234(3), 466–468.
Bomalaski, J. et al., "Human extracellular recombinant phospholipase $A_2$ induces an inflammatory response in rabbit joints", *J. of Immunology* 1991, 146, 3904–3910.
Buck, H. et al., "Phosphate–methylayed DNA aimed at HIV–1 RNA loops and integrated DNA inhibits viral infectivity", *Science* 1990, 248, 208–212.
Counter, C. et al., "Telomere Shortening Associated with Chromosome Instability is Arrested in Immortal Cells Which Express Telomerase Activity", *The EMBO J.* 1992, 11(5), 1921–1929.
Crowl et al., "Induction of Phospholipase $A_2$ Gene Expression in Human Hepatoma Cells by Mediators of the Acute Phase Response", *J. Biol. Chem.* 1991, 266, 2647–2651.
Davidson et al., "Inhibition of Phospholipase $A_2$ by Lipocortins and Calpactins", *J. Biol. Chem.* 1987, 262, 1698–1705.
Farr et al., "Functional Reintroduction of Human Telomeres into Mammalian Cells", *PNAS USA* 1992, 88, 7006–7010.
Gattaz, et al., "Increased Serum Phospholipase $A_2$ Activity in Schizophrenia: A Replication Study", *Biol. Psychiatry* 1990, 28, 495–501.
Gilman, S.C. and Chang, J., "Characterization of Interleukin 1 Induced Rabbit Chondrocyte Phospholipase $A_2$", *J. Rheumatol.* 1990, 17, 1392–1396.
Gilman, et al., "Interleukin–1 Activates Phospholipase $A_2$ in Human Synovial Cells, Arthritis and Rheumatism", *Arthritis and Rheumatism* 1988, 31, 126–130.
Goodchild, et al., "Inhibition of Human Immunodeficiency Virus Replication By Antisense Oligodeoxynucleotides", *PNAS USA* 1988, 85, 5507–5511.
Greider, C., "Telomeres", *Current Opinion in Cell Biology* 1991, 3, 444–451.
Harley, C. et al., "Telomeres Shorten During Ageing of Human Fibroblasts", *Nature* 1990, 345, 458–460.
Harley, C.B., *Meth. Molec. Biol.* 1990, 5, 25–32.
Hastie, N.D. et al., "Telomere Reduction in Human Colorectal Carcinoma and with Ageing", *Nature* 1990, 346, 866–868.

(List continued on next page.)

*Primary Examiner*—David Guzo
*Attorney, Agent, or Firm*—Woodcock Washburn Kurtz Mackiewicz & Norris, LLP

[57] ABSTRACT

Modified oligonucleotides having a conserved $G_4$ sequence and a sufficient number of flanking nucleotides to significantly inhibit the activity of a virus such as HSV-1 or phospholipase $A_2$ or to modulate the telomere length of a chromosome are provided. $G_4$ quartet oligonucleotide structures are also provided. Methods of prophylaxis, diagnosis and therapeutics for viral-associated diseases and diseases associated with elevated levels of phospholipase $A_2$ are also provided. Methods of modulating telomere length of a chromosome are also provided; modulation of telomere length is believed to plat a role in the aging process of a cell and in control of malignant cell growth.

27 Claims, 16 Drawing Sheets

OTHER PUBLICATIONS

Hulkower, K.I. et al., "Interleukin –1β stimulates cytosolic phospholipase $A_2$ in rheumatoid synovial fibroblasts", *Biochemical and Biophysical Research Communications* 1992, 184(2), 712–718.

Kabanov et al., "A New Class of Antivirals: Antisense Oligonucleotides Combined with a Hydrophobic Substituent Effectively Inhibit Influenza Virus Reproduction and Synthesis of Virus–Specific Proteins in MDCK Cells", *FEBS Letters* 1990, 259, 327–330.

Kramer, I.M. et al., "1–0–Hexadecyl–2–O–methylglycerol, a novel inhibitor of protein kinase C, inhibits the respiratory burst in human neutrophils", *J. of Biological Chemistry* 1989, 264(10), 5876–5884.

Leiter et al., "Inhibition of influenza virus replication by phosphorothioate oligodexoynucleotides", *PNAS USA* 1990, 87, 3430–3434.

Letsinger et al., "Cholesteryl–conjugated oligonucleotides: Synthesis, properties, and activity as inhibitors of replication of human immunodeficiency virus in cell culture", *PNAS USA* 1989, 86, 6553–6556.

Matsukura, M. et al., "Phosphorothioate analogs of oligodeoxynucleotides: Inhibitors of replication and cytopathic effects of human immunodeficiency virus", *Proc.Natl.Acad. .Sci. USA* 1987, 84, 7706–7710.

Mori, K. et al., "Phosphoroselenoate oligodeoxynucleotides: synthesis, physico–chemical characterization, anti–sense inhibitory properties, and anti–HIV activity", *Nucleic Acids Research* 1989, 17, 8207–8219.

Nakano, T. et al., "Group II Phospholipase $A_2$ mRNA Synthesis is Stimulated by Two Distinct Mechanisms in Rat Vascular Smooth Muscle Cells", *FEBS Letters* 1990, 261(1), 171–174.

Nielsen, P.E., et al., "Sequence–Selective Recognition of DNA by Strand Displacement with a Thymine–Substituted Polyamide", *Science* 1991, 254, 1497–1500.

Oka, S. and Arita, H., "Inflammoratory factors stimulate expression of group II phospholipase $A_2$ in rat cultured astrocytes", *J. of Biological Chemistry* 1991, 266(15), 9956–9960.

Olaison, G. et al., "Increased Phsopholipase $A_2$ Activity of Ileal Mucosa in Crohn's Disease", *Digestion* 1988, 41, 136–141.

Pruzanski et al., "Serum phospholipase $A_2$ correlates with disease activity in rheumatoid arthritis", *J. Rheumatol.* 1988, 15, 1351–1355.

Pruzanski and Vadas, "Secretary synovial fluid phospholipase $A_2$ and its role in the pathogenesis of inflammation in arthritis", *J. Rheumatol.* 1988, 15(11), 1601–1603.

Pruzanski et al., "Inflammatory effect of intradermal administration of soluble phospholipase $A_2$ in rabbits", *J. Invest. Dermatol.* 1986, 86, 380–383.

Sarin, P. et al., "Inhibition of Acquired Immunodeficiency Syndrome Virus by Oligodeoxynucleoside Methylphosphonates", *PNAS USA* 1988, 85, 7448–7451.

Schalwijk, C. et al., "Interleukin–1β, Tumor Necrosis Factor and Forskolin Stimulate the Synthesis and Secretion of Gorup II Phospholipase $A_2$ in Rat Mesangial Cells", *Biochem. and Biophys. Res. Commun.* 1991, 174(1), 268–275.

Schalwijk, C. et al., "Interleukin–1β–and Forskolin–induced Synthesis and Secretion of Gorup II Phospholipase $A_2$ and Prostaglandin $E_2$ in Rat Mesangial Cells is Prevented by Transforming Growth Factor–β2", *The J. of Biol. Chem.* 1992, 267(13), 8846–8851.

Shibahara et al., "Inhibition of Human Immunodeficiency Virus (HIV-1) Replication by Synthetic Oligo–RNA Derivatives", *Nucleic Acids Research* 1989, 17, 239–252.

Shida, S. et al., "Self–Association of Telomeric Short Oligodeoxynucleotides Containing a dG Cluster", *Chem. Pharm. Bull.* 1991, 39(9), 2207–2211.

Stevenson et al., "Inhibition of Human Immunodeficiency Virus Type 1–mediated Cytopathic Effects by Poly(L–lysine)–conjugated Synthetic Antisense Oligodeoxyribonucleotides", *J. Gen. Virol.* 1989, 70, 2673–2682.

Vadas et al., "Pathogenesis of hypotension in septic shock: Correlation of Circulating phospholipase $A_2$ levels with circulatory collapse", *Critical Care* .

Vadas et al., "The Proinflammatory Effect of Intra–articular Injection of Soluble Human and Venom Phospholipase $A_2$", *American Journal of Pathology* 1989, 134(4), 807–811.

Zaia, J.A. et al., "Inhibition of human immunodeficiency virus by using an oligonucleoside mehtylphosphonate targeted to the tat–3 gene", *J. of Virology* 1988, 62(10), 3914–3917.

Zamecnik, P.C. et al., "Inhibition of replication and expression of human T–cell lymphotropic virus type III in cultured cells by exogenous synthetic oligonucleotides complementary to viral RNA", *Proc. Natl. Acad. Sci. USA* 1986, 83, 4143–4146.

Zerial, A. et al., "Selective inhibition of the cytopathic effect of type A influenza viruses by oligodeoxynucleotides convalently linked to an intercalating agents", *Nucleic Acids Research* 1987, 15(23), 9909–9919.

Stein et al., Cancer Res., vol. 48, pp. 2659–2668, May 15, 1988.

Gura, Science, vol. 270, Oct. 27, 1995, pp. 575–577.

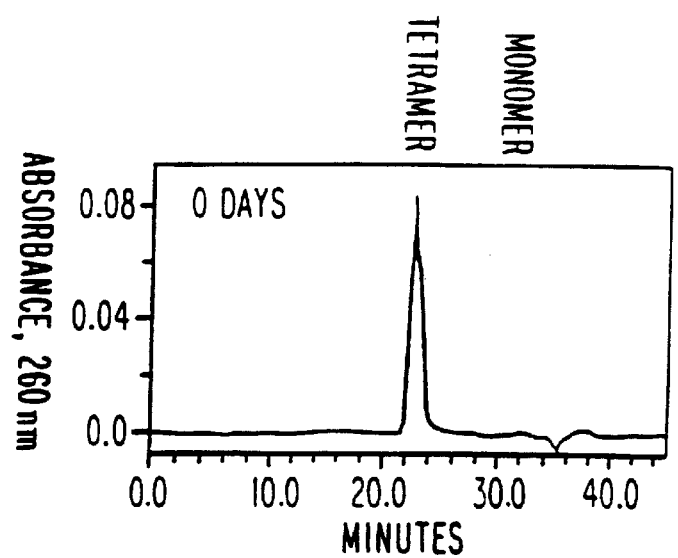
_Fig. 13a_
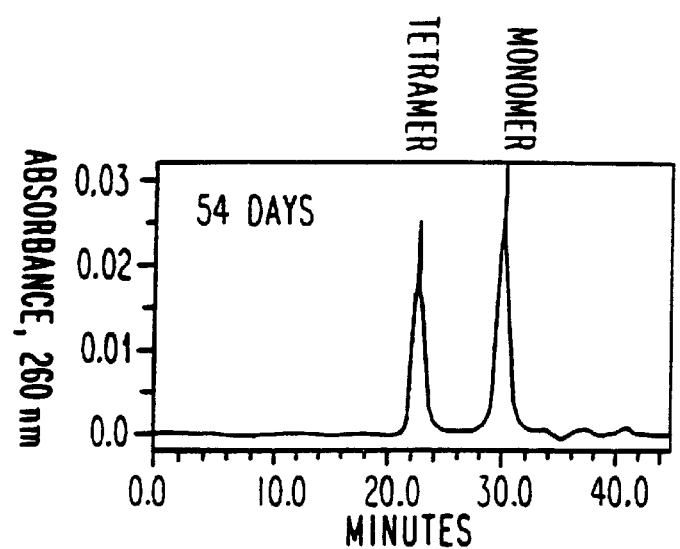
_Fig. 13b_
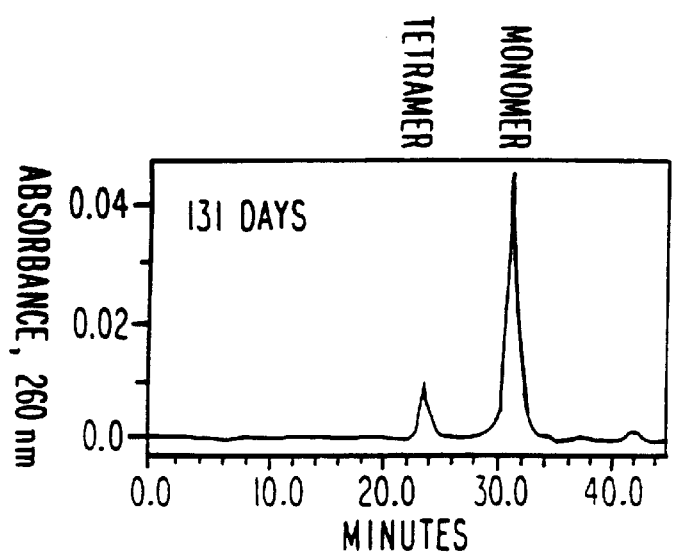
_Fig. 13c_

OLIGONUCLEOTIDES HAVING A CONSERVED G4 CORE SEQUENCE

This application is a 371 of PCT/US93/09297, filed Sep. 29, 1993, which is a continuation in part of Ser. No. 07/954,185, filed Sep. 29, 1992, now abandoned.

FIELD OF THE INVENTION

This invention relates to the design and synthesis of oligonucleotides which can be used to inhibit the activity of viruses in vivo or in vitro and to treat viral-associated disease. These compounds can be used either prophylactically or therapeutically for diseases associated with viruses such as HIV, HSV, HCMV and influenza. Oligonucleotides capable of inhibiting phospholipase $A_2$ enzyme activity are also provided which may be useful for the treatment of inflammatory disorders, as well as neurological conditions.

Oligonucleotides designed for the treatment of cancer and to retard aging are also contemplated by this invention.

BACKGROUND OF THE INVENTION

Antivirals

There have been many approaches for inhibiting the activity of viruses such as the human immunodeficiency virus (HIV), herpes simplex virus (HSV), human cytomegalovirus (HCMV) and influenza. Such prior art methods include nucleoside analogs (e.g., HSV) and antisense oligonucleotide therapies (e.g., HIV, influenza).

Prior attempts to inhibit HIV by various approaches have been made by a number of researchers. For example, Zamecnik and coworkers have used phosphodiester antisense oligonucleotides targeted to the reverse transcriptase primer site and to splice donor/acceptor sites, P. C. Zamecnik, J. Goodchild, Y. Taguchi, P. S. Sarin, *Proc. Natl. Acad. Sci. USA* 1986, 83, 4143. Goodchild and coworkers have made phosphodiester antisense compounds targeted to the initiation sites for translation, the cap site, the polyadenylation signal, the 5' repeat region, primer binding site, splice sites and a site between the gag and pol genes. J. Goodchild, S. Agrawal, M. P. Civeira, P. S. Sarin, D. Sun, P. C. Zamecnik, *Proc. Natl. Acad. Sci. U.S.A.* 1988, 85, 5507; U.S. Pat. No. 4,806,463. Agrawal and coworkers have used chemically modified antisense oligonucleotide analogs targeted to the cap and splice donor/acceptor sites. S. Agrawal, J. Goodchild, M. P. Civeira, A. H. Thornton, P. S. Sarin, P. C. Zamecnik, *Proc. Nat'l. Acad. Sci. USA* 1988, 85, 7079. Agrawal and coworkers have used antisense oligonucleotide analogs targeted to the splice donor/acceptor site inhibit HIV infection in early infected and chronically infected cells. S. Agrawal, T. Ikeuchi, D. Sun, P. S. Sarin, A. Konopka, J. Maizel, *Proc. Natl. Acad. Sci. U.S.A.* 1989, 86, 7790.

Sarin and coworkers have also used chemically modified antisense oligonucleotide analogs targeted to the HIV cap and splice donor/acceptor sites. P. S. Sarin, S. Agrawal, M. P. Civeira, J. Goodchild, T. Ikeuchi, P. C. Zamecnik, *Proc. Natl. Acad. Sci. U.S.A.* 1988, 85, 7448. Zaia and coworkers have also used an antisense oligonucleotide analog targeted to a splice acceptor site to inhibit HIV. J. A. Zaia, J. J. Rossi, G. J. Murakawa, P. A. Spallone, D. A. Stephens, B. E. Kaplan, *J. Virol.* 1988, 62, 3914. Matsukura and coworkers have synthesized antisense oligonucleotide analogs targeted to the initiation of translation of the HIV rev gene mRNA. M. Matsukura, K. Shinozuka, G. Zon, *Proc. Natl. Acad. Sci. USA* 1987, 84, 7706; R. L. Letsinger, G. R. Zhang, D. K. Sun, T. Ikeuchi, P. S. Sarin, *Proc. Natl. Acad. Sci. U.S.A.* 1989, 86, 6553. Mori and coworkers have used a different antisense oligonucleotide analog targeted to the same region as Matsukura. K. Mori, C. Boiziau, C. Cazenave, *Nucleic Acids Res.* 1989, 17, 8207. Shibahara and coworkers have used antisense oligonucleotide analogs targeted to a splice acceptor site as well as the reverse transcriptase primer binding site.

S. Shibahara, S. Mukai, H. Morisawa, H. Nakashima, S. Kobayashi, N. Yamamoto, *Nucl. Acids Res.* 1989, 17, 239. Letsinger and coworkers have synthesized and tested a oligonucleotide analogs with conjugated cholesterol targeted to a splice site. K. Mori, C. Boiziau, C. Cazenave, *Nucleic Acids Res.* 1989, 17, 8207. Stevenson and Iversen have conjugated polylysine to antisense oligonucleotide analogs targeted to the splice donor and the 5'-end of the first exon of the HIV tat gene. M. Stevenson, P. L. Iversen, *J. Gen. Virol.* 1989, 70, 2673. Buck and coworkers have described the use of phosphate-methylated DNA oligonucleotides targeted to HIV mRNA and DNA. H. M. Buck, L. H. Koole, M. H. P. van Gendersen, L. Smith, J. L. M. C. Green, S. Jurriaans and J. Goudsmit, *Science* 1990, 248, 208–212.

These prior attempts at inhibiting HIV activity have largely focused on the nature of the chemical modification used in the oligonucleotide analog. Although each of the above publications have reported some degree of success in inhibiting some function of the virus, a general therapeutic scheme to target HIV and other viruses has not been found. Accordingly, there has been and continues to be a long-felt need for the design of compositions which are capable of effective, therapeutic use.

Currently, nucleoside analogs are the preferred therapeutic agents for herpes (HSV) infections. A number of pyrimidine deoxyribonucleoside compounds have a specific affinity for the virus-encoded thymidine (dCyd) kinase enzyme. The specificity of action of these compounds confines the phosphorylation and antiviral activity of these compounds to virus-infected cells. A number of drugs from this class, e.g., 5-iodo-dUrd (IDU), 5-trifluoro-methyl-dUrd (FMAU), 5-ethyl-dUrd (EDU), (E)-5-(2-bromovinyl)-dUrd (BVDU), 5-iodo-dCyd (IDC), and 5-trifluoromethyl-dUrd (TFT), are either in clinical use or likely to become available for clinical use in the near future. IDU is a moderately effective topical antiviral agent when applied to HSV gingivostomatitis and ocular stromal keratitis; however, its use in controlled clinical studies of HSV encephalitis revealed a high toxicity associated with IDU treatment. Although the antiviral specificity of 5-arabinofuranosyl cytosine (Ara-C) was initially promising, is clinical history has paralleled that of IDU. The clinical appearance of HSV strains which are deficient in their ability to synthesize the viral thymidine kinase has generated further concern over the future efficacy of this class of compounds.

The utility of a number of viral targets has been defined for anti-HSV compound development. Studies with thiosemicarbazone compounds have demonstrated that inhibition of the viral ribonucleotide reductase enzyme is an effective means of inhibiting replication of HSV in vitro. Further, a number of purine nucleosides which interfere with viral DNA replication have been approved for treatment of human HSV infections. 9-(β-D-arabinofuranosyl) adenine (Ara-A) has been used for treatment of HSV-1 keratitis, HSV-1 encephalitis and neonatal herpes infections. Reports of clinical efficacy are contradictory and a major disadvantage for practical use is the extremely poor solubility of Ara-A in water. 9-(2-hydroxyethoxymethyl) guanine (Acyclovir, ACV) is of major interest. In humans, ACV has been used successfully in the therapy of localized and disseminated HSV infections. However there appear to be both the existence of drug-resistant viral mutants and negative results in double-blind studies of HSV-1 treatment with ACV. ACV, like Ara-A, is poorly soluble in water (0.2%) and this physical characteristic limits the application forms for ACV. The practical application of purine nucleoside analogs in an extended clinical situation suffers from their inherently efficient catabolism, which not only lowers the biological activity of the drug but also may result in the formation of toxic catabolites.

The effective anti-HSV compounds currently in use or clinical testing are nucleoside analogs. The efficacy of these compounds is diminished by their inherently poor solubility in aqueous solutions, rapid intracellular catabolism and high cellular toxicities. An additional caveat to the long-term use of any given nucleoside analogue is the recent detection of clinical isolates of HSV which are resistant to inhibition by nucleoside compounds which were being administered in clinical trials. Antiviral oligonucleotides offer the potential of better compound solubilities, lower cellular toxicities and less sensitivity to nucleotide point mutations in the target gene than those typical of the nucleoside analogs.

Effective therapy for cytomegalovirus (CMV) has not yet been developed despite studies on a number of antivirals. Interferon, transfer factor, adenine arabinoside (Ara-A), acycloguanosine (Acyclovir, ACV) and certain combinations of these drugs have been ineffective in controlling CMV infection. Based on preclinical and clinical data, foscarnet (PFA) and ganciclovir (DHPG) show limited potential as antiviral agents. PFA treatment has resulted in the resolution of CMV retinitis in five AIDS patients. DHPG studies have shown efficacy against CMV retinitis or colitis. DHPG seems to be well tolerated by treated individuals, but the appearance of a reversible neutropenia, the emergence of resistant strains of CMV upon long-term administration, and the lack of efficacy against CMV pneumonitis limit the long term applications of this compound. The development of more effective and less-toxic therapeutic compounds and methods is needed for both acute and chronic use.

Classical therapeutics has generally focused upon interactions with proteins in efforts to moderate their disease-causing or disease-potentiating functions. Such therapeutic approaches have failed for cytomegalovirus infections. Therefore, there is an unmet need for effective compositions capable of inhibiting cytomegalovirus activity.

There are several drugs available which have some activity against the influenza virus prophylactically. None, however, are effective against influenza type B. Moreover, they are generally of very limited use therapeutically and have not been widely used in treating the disease after the onset of symptoms. Accordingly, there is a world-wide need for improved therapeutic agents for the treatment of influenza virus infections. attempts at the inhibition of influenza virus using antisense oligonucleotides have been reported. Leiter and coworkers have targeted phosphodiester and phosphorothioate oligonucleotides to influenza A and influenza C viruses. Leiter, J., Agrawal, S., Palese, P. & Zamecnik, P. C., *Proc. Natl. Acad. Sci.* USA; 1990, 87, 3430–3434. These workers targeted the polymerase PB1 gene and mRNA in the vRNA 3' region and mRNA 5' region, respectively. Sequence-specific inhibition of influenza A was not observed although some specific inhibition of influenza C was noted.

Zerial and co-workers have reported inhibition of influenza A virus by oligonucleotides coincidentally linked to an intercalating agent. Zerial, A., Thuong, N. T. & Helene, C., *Nucleic Acids Res.* 1987, 57, 9909–9919. Zerial et al. targeted the 3' terminal sequence of 8 vRNA segments. Their oligonucleotide analog was reported to inhibit the cytopathic effects of the virus in cell culture.

Kabanov and co-workers have synthesized an oligonucleotide complementary to the loop-forming site of RNA encoding RNA polymerase 3. Kabanov, A. V., Vinogradov, S. V., Ovcharenko, A. V., Krivonos, A. V., Melik-Nubarov, N. S., Kiselev, V. I., Severin, E. S., *FEB;* 1990, 259, 327–330. Their oligonucleotide was conjugated to a undecyl residue at the 5' terminal phosphate group. They found that their oligonucleotide inhibited influenza A virus infection in MDCK cells.

Although each of the foregoing workers reported some degree of success in inhibiting some function of an influenza virus, a general therapeutic scheme to target influenza viruses has not been found. Moreover, improved efficacy is required in influenza virus therapeutics. Accordingly, there has been and continues to be a long-felt need for the design of oligonucleotides which are capable of effective therapeutic use.

Phospholipase $A_2$ Enzyme Activity

Phospholipase $A_2$ is a family of lipolytic enzymes which hydrolyze membrane phospholipids. Phospholipase $A_2$ catalyzes the hydrolysis of the sn-2 bond of phospholipids resulting in the Production of free fatty acid and lysophospholipids. Several types of phospholipase $A_2$ enzymes have been cloned and sequenced from human cells. However, there is biochemical evidence that additional forms of phospholipase $A_2$ exists. Mammalian secreted phospholipase $A_2$ shares strong sequence similarities with phospholipase $A_2$ isolated from the venom of poisonous snakes. Secreted forms of phospholipase $A_2$ have been grouped into two categories based upon the position of cysteine residues in the protein. Type I phospholipase $A_2$ includes enzymes isolated from the venoms of Elapidae (cobras), Hydrophidae (sea snakes) and the mammalian pancreatic enzyme. Type II phospholipase $A_2$ includes enzymes isolated from the venoms of Crotalidae (rattlesnakes and pit vipers), Viperidae (old world vipers) and an enzyme secreted from platelets and other mammalian cells.

Much interest has been generated in mammalian type II phospholipase $A_2$, in that elevated concentrations of the enzyme have been detected in a variety of inflammatory disorders including rheumatoid arthritis, inflammatory bowel disease, and septic shock as well as neurological conditions such as schizophrenia, Pruzanski, W., Keystone, E. C., Sternby, B., Bombardier, C., Snow, K. M., and Vadas, P. J. *Rheumatol.* 1988, 15, 1351; Pruzanski and Vadas *J. Rheumatol.* 1988, 15, 11; Oliason, G., Sjodahl, R., and Tagesson, C. *Digestion* 1988, 41, 136; Vadas et al. *Crit. Care Med.* 1988, 16, 1; Gattaz, W. F., Hubner, C. v. K., Nevalainen, T. J., Thuren, T., and Kinnunen, P. K. J. Biol. *Psychiatry* 1990, 28, 495. It has been recently demonstrated that secretion of type II phospholipase $A_2$ is induced by a variety of proinflammatory cytokines such as interleukin-1, interleukin 6, tumor necrosis factor, interferon -γ, and bacterial lipopolysaccharide. Hulkower, K., Hope, W. C., Chen, T., Anderson, C. M., Coffey, J. W., and Morgan, D. W., *Biochem. Biophys.Res. Comm.* 1992, 184, 712; Crowl, R. M., Stoller, T. J., Conroy, R. R. and Stoner, C. R., *J. Biol. Chem.* 1991, 266, 2647; Schalkwijk, C., Pfeilschafter, J., Marki, F., and van den Bosch, J., *Biochem. Biophys. Res. Comm.* 1991, 174, 268; Gilman, S. C. and Chang, J., *J. Rheumatol.* 1990, 17, 1392; Oka, S. and Arita, H., *J.Biol. Chem.* 1991, 266, 9956. Anti-inflammatory agents such as transforming growth factor-β and glucocorticoids have been found to inhibit secretion of type II phospholipase $A_2$. Oka, S. and Arita, H., *J. Biol. Chem.* 1991, 266, 9956; Schalkwijk, C., Pfeilschifter, J., Marki, F. and van den Bosch, H., *J. Biol. Chem.* 1992, 267, 8846. Type II phospholipase $A_2$ has been demonstrated to be secreted from a variety of cell types including platelets, chrondrocytes, synoviocytes, vascular smooth muscle cells, renal mesangial cells, and keratinocytes. Kramer, R. M., Hession, C., Johansen, B., Hayes, G., McGray, P., Chow, E. P., Tizard, R. and Pepinsky, R. B., *J. Biol. Chem.* 1989, 264, 5768; Gilman, S. C. and Chang, J., *J. Rheumatol.* 1990, 17, 1392; Gilman, S. C., Chang, J., Zeigler, P. R., Uhl, J. and Mochan, E., *Arthritis and Rheumatol.* 1988, 31, 126; Nakano, T., Ohara, O., Teraoka, H. and Arita, H., *FEBS Lett.,* 1990, 261, 171; Schalkwijk, C., Pfeilschifter, J., Marki, F. and van den Bosch, H. *Biochem. Biophys. Res. Comm.* 1991, 174, 268.

A role of type II phospholipase $A_2$ in promoting some of the pathophysiology observed in chronic inflammatory disorders was suggested because direct injection of type II phospholipase $A_2$ produced profound inflammatory reactions when injected intradermally or in the articular space in rabbits, Pruzanski, W., Vadas, P., Fornasier, V., *J. Invest. Dermatol.* 1986, 86, 380–383; Bomalaski, J. S., Lawton, P., and Browning, J. L., *J. Immunol.* 1991, 146, 3904; Vadas, P., Pruzanski, W., Kim, J. and Fornasier, V., *Am. J. Pathol.* 1989, 134, 807. Denaturation of the protein prior to injection was found to block the proinflammatory activity.

Because of these findings, there is interest in identifying potent and selective inhibitors of type II phospholipase $A_2$. To date, efforts at identifying non toxic and selective inhibitors of type II phospholipase $A_2$ have met with little success. Therefore, there is an unmet need to identify effective inhibitors of phospholipase $A_2$ activity.

Modulation of Telomere Length

It has been recognized that telomeres, long chains of repeated nucleotides located at the tip of each chromosome, play a role in the protection and organization of the chromosome. In human cells, the sequence TTAGGG is repeated hundreds to thousands of times at both ends of every chromosome, depending on cell type and age. Harley, C. B. et al., *Nature,* 1990, 345, 458–460; Hastie, N. D. et al., *Nature,* 1990, 346,866–868. Telomeres also appear to have a role in cell aging which has broad implications for the study of aging and cell immortality that is manifested by cancerous cells.

Researchers have determined that telomere length is reduced whenever a cell divides and it has been suggested that telomere length controls the number of divisions before a cell's innate lifespan is spent. Harley, C. B. et al., *Nature,* 1990, 345, 458–460; Hastie, N. D. et al., *Nature,* 1990, 346,866–868. For example, normal human cells divide between 70–100 times and appear to lose about 50 nucleotides of their telomeres with each division. Some researchers have suggested that there is a strong correlation between telomere length and the aging of the entire human being. Greider, C. W., *Curr. Opinion Cell Biol.,* 1991, 3, 444–451. Other studies have shown that telomeres undergo a dramatic transformation during the genesis and progression of cancer. Hastie, N. D. et al., *Nature* 1990, 346, 866–868. For example, it has been reported that when a cell becomes malignant, the telomeres become shortened with each cell division. Hastie, N. D. et al., *Nature* 1990, 346, 866–868. Experiments by Greider and Bacchetti and their colleagues have shown that at a very advanced and aggressive stage of tumor development, telomere shrinking may cease or even reverse. Counter, C. M. et al., *EMBO J.* 1992, 11, 1921–1929. It has been suggested, therefore, that telomere blockers may be useful for cancer therapy. In vitro studies have also shown that telomere length can be altered by electroporation of linearized vector containing human chromosome fragments into hybrid human-hamster cell lines. Chromosome fragments consisted of approximately 500 base pairs of the human telomeric repeat sequence TTAGGG and related variants such as TTGGGG, along with adjacent GC-rich repetitive sequences. Farr, C. et al., *Proc. Natl. Acad. Sci.* USA 1992, 88, 7006–7010. While this research suggests that telomere length affects cell division, no effective method for control of the aging process or cancer has been discovered. Therefore, there is an unmet need to identify effective modulators of telomere length.

Guanosine nucleotides, both as mononucleotides and in oligonucleotides or polynucleotides, are able to form arrays known as guanine quartets or G-quartets. For review, see Williamson, J. R., (1993) Curr. Opin. Struct. Biol. 3:357–362. G-quartets have been known for years, although interest has increased in the past several years because of their possible role in telomere structure and function. One analytical approach to this area is the study of structures formed by short oligonucleotides containing clusters of guanosines, such as GGGGTTTTGGGG SEQ ID NO:143 , GGGTTTTGGG SEQ ID NO:144, UGGGGU, GGGGGTTTTT SEQ ID NO:145, TTAGGG, TTGGGG and others reviewed by Williamson; TTGGGGTT described by Shida et al. (Shida, T., Yokoyama, K., Tamai, S., and J. Sekiguchi (1991) Chem. Pharm. Bull. 39:2207–2211), and others.

It has now been discovered that in addition to their natural role (in telomeres, for example, though there may be others), oligonucleotides which form G-quartets and oligonucleotides containing clusters of G's are useful for inhibiting viral gene expression and viral growth and for inhibiting $PLA_2$ enzyme activity, and may also be useful as modulators of telomere length. Chemical modification of the oligonucleotides for such use is desirable and, in some cases, necessary for maximum activity.

Oligonucleotides containing only G and T have been designed to form triple strands with purine-rich promotor elements to inhibit transcription. These triplex-forming oligonucleotides (TFOs), 28 to 54 nucleotides in length, have been used to inhibit expression of the oncogene c-erb B2/neu (WO 93/09788, Hogan). Amine-modified TFOs 31–38 nucleotides long have also been used to inhibit transcription of HIV. McShan, W. M. et al. (1992) *J. Biol. Chem.* 267:5712–5721.

OBJECTS OF THE INVENTION

It is an object of the invention to provide oligonucleotides capable of inhibiting the activity of a virus.

It is another object of the invention to provide methods of prophylaxis, diagnostics and therapeutics for viral-associated diseases such as HIV, HSV, HCMV and influenza.

It is a further object of the invention to provide oligonucleotides capable of inhibiting phospholipase $A_2$.

Yet another object of the invention is to provide methods of prophylaxis, diagnostics and therapeutics for the treatment of inflammatory disorders, as well as neurological conditions associated with elevated levels of phospholipase $A_2$.

It is another object of the invention to provide oligonucleotides for modulating telomere length on chromosomes.

It is another object of the invention to provide oligonucleotide complexes capable of inhibiting HIV.

These and other objects will become apparent to persons of ordinary skill in the art from a review of the instant specification and appended claims.

SUMMARY OF THE INVENTION

It has been discovered that oligonucleotides containing the sequence GGGG ($G_4$), denominated herein as a conserved $G_4$ core sequence, have antiviral activity against a number of viruses including but not limited to HIV, HSV, HCMV, and influenza virus. A sequence containing 4 guanines (G's) or 2 stretches of 3 G's has been found to be effective for significant antiviral activity. It has also been discovered that oligonucleotides containing a conserved $G_4$ core sequence or two stretches of 3 G's are effective inhibitors of phospholipase $A_2$ activity. It is also believed that such oligonucleotides could be useful for modulation of telomere length on chromosomes.

The formula for an active sequence is generally $(N_XG_4N_Y)_Q$ or $(G_{3-4}N_XG_{3-4})_Q$ wherein X and Y are 1–8, and Q is 1–4. The sequence $(N_XG_{3-4})_QN_X$ wherein X is 1–8 and Q is 1–6 has also been found to be useful in some embodiments of the invention.

BRIEF DESCRIPTION OF THE DRAWINGS

FIG. 13 (Parts a–c) is a line plot showing dissociation of ISIS 5320 tetramer monitored by size exclusion chromatography over a period of 1 to 131 days.

DETAILED DESCRIPTION OF THE INVENTION

Figure 1:
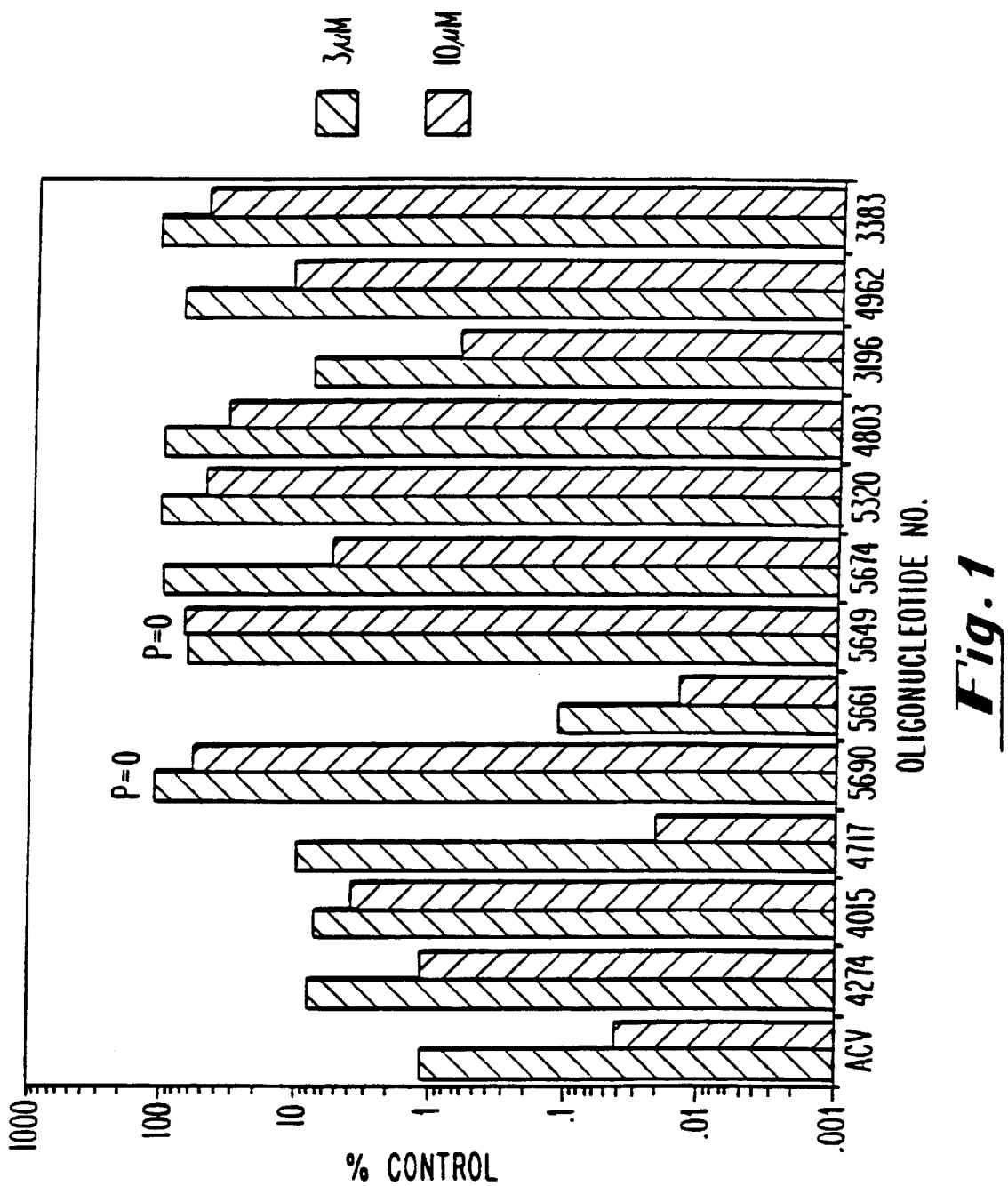
FIG. 1 is a graph showing anti-HSV activity of $G_4$ oligonucleotides as measured by virus yield assay. Cells were treated with oligonucleotide at dose of 3 $\mu$M or 1 $\mu$M. Viral titers are shown as a percentage of virus titer from untreated, infected cells. All oligonucleotides tested contain a phosphorothioate backbone except for those noted with a P=O.

It has been discovered that oligonucleotides containing the sequence GGGG ($G_{4'}$) where G is a guanine-containing nucleotide or analog, and denominated herein as a conserved $G_4$ sequence, have potent antiviral activity and can be effective inhibitors of phospholipase $A_2$ activity and modulators of telomere length on chromosomes. In the context of this invention, the term "oligonucleotide" refers to an oligomer or polymer of ribonucleic acid or deoxyribonucleic acid. This term includes oligomers consisting of naturally occurring bases, sugars and intersugar (backbone) linkages as well as oligomers having non-naturally occurring portions which function similarly. Such chemically modified or substituted oligonucleotides are often preferred over native forms because of properties such as, for example, enhanced cellular uptake and increased stability in the presence of nucleases.

Specific examples of some preferred oligonucleotides envisioned for this invention may contain modified intersugar linkages (backbones) such as phosphorothioates, phosphotriesters, methyl phosphonates, chain alkyl or cycloalkyl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Also preferred are oligonucleotides having morpholino backbone structures. Summerton, J. E. and Weller, D. D., U.S. Pat. No. 5,034,506. In other preferred embodiments, such as the protein-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, Science 1991, 254, 1497. Other preferred oligonucleotides may contain modified sugar moieties comprising one of the following at the 2' position: OH, SH, $SCH_3$, F, OCN, O($CH_2$)$_n$$NH_2$ or O($CH_2$)$_n$$CH_3$ where n is from 1 to about 10; $C_1$ to $C_{10}$ lower alkyl, substituted lower alkyl, alkaryl or aralkyl; Cl; Br; CN; $CF_3$; $OCF_3$; —O—, S—, or N-alkyl; —O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; fluorescein; a reporter group; an intercalator; a group for improving the pharmacokinetic properties of an oligonucleotide; or a group for improving the pharmacodynamic properties of an oligonucleotide and other substituents having similar properties. A fluorescein moiety may be added to the 5' end of the oligonucleotide. Oligonucleotides may also have sugar mimetics such as cyclobutyls in place of the pentofuranosyl group. Alpha (α) anomers instead of the standard beta (β) nucleotides may also be used. Modified bases such as 7-deaza-7-methyl guanosine may be used. A "universal" base such as inosine may also be substituted for A,C,G,T or U.

Chimeric oligonucleotides can also be employed; these molecules contain two or more chemically distinct regions, each comprising at least one nucleotide. These oligonucleotides typically contain a region of modified nucleotides that confer one or more beneficial properties (such as, for example, increased nuclease resistance, increased uptake into cells, increased binding affinity for the target molecule) and an unmodified region that retains the ability to direct RNase H cleavage.

The oligonucleotides in accordance with this invention preferably comprise from about 6 to about 27 nucleic acid base units. It is preferred that such oligonucleotides have from about 6 to 24 nucleic acid base units. As will be appreciated, a nucleic acid base unit is a base-sugar combination suitably bound to adjacent nucleic acid base unit through phosphodiester or other bonds.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed, however the actual synthesis of the oligonucleotides are well within the talents of the routineer. It is also well known to use similar techniques to prepare other oligonucleotides such as the phosphorothioates and alkylated derivatives.

Compounds with more than four G's in a row are active, but four in a row or two or more runs of three G's in a row have been found to be required for significant inhibitory activity. In the context of this invention, a significant level of inhibitory activity means at least 50% inhibition of activity as measured in an appropriate, standard assay. Such assays are well known to those skilled in the art. Although the conserved $G_4$ core sequence or $G_4$ pharmacophore is necessary, sequences flanking the $G_4$ core sequence have been found to play an important role in inhibitory activity because it has been found that activity can be modulated by substituting or deleting the surrounding sequences. In the context of this invention, the term "modulate" means increased or decreased.

The essential feature of the invention is a conserved $G_4$ core sequence and a sufficient number of additional flanking bases to significantly inhibit activity. It has also been discovered that analogs are tolerated in the backbone. For example, deoxy, phosphorothioate and 2'-O-Methyl analogs have been evaluated.

The formula for an active sequence is:

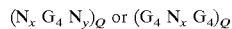

where G=a guanine-containing nucleotide or analog, N=any nucleotide, X=1–8, Y=1–8, and Q=1–4. In some embodiments of the present invention, the sequence $(N_X G_{3-4})_Q N_X$ wherein X is 1–8 and Q is 1–6 has been found to be active.

Antivirals

A series of oligonucleotides containing $G_4$ or 2 stretches of $G_3$ were tested for inhibition of HSV replication. Antiviral activity was determined by ELISA. The results are shown in Table 1. Activity is shown as E.C.$_{.50}$, which is the concentration of oligonucleotide which provides 50% inhibition of HSV replication relative to control infected cells. Oligonucleotides were generally tested at doses of 3 μM and lower.

TABLE I

Oligonucleotide inhibition of HSV replication

| ISIS NO | SEQUENCE | LENGTH | COMPOSITION | EC50 μm | SEQ ID NO |
|---|---|---|---|---|---|
| 1220 | CAC GAA AGG CAT GAC CGG GGC | 21 MER | P=S | 0.24, 0.16 | 1 |
| 4881 | GAA AGG CAT GAC CGG GGC | 18 MER | P=S | 0.7, 0.65 | 2 |
| 4874 | AGG CAT GAC CGG GGC | 15 MER | P=S | 1.1, 0.83 | 3 |
| 4873 | CAT GAC CGG GGC | 12 MER | P=S | 1.4, 1.0 | 4 |
| 5305 | CAC GAA AGG CAT GAC CGG G | 19 MER | P=S | >3.0 | 5 |
| 5301 | CAC GAA AGG CAT GAC CGG | 18 MER | P=S | >3.0 | 6 |
| 5302 | CAC GAA AGG CAT GAC | 15 MER | P=S | >3.0 | 7 |
| 4274 | CAT GGC GGG ACT ACG GGG GCC | 21 MER | P=S | 0.15, 0.15 | 8 |
| 4882 | CAT GGC GGG ACT ACG | 15 MER | P=S | 1.7, 1.4 | 9 |
| 4851 | T GGC GGG ACT ACG GGG GC | 18 MER | P=S | 0.55, 0.5 | 10 |
| 4872 | GGC GGG ACT ACG GGG | 15 MER | P=S | 1.9, 1.7 | 11 |
| 4338 | ACC GCC AGG GGA ATC CGT CAT | 21 MER | P=S | 0.2, 0.2 | 12 |
| 4883 | GCC AGG GGA ATC CGT CAT | 18 MER | P=S | 1.8, 1.8 | 13 |
| 4889 | AGG GGA ATC CGT CAT | 15 MER | P=S | 2.0, 2.0 | 14 |
| 4890 | GCC AGG GGA ATC CGT | 15 MER | P=S | 0.75, 0.7 | 15 |
| 3657 | CAT CGC CGA TGC dGG GCG ATC | 21 MER | P=S | 0.2 | 16 |
| 4891 | CAT CGC CGA TGC GGG GCG | 18 MER | P=S | 0.3 | 17 |
| 4894 | CAT CGC CGA TCG GGG | 15 MER | P=S | >3.0 | 18 |
| 4895 | CGC CGA TGC GGG GCG | 15 MER | P=S | 0.55 | 19 |
| 4896 | GC CGA TGC GGG G | 12 MER | P=S | 1.2 | 20 |
| 4015 | GTT GGA GAC CGG GGT TGG GG | 21 MER | P=S | 0.22, 0.22 | 21 |
| 4549 | GGA GAC CGG GGT TGG GG | 17 MER | P=S | 0.22, 0.27 | 22 |
| 5365 | GA GAC CGG GGT TGG GG | 16 MER | P=S | 0.47 | 23 |
| 4885 | A GAC CGG GGT TGG GG | 15 MER | P=S | 0.42, 0.51 | 24 |
| 5356 | CGG GGT TGG GG | 11 MER | P=S | 0.7 | 25 |
| 4717 | GG GGT TGG GG | 10 MER | P=S | 0.6 | 26 |

TABLE I-continued

Oligonucleotide inhibition of HSV replication

| ISIS NO | SEQUENCE | LENGTH | COMPOSITION | EC50 $\mu$m | SEQ ID NO |
|---|---|---|---|---|---|
| 5544 | TGG GG | 5 MER | P=S | | |
| 4803 | GG GG | 4 MER | P=S | >3.0 | |
| 4771 | GTT GGA GAC CGG GGT TG | 17 MER | P=S | 0.7 | 27 |
| 4398 | CAC GGG GTC GCC GAT GAA CC | 20 MER | P=S | 0.1 | 28 |
| 4772 | GGG GTC GCC GAT GAA CC | 17 MER | P=S | 0.4 | 29 |
| 4773 | CAC GGG GTC GCC GAT GA | 17 MER | P=S | 0.2 | 30 |
| 4897 | CAC GGG GTC GCC GAT | 15 MER | P=S | 0.13 | 31 |
| 4721 | CAC GGG GTC G | 10 MER | P=S | 0.4 | 32 |
| 5366 | TTG GGG TTG GGG TTG GGG TTG GGGG | 25 MER | P=S | 0.16 | 33 |
| 5367 | TTG GGG TTG GGG TTG GGG TTG GGGG | 25 MER | P=O | >4.0 | 34 |
| 5651 | TT GGGG TT GGGG TT GGGG TT GGGG | 24 MER | P=S | 0.17 | 35 |
| 5677 | GGGG TT GGGG TT GGGG TT GGGG | 22 MER | P=S | 0.2 | 36 |
| 5652 | TT GGGG TT GGGG TT GGGG TT | 20 MER | P=S | 0.16 | 37 |
| 5653 | TT GGGG TT GGGG TT GGGG | 18 MER | P=S | 0.2 | 38 |
| 5676 | GGGG TT GGGG TT GGGG | 16 MER | P=S | 0.23 | 39 |
| 5675 | TT GGGG TT GGGG TT | 14 MER | P=S | 0.42 | 40 |
| 5674 | TT GGGG TT GGGG | 12 MER | P=S | 1.5 | 41 |
| 5320 | TT GGGG TT | 8 MER | P=S | >3.0 | |
| 5739 | TT GGGG | MER | P=S | >3.0 | |
| 5544 | T GGGG | 5 MER | P=S | >3.0 | |
| 4803 | GGGG | 4 MER | P=S | >3.0 | |
| 4560 | GGGG C GGGG C GGGG C GGGG C G | 21 MER | P=S | 0.18 | 42 |
| 5649 | TT GGGG TT GGGG TT GGGG TT GGGG | 24 MER | P=O | >3.0 | 43 |
| 5670 | GGGG TT GGGG TT GGGG TT GGGG | 22 MER | P=O | >3.0 | 44 |
| 5650 | TT GGGG TT GGGG TT GGGG TT | 20 MER | P=O | >3.0 | 45 |
| 5590 | GGGG TT GGGG | 10 MER | P=O | >3.0 | 46 |
| 5596 | GGG T GGG T ATA G AAG G GCT CC | 21 MER | P=S | 0.2 | 47 |
| 4664 | GGG T GGG T ATA G AAG G GC | 18 MER | P=S | 0.2 | 48 |
| 4671 | GGG T GGG T ATA GAA G | 15 MER | P=S | 0.4 | 49 |
| 4672 | GGG T GGG T ATA G | 12 MER | P=S | 0.2 | 50 |
| 4692 | T GGG T ATA G AAG GGC TCC | 18 MER | P=S | 1.5 | 51 |
| 4693 | G T ATA G AAG GGC TCC | 15 MER | P=S | >3.0 | 52 |
| 4694 | TA G AAG GGC TCC | 12 MER | P=S | >3.0 | 53 |
| 5753 | UUG GGG UU | 8 MER | O=Me | >3.0 | |
| 5756 | TTA GGG TT | 8 MER | P=S | >3.0 | |
| 5755 | CCC CGG GG | 8 MER | P=S | >3.0 | |

Figure 3:
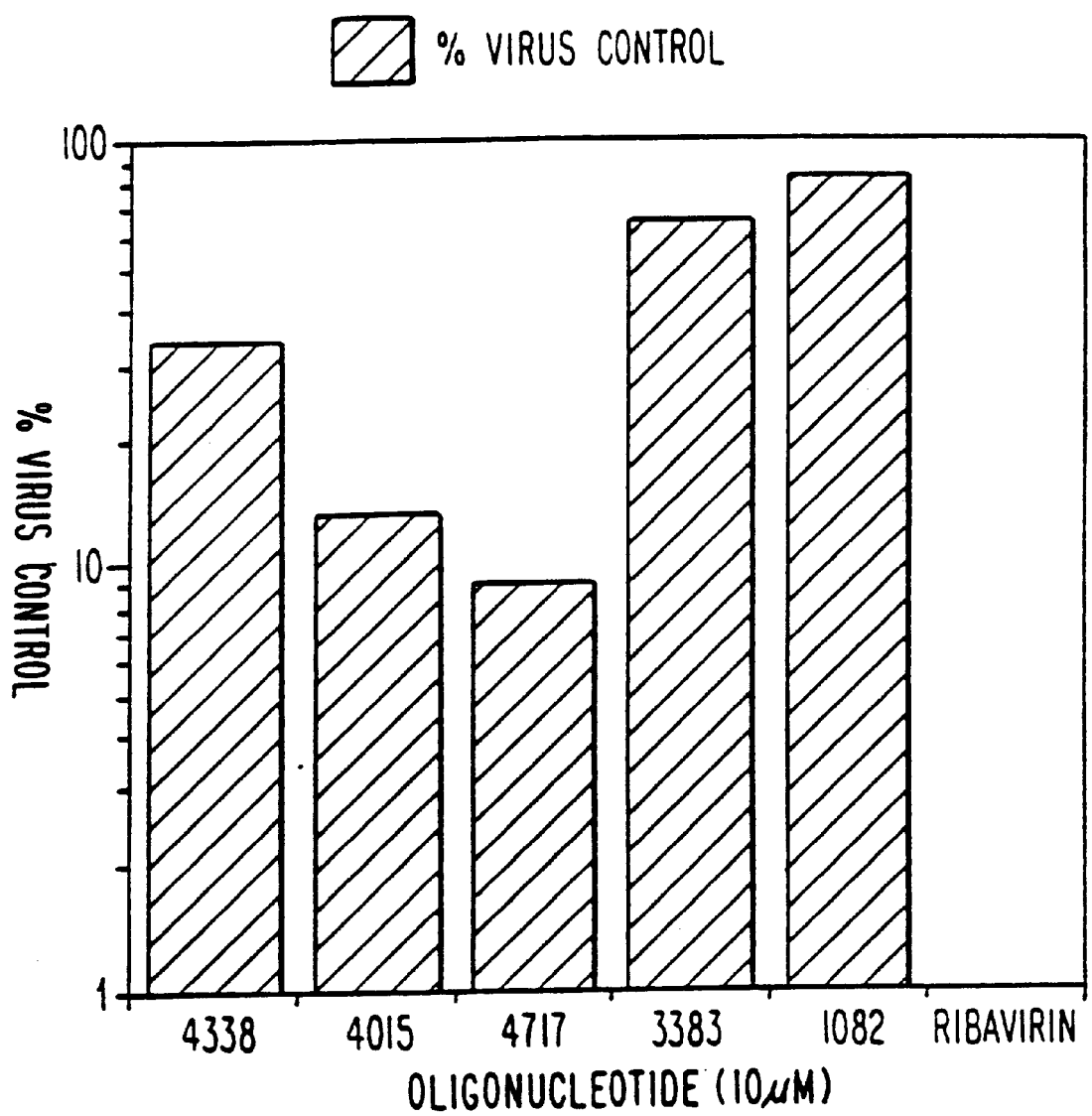
FIG. 3 is a graph showing anti-influenza activity of $G_4$ oligonucleotides as measured by virus yield assay. Oligonucleotides were tested at a single dose of 10 mM. Virus titer is expressed as a percentage of the titer obtained from untreated, infected cells.

Oligonucleotides containing G4 sequences were also tested for antiviral activity against human cytomegalovirus (HCMV, Table 2) and influenza virus (FIG. 3). Again, antiviral activity was determined by ELISA and I.C.$_{50}$'s shown are expressed as a percent of virus titer from untreated controls.

TABLE 2

Antiviral Activity of Oligonucleotides Tested Against HCMV

| ISIS NO | SEQUENCE | COMP. | I.C.$_{50}$ ($\mu$m) | SEQ ID NO |
|---|---|---|---|---|
| 4015 | GTT GGA GAC CGG GGT TGG GG | P=S | 0.17 | 21 |
| 4717 | GGG GTT GGG G | P=S | 1.0 | 26 |
| 5366 | TTG GGG TTG GGG TTG GGG TTG GGG G | P=S | 0.1 | 33 |
| 4560 | GGGGCGGGGCGGGGCGGGGCG | P=S | 0.15 | 42 |
| 5367 | TTG GGG TTG GGG TTG GGG TTG GGG G | P=O | >2.0 | 34 |

Figure 2:
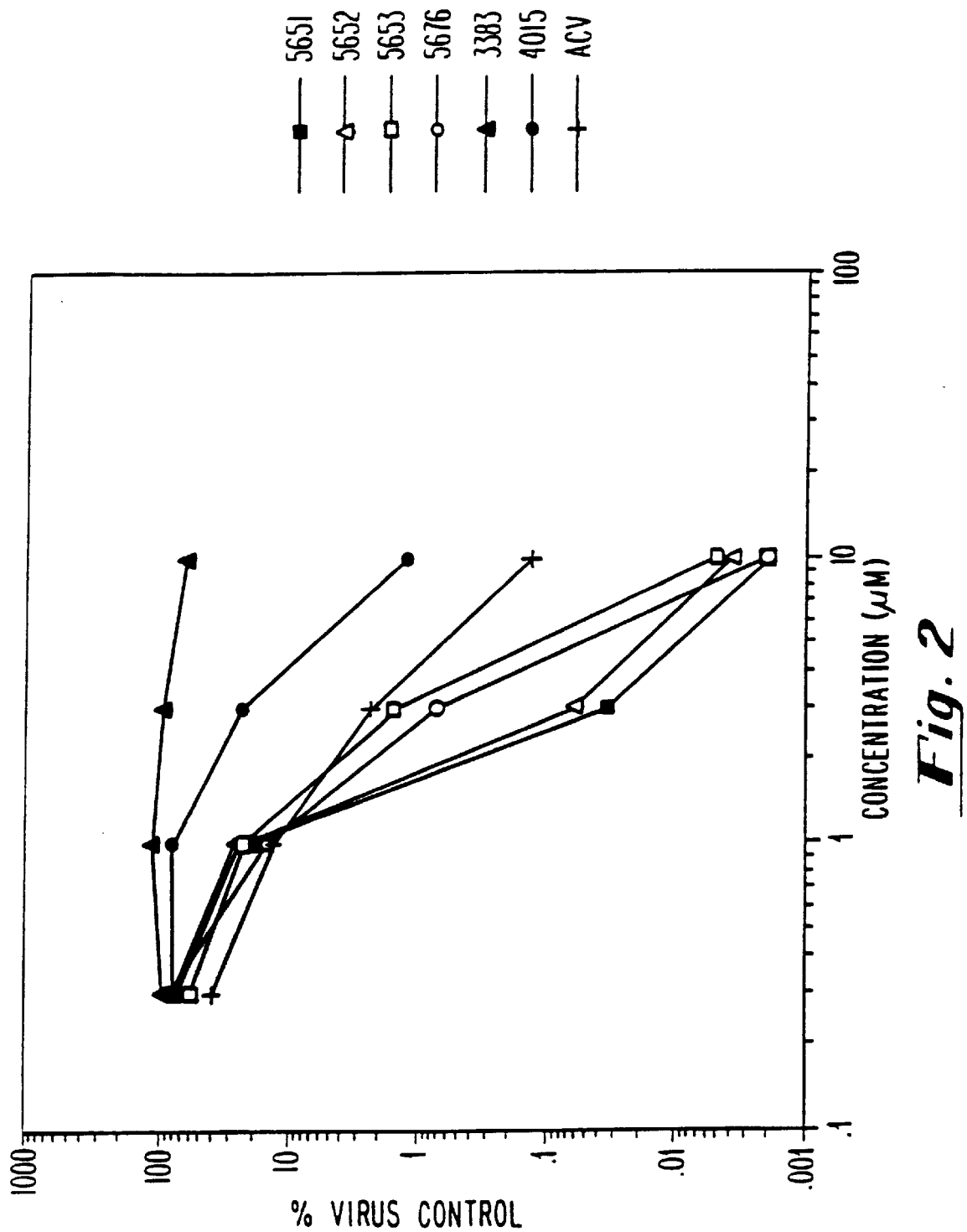
FIG. 2 is a graph showing dose-dependent anti-HSV activity of $G_4$ oligonucleotides 5651 (SEQ ID NO: 35), 5652 (SEQ ID NO: 37), 5653 (SEQ ID NO: 38), 5676 (SEQ ID NO: 39), and 4015 (SEQ ID NO: 21). 3383 (SEQ ID NO: 122) is a negative control oligonucleotide. ACV is Acyclovir (positive control).

In the experiments it was found that the $G_4$ core was necessary for antiviral activity. Nucleotides surrounding $G_4$ contributed to antiviral activity since deletion of nucleotides flanking the $G_4$ core decreased antiviral activity. Oligonucleotides containing phosphorothioate backbones were most active against HSV in these experiments. Compounds containing a phosphodiester backbone were found to be generally inactive in these studies. Compounds with various multiples of $G_4$ and $T_2$ demonstrated comparable activity against HSV. However, $T_2G_4T_2G_4$ was less active and $T_2G_4T_2$ was inactive. It is believed that it is not necessary that $G_4$ be flanked by $T_2$ since a compound containing multiples of $G_4C$ had antiviral activity similar to that observed for $G_4T_2$. oligonucleotides containing $G_4$ also showed antiviral activity in a HSV virus yield assay, as shown in FIG. 1. $T_2G_4T_2G_4T_2G_4T_2G_4$ (ISIS #5651, SEQ ID NO: 35) showed greater antiviral activity than did Acyclovir at a dose of 3 mM. Several $G_4$ oligonucleotides were subsequently shown to reduce virus yield in a dose-dependent manner (FIG. 2). Oligonucleotides containing $G_4$ also showed significant antiviral activity against HCMV (Table 2) and influenza virus (FIG. 3). Control compounds without $G_4$ sequences did not show antiviral activity.

A series of compounds comprising $G_4$ were tested for HIV activity. The results are shown in Table 3.

TABLE 3

Oligonucleotide inhibition of HIV

| ISIS NO | SEQUENCE | COMPOSITION | IC50 ($\mu$M) | TC50 $\mu$M | TI (TC50/IC50) | SEQ ID NO |
|---|---|---|---|---|---|---|
| 5274 | GCC CCC TA | P=O | INACTIVE | | | |
| 5273 | GCT TTT TA | P=O | INACTIVE | | | |
| 5272 | GCG GGG TA | P=O | INACTIVE | | | |
| 5271 | GCA AAA TA | P=O | INACTIVE | | | |
| 5312 | GCG GGG TA | P=S | 1.3 | | | |
| 5311 | GCA AAA TA | P=S | INACTIVE | >200 | | |
| 5307 | GCT TTT TA | P=S | INACTIVE | | | |
| 5306 | GCC CCC TA | P=S | INACTIVE | | | |
| 5319 | TCG GGG TT | P=S | | | | |
| 5059 | GGG GGG TA | P=S | 0.53 | | | |
| 5325 | CGG GGG TA | P=S | 1.1 | | | |
| 5321 | CCG GGG CC | P=S | 1.7 | | | |
| 5753 | UUG GGG UU | O—ME, P=O | INACTIVE | >>50 | | |
| 5058 | GC GGGG TA | P=S | 1.5 | >25 | | |
| 5756 | TTA GGG TT | P=S | 29 | >50 | | |
| 5755 | CCC CGG GG | P=S | 34 | >>50 | | |
| 5543 | TTT GGG TT | P=S | INACTIVE | | | |
| 5542 | TTT GGG TTT | P=s | INACTIVE | | | |
| 5544 | TGGGG | P=s | 5 | | | |
| 4560 | GGG GCG GGG CGG GGC GGG GCG | P=S | 0.14 | | | 42 |
| 4721 | CAC GGG GTC G | P=S | 0.21, 026 | 142 | 546 | 32 |
| 4338 | ACC GCC AGG GGA ATC CGT CAT | P=S | 0.42 | | | 12 |
| 4897 | CAC GGG GTC GCC GAT | P=S | 0.43 | | | 31 |
| 3657 | CAT CGC CGA TGC GGG GCG ATC | P=S | 0.43 | | | 16 |
| 4873 | CAT GAC CGG GGC | P=S | 1 | | | 4 |
| 5366 | TTG GGG TTG GGG TTG GGG TTG GGGG | P=S | 0.08, 0.1 | 22 | 220 | 33 |
| 5651 | TT GGGG TT GGGG TT GGGG TT GGGG | P=S | 0.1, .18 | 19, 19 | 175 | 35 |
| 5677 | GGGG TT GGGG TT GGGG TT GGGG | P=S | 0.1, 0.19 | 15, 14 | 146 | 36 |
| 5652 | TT GGGG TT GGGG TT GGGG TT | P=S | 0.1, 0.18 | 22, 19 | 227 | 37 |
| 5653 | TT GGGG TT GGGG TT GGGG | P=S | 0.12, 0.19 | 27 | | 38 |
| 5676 | GGG GTT GGG GTT GGG G | P=S | 0.18, 0.28 | 21.23 | 114 | 39 |
| 5675 | TT GGGG TT GGGG TT | P=S | 0.38 | 14 | 36 | 40 |
| 5674 | TT GGGG TT GGGG | P=S | 0.43 | >200 | | 41 |
| 4717 | GGGG TT GGGG | P=S | 0.41 | >25, 39 | | 26 |
| 5320 | TT GGGG TT | P=S | 0.47 | 195, 52 | 415 | |
| 5739 | TT GGGG | P=S | 3.8 | −200 | | |
| 4803 | GGGG | P=S | 4 | >25, 13 | | |
| 5367 | TTG GGG TTG GGG TTG GGG TTG GGGG | P=O | 0.09, 0.13 | 52 | 400 | 34 |
| 5649 | TT GGGG TT GGGG TT GGGG TT GGGG | PC | <0.08, 0.3 | 24, 31 | 300 | 43 |
| 5670 | GGGG TT GGGG TT GGGG TT GGGG | P=O | 0.17, 0.75 | 15 | | 44 |
| 5650 | TT GGGG TT GGGG TT GGGG TT | P=O | 0.64 | 7.6 | 12 | 45 |
| 5666 | TT GGGG TT GGGG TT GGGG | P=O | 0.17, 0.6 | 16.7 | 100 | 54 |
| 5669 | GGGG TT GGGG TT GGGG | P=O | 1.2 | 9.6 | 9 | 55 |
| 5667 | TT GGGG TT GGGG TT | P=O | >22 | 5.6 | | 56 |
| 5668 | TT GGGG TT GGGG | P=O | >21 | 5.2 | | 57 |
| 5590 | GGGG TT GGGG | P=O | >25 | 20 | | 46 |
| 5671 | TT GGGG TT | P=O | 16 | 18.15 | 1 | |
| 5672 | TTGGGG | P=O | >16 | 18 | | |
| 5673 | GGGG | P=O | >1 | 43 | | |

A number of compounds with significant HIV antiviral activity (I.C.$_{50}$ 2 $\mu$M or less) were identified. Compound 5058 is a prototypical phosphorothioate 8-mer oligonucleotide containing a $G_4$ core. When the $G_4$ core was lengthened to $G_5$ or $G_6$, activity was retained. When the $G_4$ core was substituted with $A_4$, $C_4$ or $T_4$, activity was lost. A change in the backbone from phosphorothioate to phosphodiester also produced inactive compounds. The oligonucleotides containing a single $G_4$ run were also found to be inactive as phosphodiesters. However, it was found that oligonucleotides with multiple $G_4$ repeats are active as phosphodiester analogs. Substitution of the nucleotides flanking the $G_4$ core resulted in retention of HIV antiviral activity. The compound TTGGGGTT (ISIS 5320) was the most active of the series. Compounds with 3 G's in a row or 2 G's in a row were found to be inactive. Compounds with various multiples of $G_4$ and $T_2$ were generally more active than the parent TTGGGGTT. However, $T_2G_4$ and $G_4$ were less active. It was found that it was not absolutely necessary that $G_4$ be flanked on both sides because $G_4T_2G_4$ is very active.

Phospholipase $A_2$ Enzyme Activity

Specific oligonucleotide compositions having a $G_4$ conserved sequence have also been identified which selectively inhibit human type II phospholipase $A_2$ and type II phospholipase $A_2$ from selected snake venoms. These agents may prove useful in the treatment of inflammatory diseases, hyper-proliferative disorders, malignancies, central nervous system disorders such as schizophrenia, cardiovascular diseases, as well as the sequelae resulting from the bite of poisonous snakes, most notably rattlesnakes.

Incubation of type II phospholipase $A_2$ with increasing amounts of phosphorothioate deoxyoligonucleotides resulted in a sequence-specific inhibition of phospholipase $A_2$ enzyme activity. Of the oligonucleotides tested, ISIS 3196, SEQ ID NO: 47, was found to exhibit the greatest activity, I.C.$_{50}$ value=0.4 μM. ISIS 3631, SEQ ID NO: 81, and 3628, SEQ ID NO: 78, exhibited I.C.$_{50}$ values approximately 10-fold higher and ISIS 1573, SEQ ID NO: 120, did not significantly inhibit the phospholipase $A_2$ at concentrations as high as 10 μM.

To further define the sequence specificity of oligonucleotides which directly inhibit human type II phospholipase $A_2$ activity, a series of phosphorothioate oligonucleotides were tested for direct inhibition of enzyme activity. A compilation of the results from 43 different sequences is shown in Table 4.

TABLE 4

Sequence Specific Inhibition of Human Type II Phospholipase $A_2$ With Phosphorothioate Deoxyoligonucleotides

| ISIS # | Sequence | % Inhibition (1 uM) | SEQ ID NO |
|---|---|---|---|
| 3181 | TCTGCCCCGGCCGTCGCTCCC | 42.7 | 58 |
| 3182 | CAGAGGACTCCAGAGTTGTAT | 30.2 | 59 |
| 3184 | TTCATGGTAAGAGTTCTTGGG | 25.1 | 60 |
| 3185 | CAAAGATCATGATCACTGCCA | 22.7 | 61 |
| 3191 | TCCCATGGGCCTGCAGTAGGC | 41.5 | 62 |
| 3192 | GGAAGGTTTCCAGGGAAGAGG | 28.1 | 63 |
| 3193 | CCTGCAGTAGGCCTGGAAGGA | 22.6 | 64 |
| 3196 | GGGTGGGTATAGAAGGGCTCC | 98.5 | 47 |
| 3468 | GGGACTCAGCAACGAGGGGTG | 97.5 | 65 |
| 3470 | GTAGGGAGGGAGGGTATGAGA | 88.9 | 66 |
| 3471 | AAGGAACTTGGTTAGGGTAGG | 34.5 | 67 |
| 3472 | TGGGTGAGGGATGCTTTCTGC | 69.0 | 68 |
| 3473 | CTGCCTGGCCTCTAGGATGGG | 25.9 | 69 |
| 3474 | ATAGAAGGGCTCCTGCCTGGC | 13.3 | 70 |
| 3475 | TCTCATTCTGGGTGGGTATAG | 67.0 | 71 |
| 3476 | GCTGGAAATCTGCTGGATGTC | 43.4 | 72 |
| 3477 | GTGGAGGAGAGCAGTAGAAGG | 54.7 | 73 |
| 3478 | TGGTTAAGCACGGAGTTGAGG | 26.4 | 74 |
| 3479 | CCGGAGTACAGCTTCTTTGGT | 42.3 | 75 |

TABLE 4-continued

Sequence Specific Inhibition of Human Type II Phospholipase $A_2$ With Phosphorothioate Deoxyoligonucleotides

| ISIS # | Sequence | % Inhibition (1 uM) | SEQ ID NO |
|---|---|---|---|
| 3480 | TTGCTTTATTCAGAAGAGACC | 24.5 | 76 |
| 3481 | TTTTTGATTTGCTAATTGCTT | 2.2 | 77 |
| 3628 | GGAGCCCTTCTATACCCACCC | 13.6 | 78 |
| 3629 | CACCCCTCGTTGCTGAGTCCC | 20.5 | 79 |
| 3630 | TCTCATACCCTCCCTCCCTAC | 17.6 | 80 |
| 3631 | AGGTCGAGGAGTGGTCTGAGC | 20.7 | 81 |
| 3632 | CCAGGAGAGGTCGGTAAGGCG | 29.2 | 82 |
| 3633 | GTAGGGATGGGAGTGAAGGAG | 58.5 | 83 |
| 3659 | TGCTCCTCCTTGGTGGCTCTC | 38.2 | 84 |
| 3663 | CTCTGCTGGGTGGTCTCAACT | 16.3 | 85 |
| 3665 | GGACTGGCCTAGCTCCTCTGC | 45.8 | 86 |
| 3669 | GGTGACAAATGCAGATGGACT | 34.7 | 87 |
| 3671 | TAGGAGGGTCTTCATGGTAAG | 49.3 | 88 |
| 3676 | AGCTCTTACCAAAGATCATGA | 24.5 | 89 |
| 3679 | AGTAGGCCTGGAAGGAAATTT | 30.3 | 90 |
| 3688 | TGGCCTCACCGATCCGTTGCA | 43.1 | 91 |
| 3694 | ACAGCAGCTGTGAGGAGACAC | 28.2 | 92 |
| 3697 | ACTCTTACCACAGGTGATTCT | 39 | 93 |
| 3712 | AGGAGTCCTGTTTTGAAATCA | 31.8 | 94 |
| 4015 | GTTGGAGACCGGGGTTGGGG | 79.4 | 21 |
| 4133 | AGTGCACGTTGAGTATGTGAG | 37.3 | 95 |
| 4149 | CTACGGCAGAGACGAGATAGC | 20.2 | 96 |
| 4338 | ACCGCCAGGGGAATCCGTCAT | 100 | 12 |
| 4560 | GGGGCGGGGCGGGGCGGGG | 100 | 42 |

Most of the oligonucleotides significantly inhibited phospholipase $A_2$ enzyme activity at a concentration of 1 μM. Furthermore, a population of oligonucleotides were found to completely inhibit phospholipase $A_2$ activity at 1 μM concentration. A common feature of those oligonucleotides which inhibit greater than 50% phospholipase $A_2$ enzyme activity is the occurrence of 2 or more runs of guanine residues, with each run containing at leas. 3 bases. More guanine residues in the run, or more runs, resulted in more potent oligonucleotides. As an example, ISIS 3196, SEQ ID NO: 47, and ISIS 3470, SEQ ID NO: 66, both have three sets of guanine runs, with each run three bases in length. Both oligonucleotides completely inhibited human type II phospholipase $A_2$ enzyme activity at a concentration of 1 μM. Two oligonucleotides were found to be an exception to this finding. ISIS 3477, SEQ ID NO: 73, contained 3 sets of guanine runs, but they were only 2 bases in length. This oligonucleotide inhibited enzyme activity by 54 .7% at 1 μM. A second oligonucleotide, ISIS 4338, SEQ ID NO: 12, contained only 1 run of guanine residues, 4 bases in length. In this experiment, ISIS 4338, SEQ ID NO: 12, completely inhibited human type II phospholipase $A_2$ at a concentration of 1 μM.

To further define the minimum pharmacophore responsible for inhibition of human type II phospholipase $A_2$, truncated versions of ISIS 3196, SEQ ID NO: 47 and 4015, SEQ ID NO: 21, were tested for activity. In addition, the effects of base substitutions on the activity of a truncated version of ISIS 3196, SEQ ID NO: 47, were investigated. The results are shown in Table 5. As the effects of base substitution and truncation were performed in two separate experiments, the data from both experiments are shown.

TABLE 5

Identification of the Minimum Pharmacophore for PLA$_2$ Inhibition

| ISIS # | Sequence | % Inhibition (1 μM) | SEQ ID NO |
|---|---|---|---|
| 3196 | GGG TGG GTA TAG AAG GGC TCC | 76.2 | 47 |
|  | GGG TGG GTA TAG AAG GGC | 85.3 | 97 |
|  | GGG TGG GTA TAG AAG | 82.5 | 98 |
| 4672 | GGG TGG GTA TAG | 73.9 | 50 |
|  | TGG GTA TAG AAG GGC TCC | 84.6 | 99 |
|  | GTA TAG AAG GGC TCC | 9.2 | 100 |
|  | TAG AAG GGC TCC | 0 | 101 |
|  | TGG GTA TAG AAG GGC | 33.5 | 102 |
| 3196 | GGG TGG GTA TAG AAG GGC TCC | 100 | 47 |
| 4672 | GGG TGG GTA TAG | 94.6 | 50 |
| 4947 | AGG TGG GTA TAG | 22.7 | 103 |
| 4955 | GGG AGG GTA TAG | 97.5 | 104 |
| 4956 | GGG CGG GTATAG | 92.0 | 105 |
| 4957 | GGG TGG ATA TAG | 81.9 | 106 |
| 4946 | GGG TGG GAA TAG | 73.2 | 107 |
| 4962 | GGG TGG GTA T | 36.3 | 108 |
| 4015 | GTT GGA GAC CGG GGT TGG GG | 98.5 | 21 |
| 4771 | GTT GGA GAC CGG GGT TGG | 17.1 | 27 |
| 4549 | GGA GAC CGG GGT TGG GG | 96.2 | 22 |
| 4717 | GG GGT TGG GG | 83.1 | 26 |
| 5544 | TGG GG | 50 |  |
| 4803 | GG GG | 0 |  |

These results demonstrate that the minimum pharmacophore is 4 G's or two runs of 3 guanines. For ISIS 4015, SEQ ID NO: 21, a 10-base phosphorothioate oligonucleotide containing the sequence GGGGTTGGGG (SEQ ID NO:26) retains full inhibitory activity. A 5-base phosphorothioate oligonucleotide with the sequence TGGGG (ISIS 5544) inhibited enzyme activity by 50% at 1 μM; complete inhibition of enzyme activity was observed at a concentration of 3 μM by ISIS 5544.

A 12-base phosphorothioate oligonucleotide with the sequence GGGTGGGTATAG (ISIS 4672, SEQ ID NO: 50) was shown in one experiment to exhibit almost the same inhibition as the 21 base oligonucleotide, ISIS 3196, SEQ ID NO: 47 (Table 5). Removal of the last two 3'-bases from the 12-mer results in a loss of activity (ISIS 4962, SEQ ID NO: 108). Base substitutions experiments demonstrate that the base separating the two guanine runs does not markedly affect the activity. Substitution of the 5'-guanine with an adenine results in loss of activity. These data suggest that the 5'-guanine plays an important role in maintaining the activity of the oligonucleotide. Further supporting an important role of the 5'-guanine in this sequence was the finding that addition of a fluorescein phosphoramidite or a 5'-phosphate resulted in loss of activity.

Figure 4:
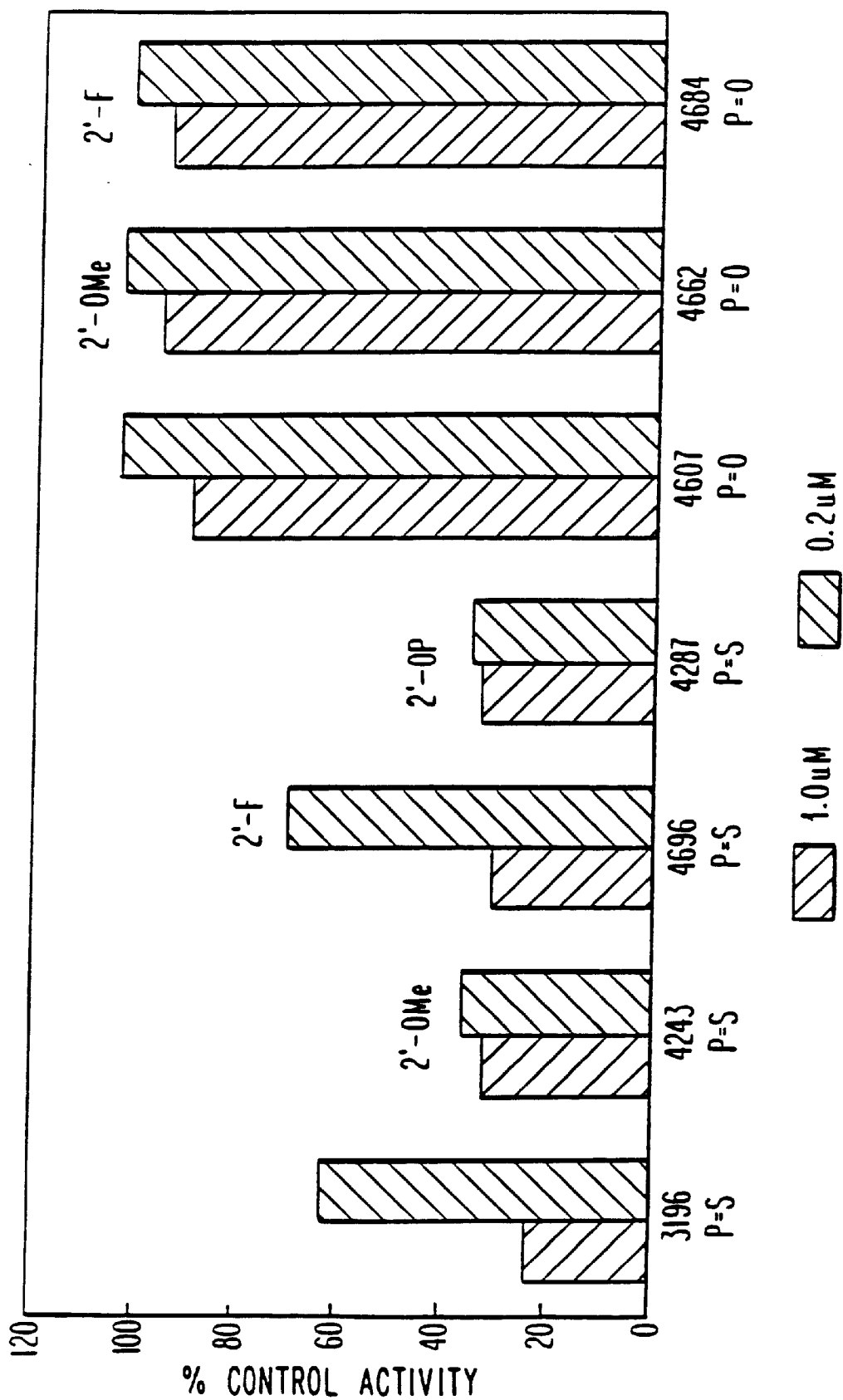
FIG. 4 is a graph showing the inhibition of phospholipase $A_2$ by various 2'-substituted oligonucleotides.

All of the oligonucleotides used in the assays described above were deoxyoligonucleotides. To determine if the effects were specific to DNA oligonucleotides, 2'-substituted analogs were tested for activity. The results are shown in FIG. 4. In each case the internucleosidic linkage was phosphorothioate. No difference in potency was observed if the 2'-positions were substituted with fluorine. Substitution of the 2'-position with methyl and propyl enhanced the inhibitory activity towards human type II phospholipase A$_2$. Replacement of the phosphorothioate backbone with phosphodiester backbone resulted in loss of inhibitory activity. This loss of inhibitory activity by phosphodiester oligonucleotides was not due to degradation of the oligonucleotides, as the oligonucleotides were found to be stable for at least 4 hours in the incubation buffer. The phospholipase A$_2$ enzyme assays were 15 minutes in duration.

In summary, these results demonstrate that phosphorothioate oligonucleotides containing two or more runs of guanines, with each run at least three bases in length are potent inhibitors of human type II phospholipase A$_2$ enzyme activity. Substitution of the 2'-position with either methyl or propyl groups enhanced inhibitory activity. The phosphorothioate internucleosidic linkage was found to be obligatory for biological activity.

Modulation of Telomere Length

Oligonucleotides capable of modulating telomere length are also contemplated by this invention. In human cells, the sequence TTAGGG is repeated from hundreds to thousands of times at both ends of every chromosome, depending on cell type and age. It is believed that oligonucleotides having a sequence $(N_XG_{3-4})_QN_X$ wherein X is 1–8 and Q is 1–6 would be useful for modulating telomere length.

Since telomeres appear to have a role in cell aging, i.e., telomere length decreases with each cell division, it is believed that such oligonucleotides would be useful for modulating the cell's aging process. Altered telomeres are also found in cancerous cells; it is therefore also believed that such oligonucleotides would be useful for controlling malignant cell growth. Therefore, modulation of telomere length using oligonucleotides of the present invention could prove useful for the treatment of cancer or in controlling the aging process.

The following examples are provided for illustrative purposes only and are not intended to limit the invention.

EXAMPLES

Example 1

Oligonucleotide Synthesis

DNA synthesizer reagents, controlled-pore glass (CPG)-bound and B-cyanoethyldiisopropylphosphoramidites were purchased from Applied Biosystems (Foster City, Calif.). 2-O-Methyl B-cyanoethyldiisopropylphosphoramidites were purchased from Chemgenes (Needham, Mass.). Phenoxyacetyl-protected phosphoramadites for RNA synthesis were purchased from BioGenex (Hayward, Calif.)

Oligonucleotides were synthesized on an automated DNA synthesizer (Applied Biosystems model 380B) 2'-O-Methyl oligonucleotides were synthesized using the standard cycle for unmodified oligonucleotides, except the wait step after pulse delivery of tetrazole and base was increased to 360 seconds. The 3' base bound to the CPG used to start the synthesis was a 2'-deoxyribonucleotide. After cleavage from the CPG column and deblocking in concentrated ammonium hydroxide at 55° C. (18 hours), the oligonucleotides were purified by precipitation two times out of 0.5 M NaCl solution with 2.5 volumes ethanol. Analytical gel electrophoresis was accomplished in 20% acrylamide, 8 M urea, 45 mM Tris-borate buffer, pH=7.0. Oligonucleotides were judged from polyacrylamide gel electrophoresis to be greater than 85% full length material.

Example 2

HIV Inhibition

Acute HIV Infection Assay

The human T-lymphoblastoid CEM cell line was maintained in exponential growth phase in RPMI 1640 with 10% fetal calf serum, glutamine, and antibiotics. On the day of the assay, the cells were washed and counted by trypan blue exclusion. These cells (CEM-IIIB) were seeded in each well of a 96-well microtiter plate at 5×10$^3$ cells per well. Following the addition of cells to each well, the oligonucleotides were added at the indicated concentrations and serial half log dilutions. Infectious HIV-1$_{IIIB}$ was immediately added to each well at a multiplicity of infection determined to give complete cell killing at 6 days post-infection. Following 6 days of incubation at 37° C., an aliquot of supernatant was removed from each well prior to the addition of the tetrazolium dye XTT to each well. The XTT was metabolized to a formazan product by viable cells and the results calculated spectrophotometrically with a Molecular Devices Vmax Plate Reader. The XTT assay measures protection from the HIV-induced cell killing as a result of the addition of test compounds. The supernatant aliquot was utilized to confirm the activities determined in the XTT assay. Reverse transcriptase assays and p24 ELISA were performed to measure the amount of HIV released from the infected cells. Protection from killing results in an increased optical density in the XTT assay and reduced levels of viral reverse transcriptase and p24 core protein.

Example 3

HSV-1 Inhibition

HSV-1 Infection ELISA Assay

Confluent monolayers of human dermal fibroblasts were infected with HSV-1 (KOS) at a multiplicity of 0.05 pfu/cell. After a 90 minute adsorption at 37° C., virus was removed and culture medium containing oligonucleotide at the indicated concentrations was added. Two days after infection medium was removed and cells fixed by addition of 95% ethanol. HSV antigen expression was quantitated using an enzyme linked immunoassay. Primary reactive antibody in the assay was a monoclonal antibody specific for HSV-1 glycoprotein B. Detection was achieved using biotinylated goat anti-mouse IgG as secondary antibody followed by reaction with streptavidin conjugated B-galactosidase. Color was developed by addition of chlorophenol red B-D-galactopyranoside and absorbance at 570 nanometers was measured. Results are expressed as percent of untreated control.

Virus Yield Assay

Confluent monolayers of human dermal fibroblasts were infected with HSV-1 (KOS) at a multiplicity of 0.5 pfu/cell. After a 90 minute adsorption at 37° C., virus was removed and 1 ml of culture medium containing oligonucleotide at the indicated concentrations was added. Control wells received 1 ml of medium which contained no oligonucleotide. 2 days after infection, culture medium and cells were harvested and duplicate wells of each experimental point were combined. The suspension was frozen and thawed 3 times, then drawn through a 22 gauge needle five times. Virus titer was determined by plaque assay on Vero cell monolayers. Dilutions of each virus preparation were prepared and duplicates were adsorbed onto confluent Vera monolayers for 90 minutes. After adsorption, virus was removed, cells were rinsed once with phosphate-buffered saline, and overlaid with 2 ml of medium containing 5.0% FBS and methyl cellulose. Cells were incubated at 37° C. for 72 hours before plaques were fixed with formaldehyde and stained with crystal violet. The number of plaques from treated wells was compared to the number of plaques from control wells. Results are expressed as percent of virus titer from untreated control cells and shown in FIG. 2.

Example 4

Cytomegalovirus Inhibition

ELISA Assay

Confluent monolayer cultures of human dermal fibroblasts were treated with oligonucleotides at the indicated concentrations in serum-free fibroblast growth medium. After overnight incubation at 37° C., culture medium containing oligonucleotides was removed, cells were rinsed and human cytomegalovirus was added at a multiplicity of infection of 0.1 pfu/cell. After a 2 hour adsorption at 37° C., virus was removed and fresh fibroblast growth medium containing oligonucleotide at the indicated concentrations was added. Two days after infection, old culture medium was removed and replaced with fresh fibroblast growth medium containing oligonucleotides at the indicated concentrations. Six days after infection media was removed, and cells fixed by addition of 95% ethanol. HCMV antigen expression was quantitated using an enzyme linked immunoassay. Primary reactive antibody in the assay was a monoclonal antibody specific for a late HCMV viral protein. Detection was achieved using biotinylated goat anti-mouse IgG as secondary antibody followed by reaction with streptavidin conjugated B-galactosidase. Color was developed by addition of chlorophenol red B-D-galactopyranoside and absorbance at 575 nanometers measured using an ELISA plate reader. Results are expressed as percent of untreated control.

Example 5

Influenza Virus Inhibition

Virus Yield Assay

Confluent monolayer cultures of Madin-Darby canine kidney (MDCK) cells were treated with oligonucleotide at a concentration of 10 MM in serum-free Dulbecco's modified Eagle's medium (DMEM) containing 0.2% BSA. After incubation at 37° C. for 2 hours, human influenza virus (A/PR strain) was added to the cells at a multiplicity of infection of 0.00125 pfu/cell. Virus was adsorbed for 30 minutes at 37° C. Cells were washed and refed with fresh medium containing oligonucleotide at a concentration of 10 $\mu$M, plus 0.2% BSA, and 3 mg/ml trypsin. One day after infection, medium was harvested. Viral supernatants were titered on MDCK cells. MDCK cells grown in 6-well dishes were infected with dilutions of each virus preparation. After adsorption for 30 minutes at 37° C., virus was removed from the monolayers and cells were overlaid with 2.5 ml of fresh medium containing 0.2% BSA, 3 $\mu$g/ml trypsin, and 0.44% agarose. Twenty-four hours after infection, cells were fixed in 3.5% formaldehyde and plaques visualized by staining monolayers with crystal violet. Results are expressed as a percentage of the titer of virus stock from untreated MDCK cells.

Example 6

Identification of Oligonucleotide Inhibition of Human Type II Phospholipase A$_2$ The human epidermal carcinoma cell line A431 was purchased from American Type Culture Collection. Cells were grown in Dulbecco's Modified Eagle's Medium containing 4.5 gm glucose per liter and 10% fetal calf serum. Type II phospholipase A$_2$ was prepared from A431 cells by cultivating confluent monolayers with Opti-MEM (Gibco). The medium was concentrated 5 to 10 fold on an Amicon ultrafiltration device using YM-5 membranes. The concentrated spent medium was used as a source of human type II phospholipase $A_2$. Previous studies have demonstrated that A431 cells only secrete type II phospholipase $A_2$.

Phospholipase $A_2$ assays were performed utilizing $^3$H-oleic acid labelled *E. coli* as the substrate. $^3$H-Oleic acid labelled *E. coli* were prepared as described by Davidson et al. *J. Biol. Chem.* 1987, 262, 1698). The reactions contained 100,000 cpm of $^3$H-oleic acid labelled *E. coli,* 50 mM Tris-HCl, pH=7.4, 50 mM NaCl, 1 mM $CaCl_2$, and 50 μg bovine serum albumin in a final reaction volume of 200 μL. Reactions were initiated by the addition of the *E. coli* substrate. Reactions were terminated by the addition of 100 μL 2 N HCl and 100 μL 100 mg/ml fatty acid free bovine serum albumin. Samples were vortexed and centrifuged at 17,000×g for 5 minutes. The amount of $^3$H-oleic acid in the supernatant was determined by counting a 300 μL aliquot in a liquid scintillation counter. Oligonucleotides were added to the incubation mixture prior to the addition of the substrate.

Example 7

Structural Requirement for Inhibition of Human Type II Phospholipase $A_2$ by Phosphorothioate Oligonucleotides The oligonucleotides which inhibit human type II phospholipase $A_2$ share a common feature with telomeric DNA sequences in that both are composed of guanine rich sequences. Telomeric sequences such as that from Oxytricha ($XXXG_4T_4G_4T_4G_4T_4G_4T_4G_4$, SEQ ID NO: 121) form an unusual structure termed a G quartet. The formation of this structure is monovalent cation dependent and is disrupted by high temperature. To determine if oligonucleotide structure was part of the active pharmacophore, ISIS 3196, SEQ ID NO: 47, was placed in boiling water for 15 minutes prior to addition to the assay. Boiling reduced the inhibitory activity of ISIS 3196, SEQ ID NO: 47, from 94% inhibition to 21% inhibition. Examination of the oligonucleotide by denaturing gel electrophoresis demonstrated that boiling did not cause the oligonucleotide to fragment. Separation of native and denatured ISIS 3196, SEQ ID NO: 47, by gel filtration chromatography on a Superdex G-75 column demonstrated that in its native conformation, this oligonucleotide exists as several molecular species. Boiling ISIS 3196, SEQ ID NO: 47, prior to chromatography resulted in loss of high molecular weight species and appearance of the oligonucleotide in the lower molecular weight species. From these studies we can conclude that structure appears to be part of the pharmacophore for ISIS 3196, SEQ ID NO: 47.

Example 8

Specificity of Phosphorothioate Oligonucleotide for Select Type II Phospholipase $A_2$ Bovine pancreatic phospholipase $A_2$, *Apis mellifera* phospholipase $A_2$, *Naja naja naja* phospholipase $A_2$, and *Crotalus durissus terrificus* phospholipase $A_2$ were obtained from Sigma Chemical Co. (St. Louis, Mo.). Phospholipase $A_2$ isolated from the venom of *Trimeresurus flavoridis* was obtained from Calbiochem (La Jolla, Calif.), and phospholipase $A_2$ from *Agkistrodon piscivorus piscivorus* was partially purified from whole venom (Sigma Chemical Co.) by chromatography on a Mono S column (Pharmacia, Upsalla, Sweden).

Figure 5:
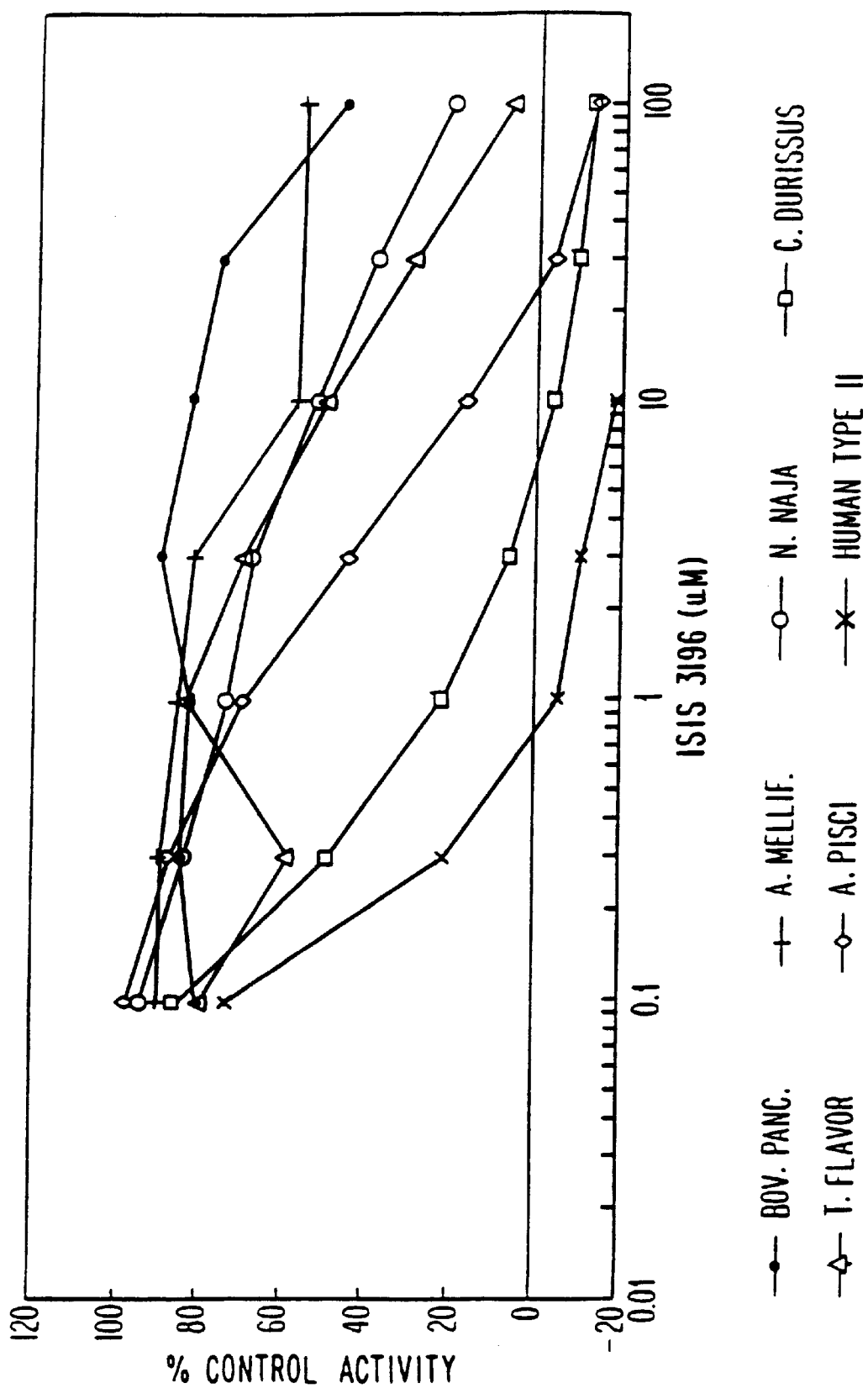
FIG. 5 is a graph showing the effect of ISIS 3196 (SEQ ID NO: 47) on enzyme activity of phospholipase $A_2$ isolated from different sources.

To determine the specificity of ISIS 3196, SEQ ID NO: 47, towards human type II phospholipase $A_2$, phospholipase $A_2$ from different sources were tested for inhibitory activity (FIG. 5). Human type II phospholipase $A_2$ was the most sensitive of all the enzymes tested to the inhibitory effects of ISIS 3196, SEQ ID NO: 47, $I.C._{.50} \approx 0.15$ μM (FIG. 5). Phospholipase $A_2$ isolated from *Crotalus durissus* venom (rattlesnake), also a type II enzyme, was the next most sensitive to the effects of ISIS 3196, SEQ ID NO: 47, $I.C._{.50} \approx 0.3$ μM, followed by phospholipase $A_2$ isolated from the venom of *Agkistrodon piscivorus piscivorus* (cottonmouth), also a type II enzyme, $I.C._{.50} \approx 3$ μM. Bovine pancreatic phospholipase $A_2$, a type I enzyme, was the most resistant of all the enzymes tested to the effects of ISIS 3196, SEQ ID NO: 47, $I.C._{.50} \approx 100$ μM (FIG. 5). Phospholipase $A_2$ isolated from *Naja naja naja* venom (cobra venom), a type 1 enzyme and from *Trimeresurus flavoridis* (Asian pit viper, habu) were both relatively resistant to the inhibitory effect of ISIS 3196, SEQ ID No; 47, with $I.C._{.50}$ values greater than 10 μM. Phospholipase $A_2$ isolated from *Apis mellifera* (honeybee), neither a type I or type II enzyme, was also quite resistant to the inhibitory activity of ISIS 3196, SEQ ID NO: 47, with an $I.C._{.50}$ value greater than 100 μM.

These results demonstrate that ISIS 3196, SEQ ID NO: 47, selectively inhibits human type II phospholipase $A_2$. Other type II phospholipase $A_2$, such as those isolated from Crotalus and Agkistrodon venoms, were also sensitive to the effects of ISIS 3196, SEQ ID NO: 47. While, in general, type I enzymes were more resistant to the effects of ISIS 3196, SEQ ID NO: 47. Although bee venom (*Apis mellifera*) phospholipase $A_2$ does not bear a strong sequence homology to either type I or type II enzymes, it is more closely related to type I enzymes. Like other type I enzymes, it is relatively resistant to the inhibitor effects of ISIS 3196, SEQ ID NO: 47.

Example 9

Figure 6:
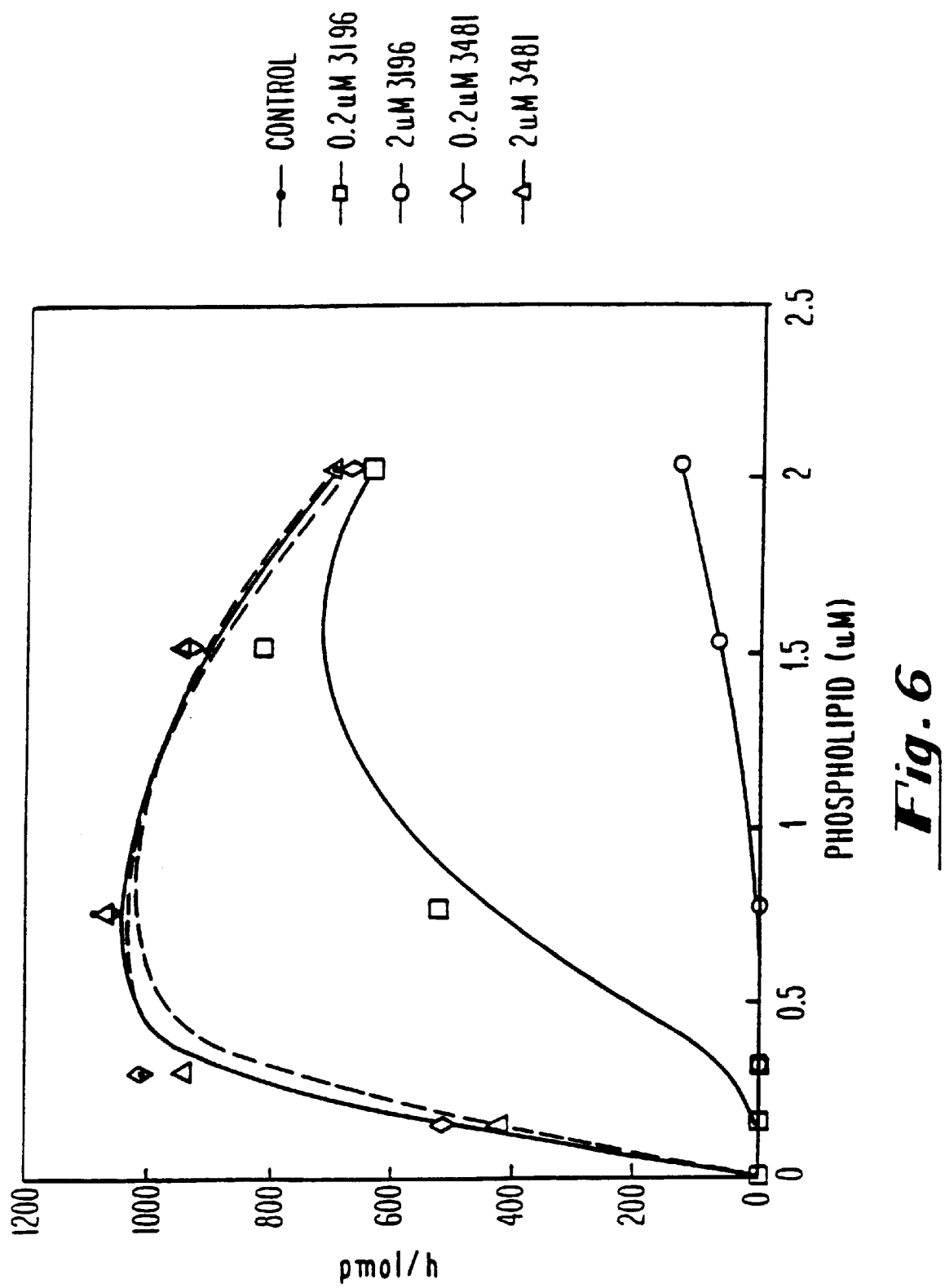
FIG. 6 is a graph showing the results of an experiment wherein human phospholipase $A_2$ was incubated with increasing amounts of E. coli substrate in the presence of oligonucleotides ISIS 3196 (SEQ ID NO: 47) and ISIS 3481 (SEQ ID NO: 77).

Mechanism of Inhibition of Human Type II Phospholipase $A_2$ by Phosphorothioate Oligonucleotides As a first step in elucidation of the mechanism by which phosphorothioate oligonucleotides inhibit phospholipase $A_2$, the effects of the oligonucleotides on the substrate kinetics of the enzymes were determined. Human type II phospholipase $A_2$ was incubated with increasing amounts of *E. coli* substrate in the presence of oligonucleotides ISIS 3196, SEQ ID NO: 47, and ISIS 3481, SEQ ID NO: 77 (FIG. 6). The concentration of *E. coli* phospholipid was determined by lipid phosphorus analysis as described by Bartlett, *J. Biol. Chem.* 1959, 234:466. The results demonstrate that ISIS 3481, SEQ ID NO: 77, at 0.2 μM and 2 μM did not modify the substrate kinetics of human type II phospholipase $A_2$. In contrast, ISIS 3196, SEQ ID NO: 47, behaved as an apparent noncompetitive inhibitor in that the apparent Km and Vmax were both changed in the presence of the oligonucleotide. It is unlikely that ISIS 3196, SEQ ID NO: 47, inhibits human type II phospholipase $A_2$ by chelating calcium which is required for activity, in that the free calcium in the assay was in 500 to 5000-fold excess to the oligonucleotide.

Example 10

Modulation of Telomere Length by $G_4$ Phosphorothioate Oligonucleotides

The amount and length of telomeric DNA in human fibroblasts has been shown to decrease during aging as a function of serial passage in vitro. To examine the effect of $G_4$ phosphorothioate oligonucleotides on this process, human skin biopsy fibroblasts are grown as described in Harley, C. B., *Meth. Molec. Biol.* 1990, 5, 25–32. Cells are treated with the oligonucleotides shown in Table 6, by adding the oligonucleotide to the medium to give a final concentration of 1 μM, 3 μM or 10 μM; control cells receive no oligonucleotide. Population doublings are counted and DNA is isolated at regular intervals. Telomere length is determined by Southern blot analysis and plotted against number of population doublings as described in Harley, C. B. et al., *Nature* 1990, 345, 458–460. The slope of the resulting linear regression lines indicates a loss of approximately 50 bp of telomere DNA per mean population doubling in untreated fibroblasts. Harley, C. B. et al., *Nature* 1990, 345, 458–460. Treatment with oligonucleotides of Table 6 is expected to result in modulation of telomere length.

TABLE 6

Effect of $G_4$ Phosphorothioate Oligonucleotides on Telomere Length in Aging Fibroblasts

| ISIS NO. | SEQUENCE | SEQ ID NO: |
|---|---|---|
|  | TT AGGG |  |
| 5739 | TT GGGG |  |
| 5756 | TT AGGG TT |  |
| 5320 | TT GGGG TT |  |
| 5675 | TT GGGG TT GGGG TT | 40 |
| 5651 | TT GGGG TT GGGG TT GGGG TT GGGG | 35 |
|  | TTTT GGGG |  |
|  | TTTA GGGG |  |
| 5673 | GGGG |  |

Example 11

Activity of $G_4$ Phosphorothioate Oligonucleotides against Several Viruses

Antiviral activity of oligonucleotides was determined by CPE inhibition assay for influenza virus, adenovirus, respiratory syncytial virus, human rhinovirus, vaccinia virus, HSV-2 and varicella zoster virus. The MTT cell viability assay was used to assay effects on HIV. HSV-2, adenovirus, vaccinia virus and rhinovirus were assayed in MA104 cells. Respiratory syncytial virus was assayed in HEp-2 cells and influenza virus was assayed in MDCK cells. CEM cells were used in MTT assays of HIV inhibition. Oligonucleotide was added at time of virus infection.

MDCK (normal canine kidney) cells and HEp-2, a continuous human epidermoid carcinoma cell line, were obtained from the American Type Culture Collection, Rockville, Md. MA-104, a continuous line of African green monkey kidney cells, was obtained from Whittaker M. A. Bioproducts, Walkersville, Md.

HSV-2 strain E194 and influenza strain A/NWS/33 (H1N1) were used. Adenovirus, Type 5 (A-5), strain Adenoid 75; respiratory syncytial virus (RSV) strain Long; rhinovirus 2 (R-2), strain HGP; and vaccinia virus, strain Lederlechorioallantoic were obtained from the American Type Culture Collection, Rockville Md.

Cells were grown in Eagle's minimum essential medium with non-essential amino acids (MEM, GIBCO-BRL, Grand Island, N.Y.) with 9% fetal bovine serum (FBS, Hyclone Laboratories, Logan, Utah), 0.1% $NaHCO_3$ for MA104 cells; MEM 5% FBS, 0.1% $NaHCO_3$ for MDCK cells, and MEM, 10% FBS, 0.2% $NaHCO_3$ for HEp-2 cells. Test medium for HSV-2, A-5, R-2 and vaccinia virus dilution was MEM, 2% FBS, 0.18% $NaHCO_3$, 50 µg gentamicin/ml. RSV was diluted in MEM, 5% FBS, 0.18% $NaHCO_3$, 50 µg gentamicin/ml. Test medium for dilution of influenza virus was MEM without serum, with 0.18% $NaHCO_3$, 20 µg trypsin/ml, 2.0 µg EDTA/ml, 50 µg gentamicin/ml.

Ribavirin was obtained from ICN Pharmaceuticals, Costa Mesa, Calif. Acyclovir and 9β-D-arabinofuranosyladenine (ara-A) were Purchased from Sigma Chemical Co., St. Louis, Mo. Ribavirin, acyclovir and ara-A were prepared and diluted in MEM without serum, plus 0.18% $NaHCO_3$, 50 µg gentamicin/ml. Oligonucleotides were diluted in the same solution.

Cells were seeded in 96-well flat bottom tissue culture plates, 0.2 ml/well, and incubated overnight in order to establish monolayers of cells. Growth medium was decanted from the plates. Compound dilutions were added to wells of the plate (4 wells/dilution, 0.1 ml/well for each compound) as stocks having twice the desired final concentration. Compound diluent medium was added to cell and virus control wells (0.1 ml/well). Virus, diluted in the specified test medium, was added to all compound test wells 3 wells/ dilution) and to virus control wells at 0.1 ml/well. Test medium without virus was added to all toxicity control wells (1 well/dilution for each comopund test) and to cell control wells at 0.1 ml/well. The plates were incubated at 37° C. in a humidified incubator with 5% $CO_2$, 95% air atmosphere until virus control wells had adequate CPE readings. Cells in test and virus control wells were then examined microscopically and graded for morphological changes due to cytotoxicity. Effective dose, 50% endpoint (ED50) and cytotoxic dose, 50% endpoint (CD50) were calculated by regression analysis of the viral CPE data and the toxicity control data, respectively. The ED50 is that concentration of compound which is calculated to produce a CPE grade halfway between that of the cell controls (0) and that of the virus controls. CD50 is that concentration of compound calculated to be halfway between the concentration which produces no visible effect on the cells and the concentration which produces complete cytotoxicity. The therapeutic index (TI) for each substance was calculated by the formula: TI=CD50/ ED50.

Oligonucleotide sequences are shown in Table 1 except for ISIS 3383 (SEQ ID NO: 122) and ISIS 6071. ISIS 3383 is a scrambled version of ISIS 1082 (SEQ ID NO: 134). ISIS 6071 (TGTGTGTG) is a scrambled version of ISIS 5320. The results are shown in Table 7. Oligonucleotides with ED50 values of less than 50 µM were judged to be active in this assay and are preferred.

TABLE 7

Oligonucleotide activity against RNA and DNA viruses

| | DNA Viruses | | | | RNA Viruses | | | |
|---|---|---|---|---|---|---|---|---|
| Virus: | HSV-2 | VZV | A-5 | Vacc | RSV | Rhino | HIV | Influenza |
| Compound: 3383 | | | | | | | | |
| ED50 | 2.8µM | — | >100 | >100 | 0.7 | >100 | — | 19 |
| TI | >36 | — | — | — | 60 | — | — | >5 |

TABLE 7-continued

Oligonucleotide activity against RNA and DNA viruses

| Virus: | DNA Viruses | | | | RNA Viruses | | | |
|---|---|---|---|---|---|---|---|---|
| | HSV-2 | VZV | A-5 | Vacc | RSV | Rhino | HIV | Influenza |
| 4015 | | | | | | | | |
| ED50 | 0.8 | 29 | >100 | 15 | 0.6 | >100 | 0.16 | 0.6 |
| TI | >125 | 1.0 | <1.0 | >6.7 | 93 | — | 100 | 93 |
| 3657 | | | | | | | | |
| ED50 | 0.6 | >100 | >100 | 18 | 0.8 | >100 | — | 1.0 |
| TI | >167 | 1.0 | <1.0 | >5.6 | >125 | — | — | 56 |
| 4338 | | | | | | | | |
| ED50 | 0.6 | — | 68 | 19 | 1.0 | >100 | — | 0.5 |
| TI | >53 | — | >1.5 | >5.3 | 13 | — | — | >200 |
| 1220 | | | | | | | | |
| ED50 | 0.7 | — | >50 | 46 | — | >50 | — | — |
| TI | >71 | — | — | >1.1 | — | — | — | — |
| 5652 | | | | | | | | |
| ED50 | 0.3 | 18 | >100 | — | 1.9 | >100 | 0.18 | 0.6 |
| TI | >333 | — | <1.0 | — | >53 | — | 227 | 93 |
| ACV | | | | | | | | |
| ED50 | 97.7 | — | — | — | — | — | — | — |
| TI | >45 | — | — | — | — | — | — | — |
| Ribavirin | | | | | | | | |
| ED50 | — | — | 82 | — | 49 | 229 | — | 7.78 |
| TI | — | — | 28 | — | 20 | 10 | — | 202 |
| Ara-A | | | | | | | | |
| ED50 | — | — | — | 15.8 | — | — | — | — |
| TI | — | — | — | 125 | — | — | — | — |
| 5320 | | | | | | | | |
| ED50 | 4 | >100 | >100 | >100 | — | — | 0.4 | 40 |
| TI | — | — | — | — | — | — | 390 | — |
| 6071 | | | | | | | | |
| ED50 | >100 | >100 | >100 | >100 | — | — | 50 | >100 |
| TI | — | — | — | — | — | — | — | — |

Example 12

Testing of Oligonucleotides for Activity against HSV-1

Phosphorothioate oligonucleotides were synthesized which are complementary to regions of the HSV-1 RNA containing clusters of cytosines. These oligonucleotides are shown in Table 8:

TABLE 8

Phosphorothioate oligonucleotides targeted to HSV-1 (sequences written 5' TO 3')

| Oligo # | Sequence | Target | Target Function | SEQ ID NO: |
|---|---|---|---|---|
| 1220 | CAC GAA AGG CAT GAC CGG GGC | UL9, AUG | Ori binding protein | 1 |
| 4274 | CAT GGC GGG ACT ACG GGG GCC | UL27, AUG | virion gB | 8 |
| 4338 | ACC GCC AGG GGA ATC CGT CAT | UL42, AUG | DNA binding protein | 12 |
| 4346 | GAG GTG GGC TTC GGT GGT GA | UL42, 5'UTR | " | 123 |

TABLE 8-continued

Phosphorothioate oligonucleotides targeted to HSV-1 (sequences written 5' TO 3')

| Oligo # | Sequence | Target | Target Function | SEQ ID NO: |
|---|---|---|---|---|
| 3657 | CAT CGC CGA TGC GGG GCG ATC | IE175, AUG | Transc. transactivator | 16 |
| 4015 | GTT GGA GAC CGG GGT TGG GG | UL29, 5'UTR | ssDNA binding protein | 21 |
| 4398 | CAC GGG GTC GCC GAT GAA CC | " | " | 28 |
| 4393 | GGG GTT GGG GAA TGA ATC CC | " | " | 124 |
| 4348 | GGG TTG GAG ACC GGG GTT GG | " | " | 125 |
| 4349 | GGT TGG AGA CCG GGG TTG GG | " | " | 126 |
| 4341 | TGG AGA CCG GGG TTG GGG AA | " | " | 127 |
| 4342 | TTG GAG ACC GGG GTT GGG GA | " | " | 128 |
| 4350 | GAC GGT CAA GGG GAG GGT TGG | " | " | 129 |
| 4435 | GGG GAG ACC GAA ACC GCA AA | UL20, 5'UTR | Viral egress | 130 |
| 4111 | CCT GGA TGA TGC TGG GGT AC | UL30, coding | DNA polymerase | 131 |
| 4112 | GAC TGG GGC GAG GTA GGG GT | " | " | 132 |
| 4399 | GTC CCG ACT GGG GCG AGG AT | " | " | 133 |

The oligonucleotides shown in Table 8 were tested for activity against HSV-1 (KOS strain) using an ELISA assay as described in Example 3. Results are expressed as percent of untreated control. From these results, an EC50 (effective oligonucleotide concentration giving 50% inhibition) is calculated for each oligonucleotide. These values, expressed in $\mu$M, are given in Table 9. Oligonucleotides having EC50s of 1 $\mu$M or less in this ELISA assay were judged to have particularly good activity and are preferred. The negative control oligonucleotide, ISIS 1082 (complementary to HSV UL13 translation initiation codon; has no runs of G) had EC50 of 2.5 and 1.8 $\mu$M in duplicate experiments.

TABLE 9

Oligonucleotide inhibition of HSV-1
All oligonucleotides are phosphorothioates

| Oligo # | EC5O ($\mu$M)* |
|---|---|
| 1220 | 0.24, 0.16 |
| 4274 | 0.15, 0.15 |
| 4338 | 0.20, 0.20 |
| 4346 | 0.50 |
| 3657 | 0.20 |
| 4015 | 0.22, 0.22 |
| 4398 | 0.10 |
| 4393 | 0.20 |
| 4348 | 0.40 |
| 4349 | 0.25 |
| 4341 | 0.20 |
| 4342 | 0.20 |
| 4350 | 0.25 |
| 4435 | 0.22 |
| 4111 | 0.60 |
| 4112 | 0.30 |
| 4399 | 0.25 |

*Some experiments were done in duplicate

Example 13

Activity of $G_4$ Phosphorothioate Oligonucleotides against Various Strains of HSV Oligonucleotides were tested against HSV-1 and five strains of HSV-1, of which two (HSV1-DM2.1 and HSV1PAAr) are resistant to acyclovir (ACV) Oligonucleotides were assayed by ELISA as described in Example 3 and results are shown in Table 10. In this assay, oligonucleotides with EC50s of 1 $\mu$M or less were judged to be particularly active and are preferred.

TABLE 10

Oligonucleotide activity against various HSV strains
Results are given as EC50, expressed in $\mu$M

| Compound: | 4015 | 1220 | 3657 | 4338 | 4274 | 1082 | |
|---|---|---|---|---|---|---|---|
| SEQ ID NO: | 21 | 1 | 16 | 12 | 8 | 134 | ACV |
| HSV strain | | | | | | | |
| HSV-1(KOS) | 0.25 | 0.34 | 0.38 | 0.24 | 0.21 | 2.1 | 2.5 |
| HSV-2 | 0.2 | 0.1 | 0.2 | 0.2 | 0.2 | 2.0 | 2.0 |
| HSV1-F | 0.22 | 0.22 | 0.22 | 0.25 | 0.25 | >3.0 | 0.7 |
| HSV1-McKrae | 0.45 | 0.30 | 0.40 | 0.60 | | >3.0 | 1.8 |
| HSV1-DM2.1 | 0.10 | 0.10 | 0.10 | 0.70 | 0.40 | >3.0 | >3.0 |
| HSV1-PAAr | 0.35 | 0.12 | 0.10 | 0.30 | 0.25 | >3.0 | >3.0 |

Example 14

Figure 7:
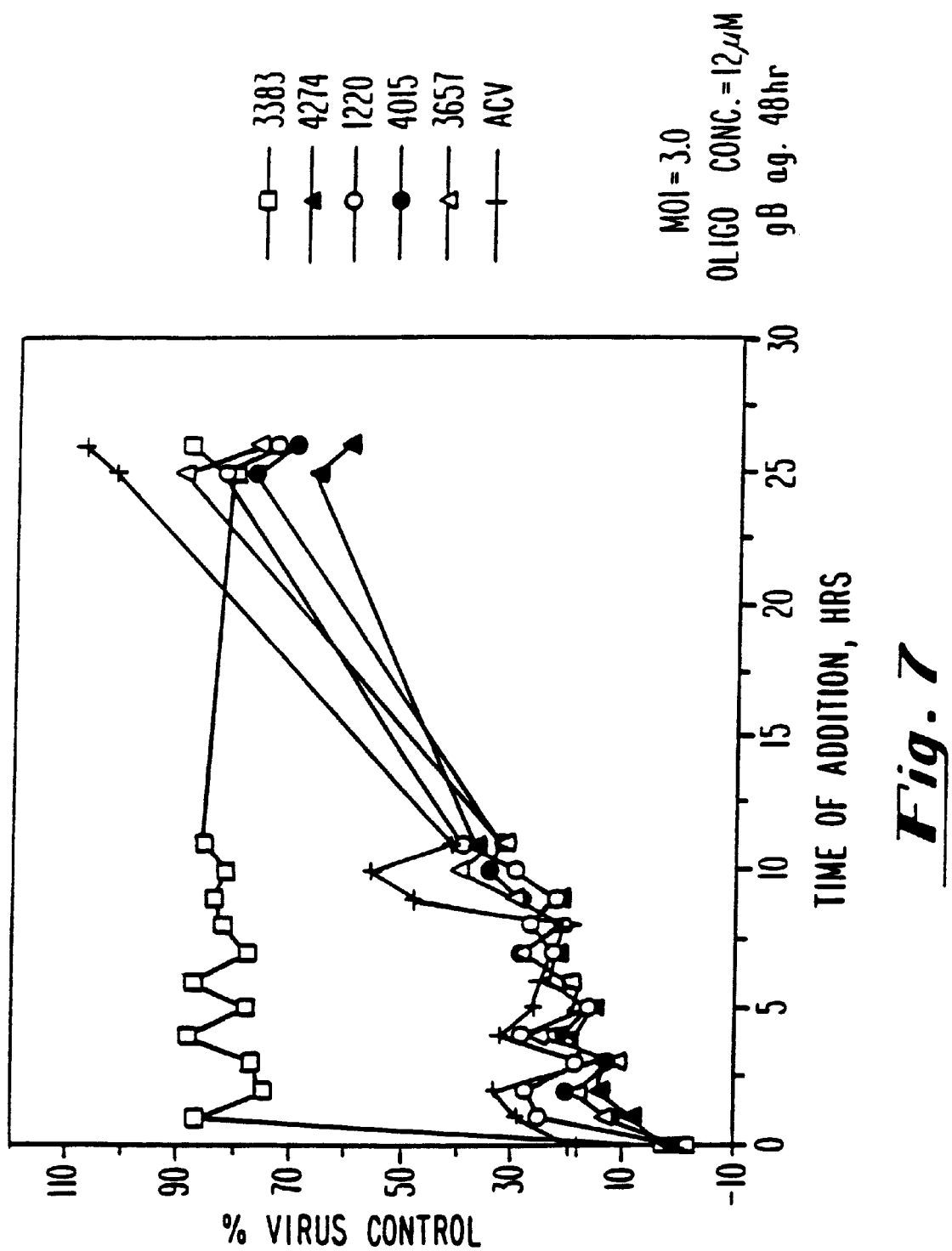
FIG. 7 is a line graph showing the effect of time of oligonucleotide addition on HSV-1 inhibition.

Effect of Time of Oligonucleotide Addition on HSV-1 Inhibition by $G_4$ Phosphorothioate Oligonucleotides NHDF cells were infected with HSV-1 (KOS) at a MOI of 3.0 pfu/cell. Oligonucleotides or ACV were added at a concentration of 12 mM at different times after infection. HSV was detected by ELISA 48 hours after infection. It was found that all oligonucleotides, including scrambled control oligonucleotide 3383, inhibited HSV replication when added to cells at the time of virus infection (t=0), but only oligonucleotides complementary to HSV genes (ISIS 4274, 1220, 4015 and 3657) inhibited HSV replication when added after virus infection. Oligonucleotides showed good antiviral activity when added 8 to 11 hours after infection. This pattern is similar to that observed with ACV, as shown in FIG. 7.

Example 15

Chimeric 2'-O-methyl $G_4$ Oligonucleotides with Deoxy Gaps

A series of phosphorothioate oligonucleotides were synthesized having a 2'-O-methyl substitution on the sugar of each nucleotide in the flanking regions, and 2'-deoxynucleotides in the center portion of the oligonucleotide (referred to as the "deoxy gap"). Deoxy gaps varied from zero to seven nucleotides in length. These chimeric oligonucleotides were assayed by ELISA as described in Example 3 and results are shown in Table 11. In this assay, oligonucleotides with EC50s of 1 $\mu$M or less were judged to be particularly active and are preferred.

TABLE 11

Activity of 2'-O-me G$_4$ oligonucleotides against HSV
(2'-O-me nucleotides shown in bold)

| Oligo # | Sequence | Target | Type | EC50 (μM) | SEQ ID NO: |
|---|---|---|---|---|---|
| 1220 | CAC GAA AGG CAT GAC CGG GGC | UL9, AUG | Parent(deoxy) | 0.24, 0.16 | 1 |
| 4240 | CAC GAA AGG CAT GAC CGG GGC | " | Deoxy gap | | 1 |
| 3657 | CAT CGC CGA TGC GGG GCG ATC | IE175, AUG | Parent(deoxy) | 0.20 | 16 |
| 5377 | CAT CGC CGA TGC GGG GCG ATC | " | 2'-O-me | 1.20 | 16 |
| 4237 | CAT CGC CGA TGC GGG GCG ATC | " | Deoxy gap | | 16 |
| 4015 | GTT GGA GAC CGG GGT TGG GG | UL29, 5'UTR | Parent(deoxy) | 0.22, 0.22 | 21 |
| 4538 | GTT GGA GAC CGG GGT TGG GG | " | Deoxy gap | 0.16 | 21 |
| 5378 | GTT GGA GAC CGG GGT TGG GG | " | 2'-O-me | 0.40 | 21 |
| 4398 | CAC GGG GTC GCC GAT GAA CC | UL29, 5'UTR | Parent(deoxy) | 0.10 | 28 |
| 5039 | CAC GGG GTC GCC GAT GAA CC | " | 2'-O-me | 2.70 | 28 |
| 5189 | CAC GGG GTC GCC GAT GAA CC | " | Deoxy gap | 0.16 | 28 |

Additional chimeric oligonucleotides were synthesized having the sequences of ISIS 4015 and ISIS 4398. These oligonucleotides were 2'-O-methyl oligonucleotides with deoxy gaps as described above, but instead of a uniform phosphorothioate backbone, these compounds had phosphorothioate internucleotide linkages in the deoxy gap region and phosphodiester linkages in the flanking region. These oligonucleotides were not active against HSV in this ELISA assay.

Figure 8:
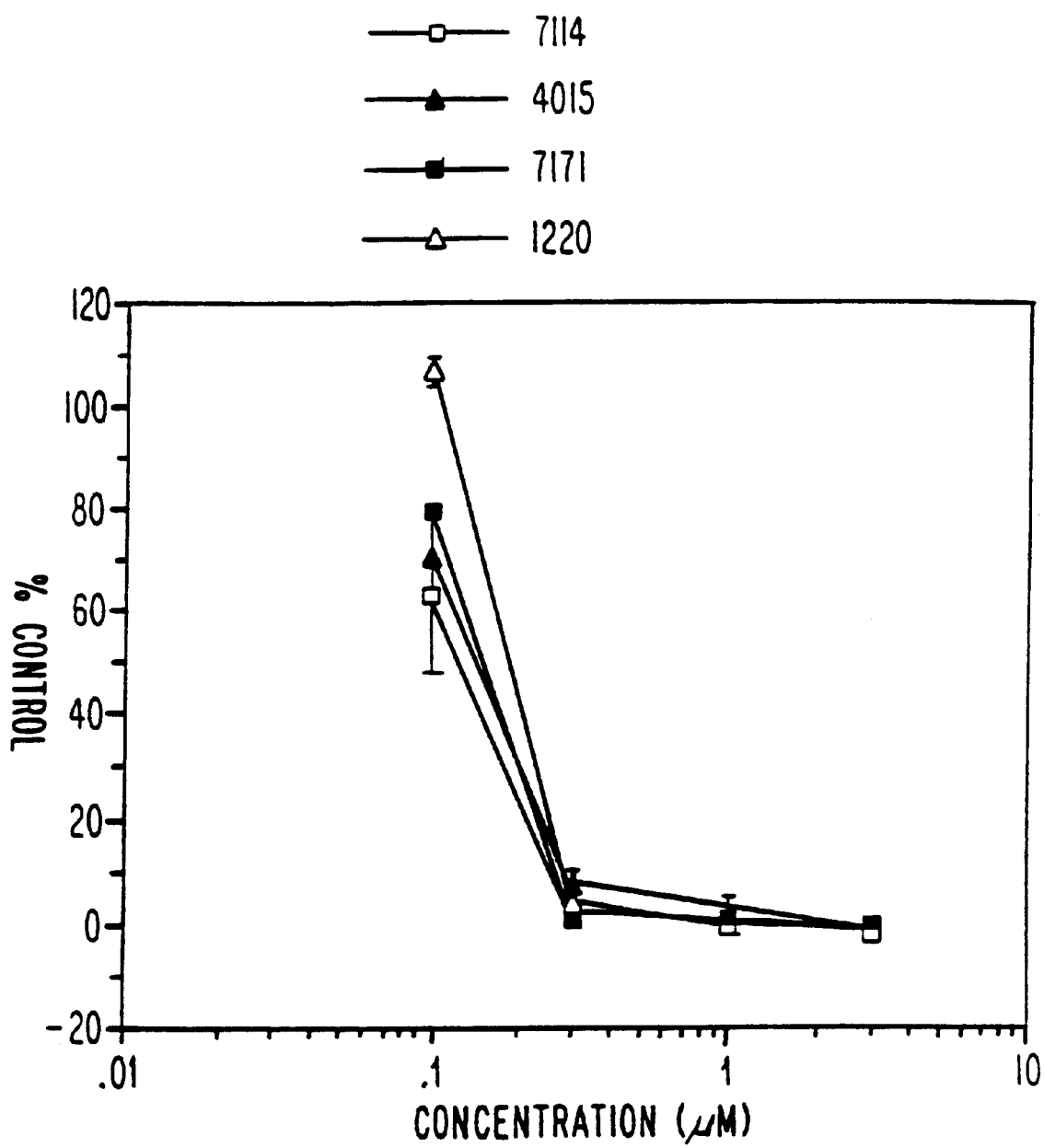
FIG. 8 is a line graph showing activity of ISIS 4015 and 2'-O-propyl gapped phosphorothioate oligonucleotides against HSV-1.
Figure 9:
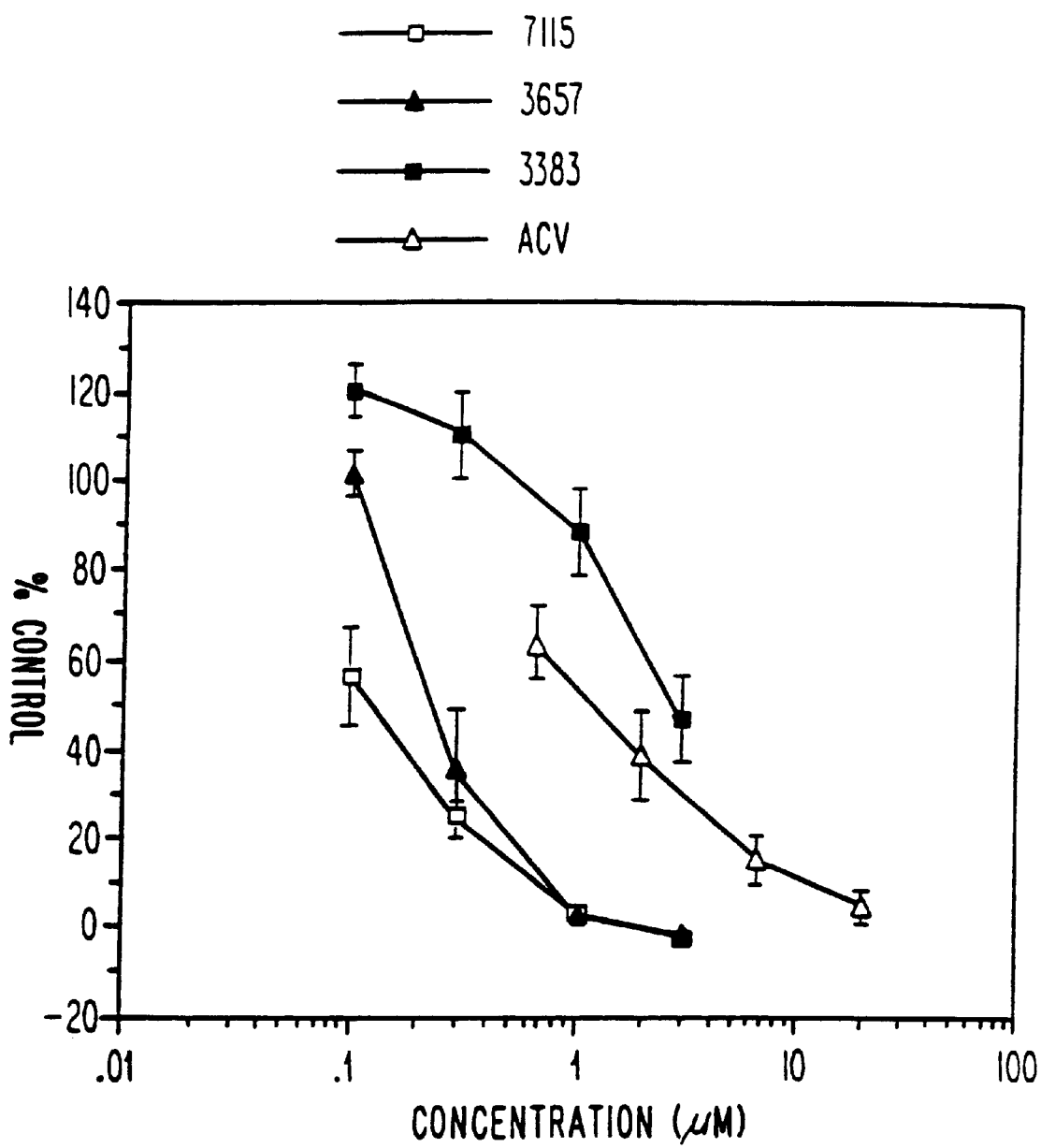
FIG. 9 is a line graph showing activity of ISIS 3657 and 2'-O-propyl phosphorothioate oligonucleotides against HSV-1.

Additional oligonucleotides were synthesized with 2'-O-propyl modifications. 2'-O-propyl oligonucleotides were prepared from 2'-deoxy-2'-O-propyl ribosides of nucleic acid bases A, G, U(T), and C which were prepared by modifications of literature procedures described by B. S. Sproat, et al., *Nucleic Acids Research* 18:41–49 (1990) and H. Inoue, et al., *Nucleic Acids Research* 15:6131–6148 (1987). ISIS 7114 is a phosphorothioate which has the same sequence (SEQ ID NO: 21) as ISIS 4015, and has a 2'-O-propyl modification on each sugar. ISIS 7171 is a phosphorothioate gapped 2'-O-propyl oligonucleotide with the same sequence as ISIS 4015 and 2'-O-propyl modifications at positions 1–7 and 14–20 (6-deoxy gap). As shown in FIG. 8, all three oligonucleotides are active against HSV. A uniform 2'-O-propyl phosphorothioate version of ISIS 3657 (SEQ ID NO: 16) was also synthesized and tested for activity against HSV-1. As shown in FIG. 9, this oligonucleotide (ISIS 7115) was even more active than ISIS 3657. 2'-O-propyl modifications are therefore a preferred embodiment of this invention. FIG. 9 also shows that both ISIS 3657 and ISIS 7115 are several-fold more active than Acyclovir, which in turn is more active than a control oligonucleotide, ISIS 3383.

Example 16

Effect of Chemical Modification on Inhibition of HSV-1 by G4 Oligonucleotides

Inosine Substitutions

A series of oligonucleotides were prepared in which one or more guanosines were replaced with an inosine residue. Oligonucleotides containing inosine residues were synthesized as for unmodified DNA oligonucleotides, using inosine phosphoramidites purchased from Glen Research. These sequences were assayed for activity in ELISA assays as described in Example 3. These oligonucleotides, their parent sequences and EC50 values are shown in Table 12.

TABLE 12

Activity of inosine-substituted oligonucleotides against HSV

| Oligo # | Sequence | Target | Type | EC50 (μM) | SEQ ID NO: |
|---|---|---|---|---|---|
| 1220 | CAC GAA AGG CAT GAC CGG GGC | UL9, AUG | Parent | 0.24, 0.16 | 1 |
| 5297 | CAC GAA AGG CAT GAC CGI GGC | " | Inosine #18 | >3.0 | 135 |
| 5308 | CAC GAA AGG CAT GAC CGG GIC | " | Inosine #20 | >3.0 | 136 |
| 4015 | GTT GGA GAC CGG GGT TGG GG | UL29, 5'UTR | Parent | 0.22, 0.22 | 21 |
| 4925 | GTT GGA GAC CGG IGT TGG IG | " | Inosine #13, 19 | 1.60 | 137 |
| 5295 | GTT GGA GAC CGG GIT TGG GG | " | Inosine #14 | >3.0 | 138 |
| 5296 | GTT GGA GAC CGG GGT TGG IG | " | Inosine #19 | 0.80 | 139 |
| 5309 | GTT GGA GAC CGI GGT TGG GG | " | Inosine #12 | >3.0 | 140 |
| 5310 | GTT GGA GAC CGG GGT TGG GI | " | Inosine #20 | 0.40 | 141 |

In this assay, oligonucleotides with EC50s of 1 μM or less were judged to be particularly active and are preferred.

Fluorescein-Conjugated Oligonucleotides

Several oligonucleotides were synthesized with a fluorescein moiety conjugated to the 5' end of the oligonucleotide. Fluorescein-conjugated oligonucleotides were synthesized using fluorescein-labeled amidites purchased from Glen Research. These sequences were assayed for activity in ELISA assays as described in Example 3. These oligonucleotides, their parent sequences and EC50 values are shown in Table 13. In this assay, oligonucleotides with EC50s of 1 μM or less were judged to be particularly active and are preferred.

TABLE 13

Activity of fluorescein-conjugated oligonucleotides against HSV

| Oligo # | Sequence | Target | Type | EC50 ($\mu$M) | SEQ ID NO: |
|---|---|---|---|---|---|
| 1220 | CAC GAA AGG CAT GAC CGG GGC | UL9, AUG | Parent | 0.24, 0.16 | 1 |
| 5338 | CAC GAA AGG CAT GAC CGG GGC | " | Fluorescein | 0.16 | 1 |
| 3657 | CAT CGC CGA TGC GGG GCG ATC | IE175, AUG | Parent | 0.20 | 16 |
| 5340 | CAT CGC CGA TGC GGG GCG ATC | " | Fluorescein | 0.18 | 16 |
| 4398 | CAC GGG GTC GCC GAT GAA CC | UL29, 5'UTR | Parent | 0.10 | 28 |
| 5324 | CAC GGG GTC GCC GAT GAA CC | " | Fluorescein | 0.16 | 28 |
| 1082 | GCC GAG GTC CAT GTC GTA CGC | UL13, AUG | Parent | 2.50, 1.80 | 134 |
| 5339 | GCC GAG GTC CAT GTC GTA CGC | " | Fluorescein | 0.65 | 134 |

7-Methyl-7-deaza Guanosine Substitutions

Monomer Preparation

A starred suspension of 0.8 g (20 mmole) of a 60% sodium hydride in hexane dispersion was decanted and taken to dryness, resuspended in 100 ml of dry acetonitrile and the suspension treated with 3.21 g (15 mmole) of 4-chloro-5-methyl-2-methylthiopyrrolo[2,3-d]pyrimidine [Kondo et al. (1977) Agric. Biol. Chem. 4:1501–1507]. The mixture was stirred under nitrogen at room temperature for one hour and then treated with 5.9 g (15 mmole) of 1-chloro-2-deoxy-3,5-di-O-(p-toluoyl)-$\alpha$-D-erythropentofuranose added in portions. An additional 40 ml of acetonitrile was added, the mixture stirred at 50° C. for about three and one half hours and then filtered and the solid washed with acetonitrile and dried to give 6.1 g (72%) of 4-chloro-5-methyl-2-methylthio-7-[$\alpha$-D-erythro-pentofuranosyl] pyrrolo[2,3-d]pyrimidine, m.p. 163–163.5° C.

Reaction of this product with sodium 2-propenyloxide in DMF afforded 5-methyl-2-methylthio-4-(2-propenyloxy)-7-[$\alpha$-D-erythro-pentofuranosyl]pyrrolo[2,3-d]pyrimidine, which on oxidation with two molar equivalents of 3-chloroperbenzoic acid in methylene chloride, afforded 5-methyl-2-methylsulfonyl-4-(2-propenyloxy-7-($\alpha$-D-erythro-pentofuranosyl)pyrrolo [2, 3-d]pyrimidine. Reaction of the product with hydrazine afforded 5-methyl-2-hydrazino-4-(2-propenyloxy)-7-($\alpha$-D-erythropentofuranosyl)pyrrolo[2,3-d]pyrimidine. Reduction of the product with, for example, Raney nickel affords 7-deaza-2'-deoxy-7-methylguanosine.

Protection of Monomer

The latter is treated sequentially first with trimethylchlorosilane in the presence of pyridine, then with isobutyric hydroxide to give 2-isobutyryl-7-deaza-2'-deoxy-7-methylguanosie, which, on reaction with one molar equivalent of trityl chloride in the presence of dry pyridine, affords 2-isobutyryl-7-deaza-2'-deoxy-7-methyl-5'tritylguanosine. Reaction of the latter with one molar equivalent of chloro-$\beta$-cyanoethoxy-N,N-diisopropylaminophosphine affords 2-isobutyryl-7-2'-deoxy-7-methyl-3'-O-[N,N-diiospropylamino-$\beta$-cyanoethoxyphosphanyl]-5'-tritylguanosine. This protected monomer is then incorporated into oligonucleotides during automated synthesis.

An oligonucleotide having the same sequence as ISIS 3657 was synthesized in which the guanosines at positions 14 and 15 were replaced with 7-methyl-7-deaza guanosines. This oligonucleotide (ISIS 6303) was found to have an IC50 of approximately 10 $\mu$M.

Example 17

Activity of ISIS 4015 in Combination with Other Antiviral Drugs

Figure 10:
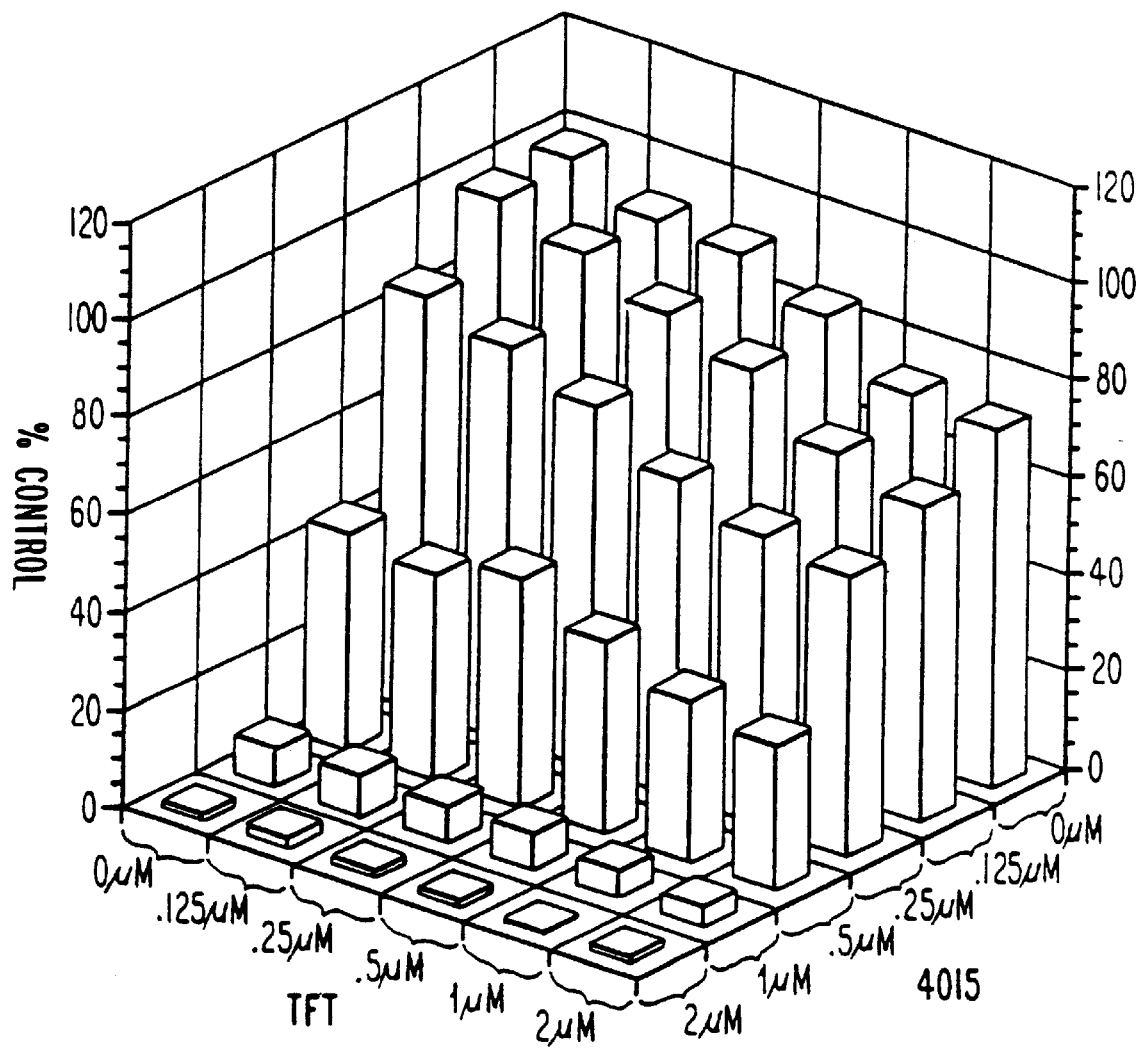
FIG. 10 is a three-dimensional bar graph showing effects on HSV-1 of ISIS 4015 and TFT separately and in combination.

ISIS 4015 was tested in combination with the nucleoside analog 5-trifluoromethyl-dUrd (TFT) in the ELISA assay described in Example 3. oligonucleotide and TFT concentrations from 0 to 2 $\mu$M were tested. As shown in FIG. 10, ISIS 4015 appears to enhance the activity of TFT against HSV-1.

Figure 11:
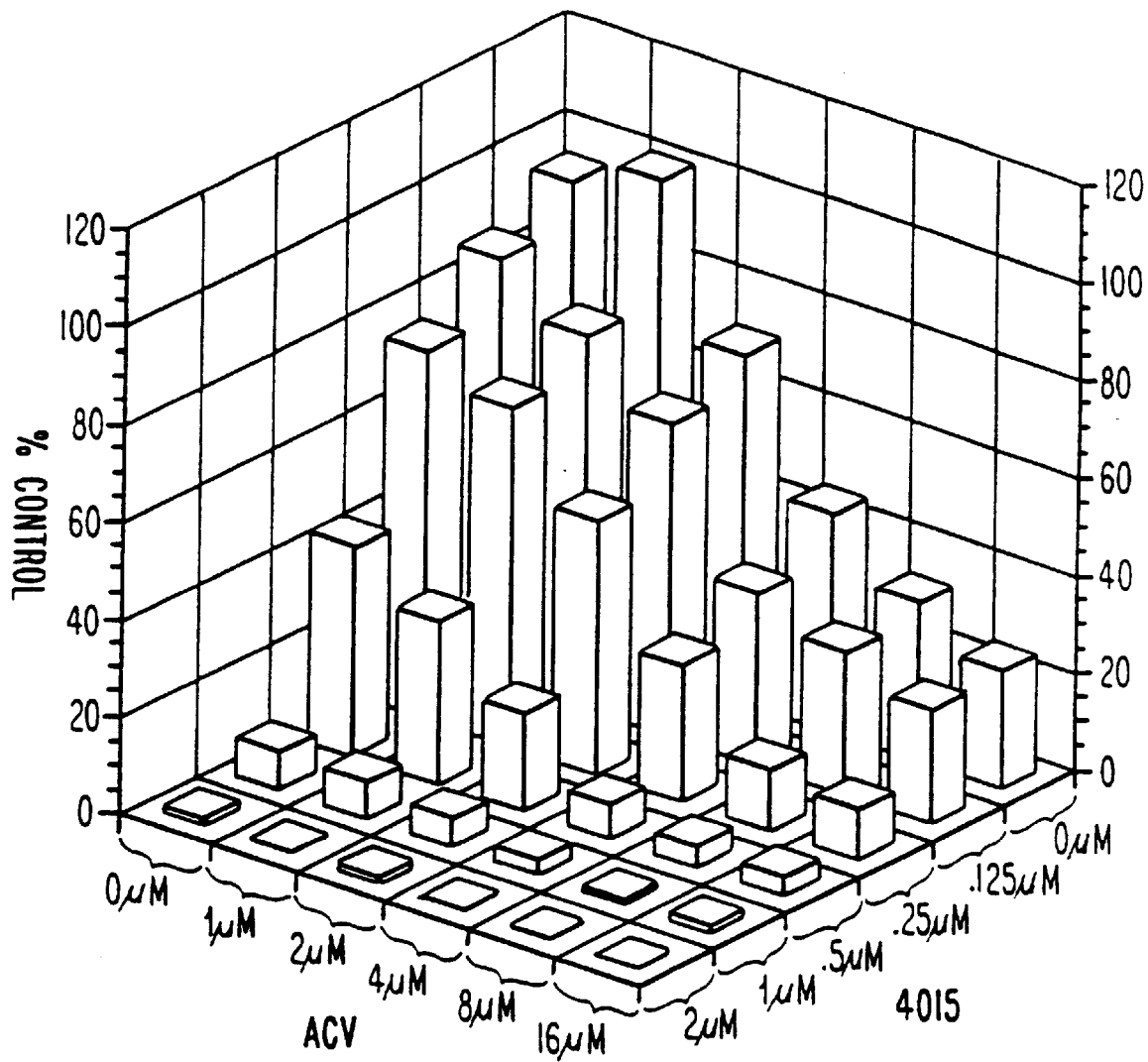
FIG. 11 is a three-dimensional bar graph showing effects on HSV-1 of ISIS 4015 and ACV separately and in combination.

ISIS 4015 was tested in the same way against 9-(2-hydroxyethoxymethyl) guanine (Acyclovir, ACV), at oligonucleotide concentrations of 0 to 2 $\mu$M and ACV concentrations from 0 to 16 $\mu$M. As shown in FIG. 11, the effect of the two drugs in combination appeared to be additive.

Example 18

Activity of $G_4$-Containing 8-Mer Oligonucleotides against HSV-1

A progressive unrandomization strategy [Ecker, D. J. et al., (1993) Nucl. Acids. Res. 21:1853–1956] was used to identify an 8-mer phosphorothioate oligonucleotide which was active against HSV-1 in the ELISA assay described in Example 3. The "winning" oligonucleotide, ISIS 5684, had the sequence GGGGGGTG. The ED50 of this oligonucleotide was found to be approximately 0.6 $\mu$M.

A series of 8-mer phosphorothioate oligonucleotides containing a $G_4$ sequence were synthesized and tested in the HSV-1 ELISA assay described in Example 3. These oligonucleotides are shown in Table 14.

TABLE 14

Anti-HSV Activity of short $G_4$-containing Oligonucleotides

| ISIS NO. | SEQUENCE |
|---|---|
| 5060 | GTGGGGA |
| 6170 | GTGGGGTG |
| 5684 | GGGGGGTG |
| 5058 | GCGGGGTA |

Figure 12:
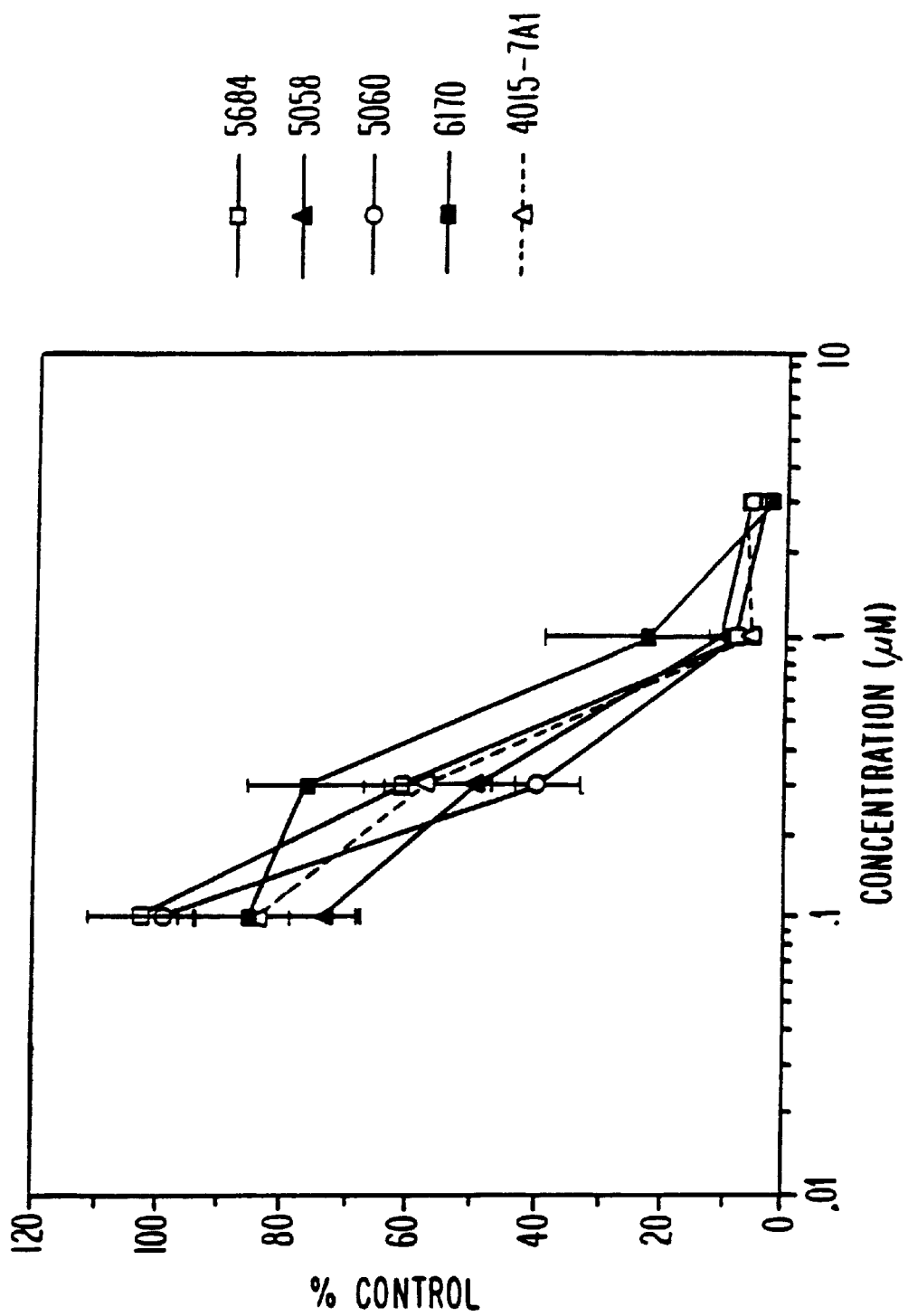
FIG. 12 is a line graph showing antiviral activity of G-string oligonucleotides 5684, 5058, 5060, 6170 and 4015.

As shown in FIG. 12, all of these oligonucleotides have IC50's below 1 $\mu$M and are therefore preferred. Several of these 8-mers have anti-HSV activity greater than that of ISIS 4015, a 20-mer.

G. Oligonucleotides Active against HIV

Example 19

Oligonucleotide Library Synthesis

Phosphorothioate oligonucleotides were synthesized using standard protocols. Sulfurization was achieved using 3H-1,2-benzodithiole-3-one-1,1 dioxide ("Beaucage reagent") as oxidizing agent. Iyer, R. P., Phillips, L. R., Egan, W., Regan, J. B. & Beaucage, S. L. (1990) *J. Org. Chem.* 55, 4693–4699. For oligonucleotides with randomized positions, amidites were mixed in a single vial on the fifth port of the ABI 394 synthesizer.

The mixture was tested by coupling to dT-CPG, cleaving and deprotecting the product, and analyzing the crude material on reversed-phase HPLC. Proportions of the individual amidites were adjusted until equal amounts of the four dimers were obtained. DMT-off oligonucleotides were purified by reversed-phase HPLC with a gradient of methanol in water to desalt and remove the protecting groups. Several purified oligonucleotides were analyzed for base composition by total digestion with nuclease followed by reversed-phase HPLC analysis and yielded expected ratios of each base.

Oligonucleotides with the α-configuration of the glycosidic bond were synthesized as previously described. Morvan, F., Rayner, B., Imbach, J-L., Thenet: S., Bertrand, J-R., Paoletti, J., Malvy, C. & Paoletti, C. (1993) *Nucleic Acids Res.* 15, 3421–3437. Biotin was incorporated during chemical synthesis using biotin-linked CPG from Glen Research. Oligonucleotide $T_2G_4T_2$ (ISIS 5320) was purified by reverse phase chromatography to remove salts and protecting groups and then by size exclusion chromatography to purify the tetramer as described in Example 21.

Prior to antiviral screening, oligonucleotides were diluted to 1 mM strand concentration in 40 mM sodium phosphate (pH 7.2), 100 mM KCl and incubated at room temperature overnight. Extinction coefficients were determined as described by Puglisi & Tinoco, (1989) In *Methods in Enzymolgy, RNA Processing*, eds. Dahlberg, J. E. & Abelson, J. N. (Academic Press, Inc., New York), Vol. 180, pp. 304–324. Samples were filtered through 0.2 μm cellulose acetate filters to sterilize.

Example 20

Acute HIV-1 Assay

Oligonucleotides were screened in an acute HIV-1 infection assay which measures protection from HIV-induced cytopathic effects. The CEM-SS cell line; Nara, P. L. & Fischinger, P. J. (1988) *Nature* 332, 469–470; was maintained in RPMI 1640 medium supplemented with 10% fetal bovine serum, 2 mM glutamine, penicillin (100 units mL$^{-1}$), and streptomycin (100 μg mL$^{-1}$). The antiviral assay, using XTT-tetrazolium to quantitate drug-induced protection from HIV-induced cell killing has been described. White, E. L., Buckheit, Jr., R. W., Ross, L. J., Germany, J. M., Andries, K., Pauwels, R., Janssen, P. A. J., Shannon, W. M. & Chirigos, M. A. (1991) *Antiviral Res.* 16, 257–266.

Example 21

Characterization of Tetramer

Monomeric and tetrameric forms of oligonucleotides were separated on a Pharmacia Superdex HR 10/30 size exclusion column (Pharmacia, Upsalla, Sweden). Running buffer was 25 mM sodium phosphate (pH 7.2), 0.2 mM EDTA. Flow rate was 0.5 mL min$^{-1}$ and detection was at 260 nm. Monomer and tetramer peaks were integrated and fraction tetramer determined. For purification, a Pharmacia Superdex 75 HiLoad 26/60 column was used with a buffer of 10 mM sodium phosphate (pH 7.2) at a flow rate of 2 mL min$^{-1}$.

Dissociation of the tetramer was followed after dilution. A 1 mM solution of oligonucleotide was diluted to 10 μM into PBS (137 mM NaCl; 2.7 mM KCl; 1.5 mM potassium phosphate, monobasic; 8 mM sodium phosphate, dibasic) and incubated at 37° C. Phosphorothioate oligonucleotides having the sequence $T_2G_4T_2$ in K$^+$ and the phosphodiester $T_2G_4T_2$ were diluted from solutions in 40 mM sodium phosphate (pH 7.2), 100 mM KCl. Oligonucleotide having the sequence $T_2G_4T_2$ in Na$^+$ was diluted from a solution in 40 mM sodium phosphate (pH 7.2), 100 mM NaCl. Dissociation as a function of time was followed by size exclusion chromatography.

The tetramer formed was parallel-stranded as determined by analysis of the complexes formed by the phosphorothioate oligonucleotides having $T_2G_4T_2$ and $^{5'}T_3G_4T_4^{3'}$ (SEQ ID NO: 142). Each oligonucleotide was labeled at the 5' end with $^{32}$P. Each sample contained 125 μM unlabeled and 15 pM radioactively labeled amounts of one or both of the oligonucleotides. The samples were heated in 50 mM sodium phosphate (pH 7.2), 200 mM KCl in a boiling water bath for 15 min then incubated for 48 h at 4° C. Samples were analyzed by autoradiography of a 20% non-denaturing polyacrylamide (19:1, acrylamide:bis) gel run at 4° C. in 1×TBE running buffer.

Example 22

Assay of HIV-Induced Cell Fusion

Stochiometric amounts of chronically HIV-1-infected Hut 78 cells (Hut/4-3) and CD4+ HeLa cells harboring an LTR-driven lac z gene were co-cultured for 20 h in the presence or absence of oligonucleotide. Cells were fixed (1% formaldehyde, 0.2% glutaraldehyde in PBS) and incubated with X-gal until cell-associated color developed. After buffer removal, a standard o-nitrophenyl-β-D-galactopyranoside was used to quantitate β-galactosidase expression. As a control, HeLa CD4+ cells containing the LTR-driven lac Z gene were transfected using the calcium phosphate method with 30 μg of proviral DNA (pNL 4-3). Oligonucleotide was added immediately after the glycerol shock. Cells were fixed 48 h after transfection and assayed as described above.

Example 23

Binding of ISIS 5320 to gp120

Direct binding to gp120 was assayed using immobilized gp120 from a CD4 capture ELISA kit (American Biotechnologies). Biotinylated oligonucleotides (biotinylated during synthesis using biotin-linked CPG from Glen Research) were incubated in a volume of 100 μL with immobilized gp120. Following a 1 hour incubation wells were washed and 200 μL of streptavidin-alkaline phosphatase (Gibco BRL) diluted 1:1000 in PBS added to each well. After a 1 hour incubation at room temperature wells were washed and PNPP substrate (Pierce) added. Plates were incubated at 37° C. and absorbance at 405 nm was measured using a Titertek Multiscan MCC/340 ELISA plate reader.

Ability of ISIS 5320 to compete with dextran sulfate for binding to gp120 was determined. Biotinylated ISIS 5320 at a concentration of 0.5 μM was added to plates containing immobilized gp120 along with dextran sulfate at the indicated concentrations (Sigma, M.W. 5000). Following a 1 h incubation, the amount of oligonucleotide associated with gp120 was determined as described above.

The site of ISIS 5320 binding to gp120 was determined by competition for binding of antisera specific for various regions of the protein. Rusche, J. R., et al., (1987) *Proc. Natl. Acad. Sci.* USA 84, 6924–6928; Matsushita, S., et al., (1988) *J. Virol.* 62, 2107–2114; Meuller, W. T., et al., (1986) *Science* 234, 1392–1395. gp120-coated microtiter plates were incubated with oligonucleotide at a concentration of 25 μM for 1 h at room temperature. Antisera was added at a dilution of 1:250 and the plates incubated 40 min. The plates were washed four times with PBS and amount of antibody bound quantitated by incubating with protein A/G-alkaline phosphatase (1:5000, Pierce) in PBS for 1 h at room temperature. After one wash with PBS, substrate was added and absorbance at 405 nm was measured.

Binding of ISIS 5320 to gp120, CD44 and CD4 expressed on cells was quantitated. HeLa cells harboring an HIV-1 env c gene; Gama Sosa, M. A., et al., (1989) *Biochem. Biophys. Res. Comm.* 161, 305–311 and Ruprecht, R. M., et al., (1991) *J. Acquir. Immune Defic. Syndr.* 4, 48–55; were cultured in DMEM supplemented with 10% FCS and 100 μg μL$^{-1}$ G-418. Extent of binding to gp120 was detected using 1 μg of FITC-conjugated murine anti-gp120 HIV-1 IIIB mAb IgG (Agmed). CD44 binding was detected using 1 μg of FITC-conjugated murine anti-CD44 mAb IgG (Becton-Dickinson). Each experiment consisted of 200,000 cells. Cells were washed once in culture media with 0.05% NaN$_3$ then resuspended in 100 μL of media containing oligonucleotide and incubated 15 min at room temperature. Antibody was added and the incubation continued for 1 h at 4° C. The cells were washed twice with PBS and immunofluorescence was measured on a Becton-Dickinson FACScan. Mean fluorescence intensity was determined using Lysis$^{II}$ software.

CEM-T4 cells; Foley, G. E., et al., (1965) *Cancer* 18, 522–529; were maintained in MEM supplemented with 10% FCS. Extent of binding to CD4 was determined using 1 μg of Q425, a murine anti-CD4 mAb IgG. Healey, D., et al., (1990) *J. Exp. Med.* 172, 1233–1242. Cells were harvested and washed and incubated with oligonucleotide as above. After a 30 min incubation at room temperature with antibody, the cells were washed and incubated with 100 μL of media containing 5 μg of goat F (ab')$_2$ anti-mouse IgG (Pierce). The cells were incubated 30 min, washed and associated fluorescence determined as above.

Example 24

Selection and Characterization of T$_2$G$_4$T$_2$

A phosphorothioate oligonucleotide library containing all possible sequences of eight nucleotides divided into 16 sets, each consisting of 4,096 sequences, was prepared as described in Example 19 and screened for inhibition of HIV infection as described in Example 21. Results are summarized in Table 15.

TABLE 15

| Combinatorial Pools | X=A | X=G | X=C | X=T |
|---|---|---|---|---|
| Round 1 | | | | |
| NNA NXN NN | inactive | inactive | inactive | inactive |
| NNG NXN NN | inactive | 19.5 (5%) | inactive | inactive |
| NNC NXN NN | inactive | inactive (0%) | inactive | inactive |
| NNT NXN NN | inactive | inactive | inactive (0%) | inactive |
| Round 2 | | | | |
| NNG XGN NN | 60.7 | 1.8 | 55.6 | 56.2 |

TABLE 15-continued

| Combinatorial Pools | X=A | X=G | X=C | X=T |
|---|---|---|---|---|
| | | (36%) | | (3%*) |
| Round 3 | | | | |
| NNG GGX NN | 8.0 | 0.5 (94%) | 3.1 (19%*) | 8.6 |
| Round 4 | | | | |
| NAG GGG XN | 0.5 | 0.5 | 0.5 | 0.5 (87%) |
| NGG GGG XN | 0.5 | 0.6 (99%*) | 0.4 | 0.5 |
| NCG GGG XN | 0.7 | 0.6 | 0.5 | 0.4 (91%) |
| NTG GGG XN | 0.4 (82%) | 0.5 | 0.4 | 0.5 |
| Round 5 | | | | |
| XTG GGG TN | 0.4 (94%) | 0.5 (89%*) | 0.4 | 0.5 (94%) |
| Round 6 | | | | |
| TTGGGGTX | 0.6 (90%) | 0.6 | 0.5 | 0.3 (93%) |

Random positions, N, are an equimolar mixture of each base. Antiviral data are reported as the quantity of drug (in μM of oligonucleotide strand) required to inhibit 50% of virus-induced cell killing (IC$_{50}$). Error in the IC$_{50}$ is ±0.1 μM. "Inactive" pools showed no antiviral activity at 100 μM strand concentration. The % tetramer, determined as described in Example 21, is given in parentheses for selected pools. An asterisk indicates multiple aggregate species.

The in vitro assay measured protection of cells from HIV-induced cytopathic effects. White, E. L., et al., (1991) *Antiviral Res.* 16, 257–266. In the initial rounds of selection, antiviral activity was observed only in the set containing guanosine in two fixed positions. Subsequent rounds of selection showed that four consecutive Gs provided maximum antiviral activity. No strong selection preference was observed for nucleotides flanking the guanosine core. The sequence T$_2$G$_4$T$_2$ (oligonucleotide ISIS 5320) was chosen for further study. The concentration of ISIS 5320 required for 50% inhibition of virus-induced cell killing (IC$_{50}$) was 0.3 μM. The antiviral activity of this oligonucleotide was not a result of inhibition of cell metabolism; cytotoxic effects were not observed until cells were incubated with approximately 100 μM ISIS 5320.

Although the oligonucleotide ISIS 5320 has a phosphorothioate backbone, evidence suggests that it adopts a four-stranded, parallel helix as do phosphodiester oligonucleotides of similar sequence. Cheong, C. & Moore, P. B. (1992) *Biochemistry* 31, 8406–8414; Aboul-ela, F., et al., (1992) *Nature* 360, 280–282; Sarma, M. H., et al., (1992) *J. Biomol. Str. Dyn.* 9, 1131–1153; and Wang, Y. & Patel, D. J. (1992) *Biochemistry* 31, 8112–8119. The oligonucleotides in the combinatorial library pools that show antiviral activity (Table 15) and oligonucleotide ISIS 5320 form multimeric complexes as shown by size exclusion chromatography (FIG. 13). The retention time of the complex was that expected for a tetrameric species based on plots of retention time vs. log molecular weight of phosphorothioate oligonucleotide standards (data not shown). The circular dichroism (CD) spectrum of the multimeric form of oligonucleotide ISIS 5320 is characterized by a peak at 265 nm and a trough at 242 nm (data not shown), similar to the spectra reported by others for deoxyoligonucleotide tetramers.

Figure 14:
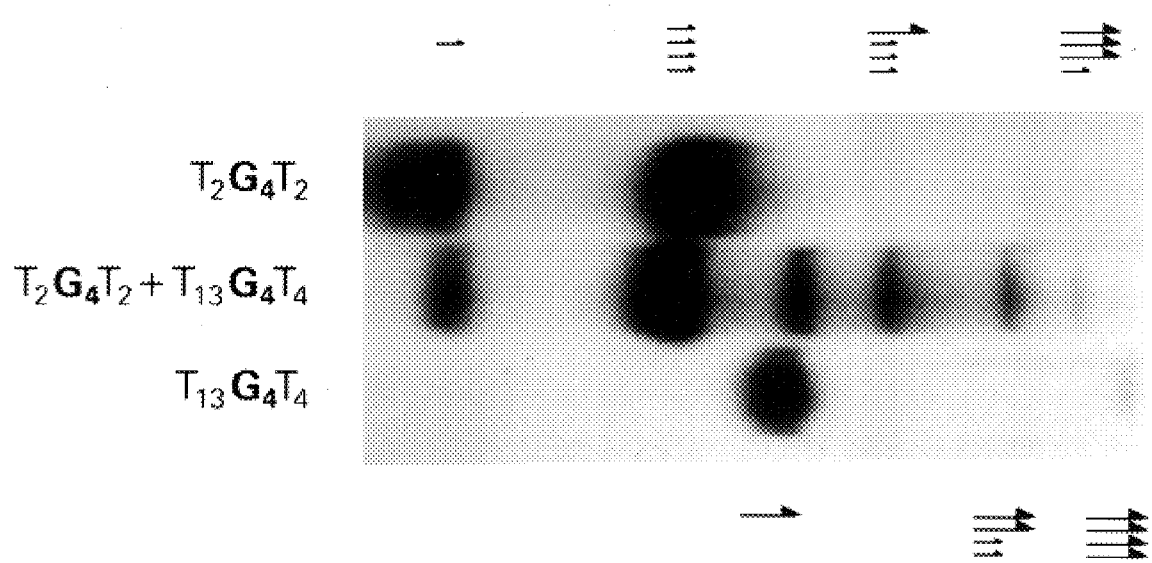
FIG. 14 is an autoradiogram of a gel electrophoresis experiment showing a pattern characteristic of a parallel-stranded tetramer. Lane 1: ISIS 5320 ($T_2G_4T_2$) alone. Lane 2: ISIS 5320 incubated with $T_{13}G_4G_4$ SEQ ID NO:146. Lane 3. $T_{13}G_4T_4$ SEQ ID NO:142 alone.

Sarma, M. H., et al., (1992) *J. Biomol. Str. Dyn.* 9, 1131–1153; Lu, M., Guo, Q. & Kallenbach, N. R. (1992) *Biochemistry* 31, 2455–2459; Jin, R., et al., (1992) *Proc. Natl. Acad. Sci.* USA 89, 8832–8836 and Hardin, C. C., et al., (1992) *Biochemistry* 31, 833–841. It has been reported that when two phosphodiester oligonucleotides of dissimilar size, but each containing four or five guanosines in a row, are incubated together, five distinct aggregate species are formed on a non-denaturing gel. Sen, D. & Gilbert, W. (1990) *Nature* 344, 410–414 and Kim, J., Cheong, C. & Moore, P. B. (1991) *Nature* 351, 331–332. In principle, only a tetramer of parallel strands can explain this pattern. When this experiment was performed with two phosphorothioate oligonucleotides, the antiviral oligonucleotide ISIS 5320 and a 21-residue oligonucleotide containing 4 guanosines near the 3' end ($^{5'}T_{13}G_4T_4^{3'}$), the five aggregate species expected for a parallel-stranded tetramer were observed on a non-denaturing gel (FIG. 14).

Example 25

The Tetramer is Active against HIV

Figure 15:
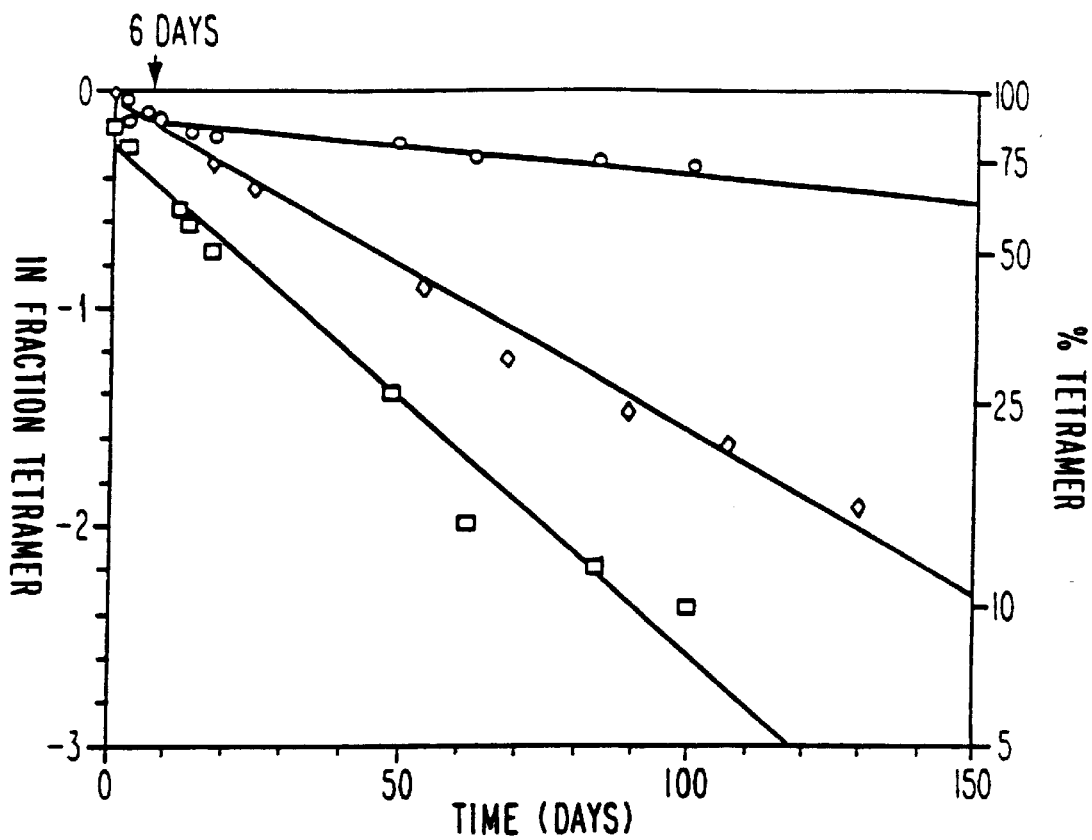
FIG. 15 is a line graph showing dissociation of tetramers formed by phosphorothioate ISIS 5320 in Na+ (squares), ISIS 5320 in K+ (diamonds) and the phosphodiester version (circles) over a period of days.

Oligonucleotides were screened for antiviral activity as described in Example 22. Samples of ISIS 5320 were diluted from a 1 mM stock solution that was at least 98% tetramer. Results showed that the tetramer is stable indefinitely at 1 mM strand concentration; no decrease in tetramer was observed over 5 months in a 1 mM sample in buffer containing 100 mM KCl at room temperature. Upon dilution to concentrations used in antiviral assays (less than 25 $\mu$M) dissociation of the tetramer begins; however, kinetics of the dissociation are very slow (FIG. 15). Slow kinetics for association and dissociation of intermolecular G-quartet complexes have been reported. Jin, R., et al., (1992) *Proc. Natl. Acad. Sci.* USA 89, 8832–8836 and Sen, D. & Gilbert, W. (1990) *Nature* 344, 410–414. The half life for the dissociation of the potassium form of ISIS 5320 is about 45 days. During the six-day period of the acute antiviral assay, at least 70% of the sample remained in the tetramer form whether the sample was prepared in sodium or potassium. Both sodium and potassium forms have the same $IC_{50}$ values in the acute antiviral assay, even though potassium preferentially stabilized the tetramer.

Heat denaturation of the tetrameric complex formed by ISIS 5320 before addition to the antiviral assay resulted in loss of activity; antiviral activity was recovered upon renaturation (data not shown). The striking difference in antiviral activity among the initial 16 sets of oligonucleotides used for combinatorial screening can be explained by the presence or absence of the G-core and therefore the tetramer structure (Table 15). In the intial round of screening, approximately 12% of the molecules in the active $^{5'}$NNG-NGNNN$^{3'}$ pool contained at least four sequential Gs, and size exclusion chromatography showed that 5% of the oligonucleotides formed tetramers (Table 15). In contrast, in the other three round 1 pools where X=G only 0.4% of the molecules contained at least four sequential Gs and no tetramer was observed. In other pools, there were no molecules with four consecutive Gs.

Deletion of nucleotides from either end of the ISIS 5320 sequence resulted in a loss of activity (Table 16).

TABLE 16

| Sequence | $IC_{50}$ ($\mu$M) | % tetramer |
|---|---|---|
| $T_sT_sG_sG_sG_sG_sT_sT$ | 0.3 | 98 |
| $T_sT_sG_sG_sG_sG_sT_sT$ heat denatured | inactive | 0 |
| $G_sG_sG_sG_sT_sT$ | 0.5 | 94* |
| $G_sG_sG_sG_sT$ | 1.4 | 61* |
| $G_sG_sG_sG$ | 4 | 29* |
| $T_sT_sG_sG_sG_sG$ | 13 | 40* |
| $T_sG_sG_sG_sG$ | inactive | 57* |
| $T_sG_sT_sG_sT_sG_sT_sG$ | inactive | 0 |
| $\alpha$-$T_sT_sG_sG_sG_sG_sT_sT$ | 0.5 | 98 |
| $\alpha$-$T_oT_oG_oG_oG_oG_oT_oT$ | inactive | 97 |
| $T_oT_oG_oG_oG_oG_oT_oT$ | inactive | 93 |
| $T_sT_sG_sG_sG_sT_sT$ | 5.0 | 80 |
| $T_oT_oG_sG_sG_sG_oT_oT$ | inactive | 72 |
| $T_sT_sG_oG_sG_sG_sT_sT$ | inactive | 9 |
| $T_sT_oG_sG_oG_sG_oT_sT$ | 5.3 | 83 |
| $T_sT_sG_sG_sG_sG_sT_sT_sB$ | 0.4 | 85 |

Data from the acute HIV assay for sequence variants and analogs of ISIS 5320. Chemical modifications of the oligonucleotide are indicated: "s" phosphorothioate backbone, "o" phosphodiester backbone, "$\alpha$", $\alpha$-configuration of the glycosidic bond; "B" biotin (incorporated during chemical synthesis using biotin linked CPG from Glen Research). "Inactive" indicates no activity at 25 $\mu$M concentration. The % tetramer was determined as described in Example 21. An asterisk indicates more than one aggregate species.

The phosphorothioate GGGG shows some activity; two nucleotides on the 3' side of the four Gs were required for nearly optimal activity. More than one multimeric species was observed by size exclusion chromatography for oligonucleotides with the G-core exposed.

The sequence $T_2G_4T_2$ with a phosphodiester backbone was inactive in the anti-HIV assay, even though the phosphodiester tetramer appears to be kinetically more stable than that formed by the phosphorothioate ISIS 5320 (FIG. 15). While not wishing to be bound to a particular theory, two hypotheses are proposed. The phosphorothioate backbone may be mechanistically required or the modified backbone may prevent nuclease-mediated degradation of the oligonucleotide.

Oligonucleotide analogs with the glycosidic bond oriented in the $\alpha$-position are resistant to nuclease degradation. Morvan, F., et al., (1993) *Nucleic Acids Res.* 15, 3421–3437. Based on size exclusion chromatography it has been shown that both the phosphorothioate $\alpha$-oligonucleotide and the phosphodiester $\alpha$-oligonucleotide formed tetramers however, only the phosphorothioate analog was active against HIV (Table 16). Assay of oligonucleotides with mixed phosphorothioate-phosphodiester backbones showed that phosphorothioate linkages at the termini, but not within the G-core, are necessary for activity. Results are shown in Table 16.

Example 26

Tetramer Inhibits HIV-1 Binding or Fusion to CD4$^+$ Cells

The oligonucleotide ISIS 5320 had no effect on chronically infected (H9 IIIB) cell models (data not shown) that respond only to inhibitors that work at post-integration steps. In a high multiplicity of infection (MOI) experiment performed as described in Srivastava, K. K., et al., (1991) *J. Virol.* 65, 3900–3902, ISIS 5320 inhibited production of intracellular PCR-amplifiable DNA (data not shown), which indicated that the compound inhibited an early step of HIV replication, such as binding, fusion, internalization, or reverse transcription.

The tetramer form of ISIS 5320 also inhibited binding or fusion of infectious virus to a CD4+ cell. The assay was performed as described in Example 22. HeLa-CD4-LTR-B-gal cells; Kimpton, J. & Emerman, M. (1992) J. Virol. 66, 2232–2239; were incubated for 15 minutes with oligonucleotide at 37° C. prior to the addition of virus. After 1 hour, the cells were washed to remove unbound virus and oligonucleotide. During the incubation period, virus binding and membrane fusion events occur. Srivastava, K. K., et al., (1991) J. Virol. 65, 3900–3902. Extent of infection after 48 hours was determined by quantitation of syncytia and ELISA as previously described in Kimpton, J. & Emerman, M. (1992) J. Virol. 66, 2232–2239. At a ISIS 5320 concentration of approximately 0.4 $\mu$M, virus production was reduced to 50% of control (data not shown). Heat-denatured ISIS 5320 and $5'$TGTGTGTG$^{3'}$ showed inhibition of binding at 5 $\mu$M oligonucleotide concentration. These fusion and binding inhibition experiments strongly suggest that the tetramer form of ISIS 5320 inhibits viral infection at a very early step, either during binding of the virion to the cell or during the early events of fusion and internalization of the virion.

Example 27

Tetramer Binds to the V3 Domain of gp120

Figure 16:
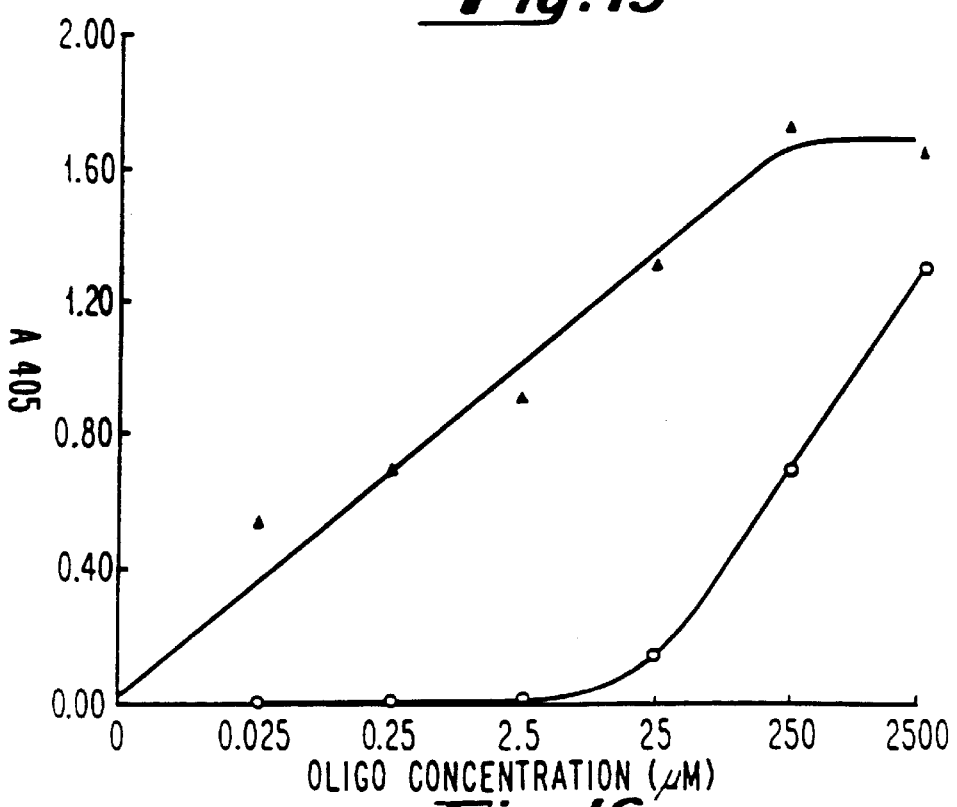
FIG. 16 is a line graph showing binding of ISIS 5320 to gp120, measured by absorbance at 405 nm.

Cellular experiments indicated that ISIS 5320 blocks viral binding or fusion, therefore, the affinities of the ISIS 5320 tetramer for CD4 and gp120 were determined as described in Example 23. Biotinylated ISIS 5320 (Table 16) bound to immobilized gp120 with a dissociation constant ($K_d$) of less than 1 $\mu$M (FIG. 16). In contrast, a control phosphorothioate, $5'T_2A_4T_2$-biotin$^{3'}$, bound weakly to gp120 with an estimated $K_d$ of 260 $\mu$M. Addition of CD4 at concentrations of up to 50 $\mu$g mL$^{-1}$ had no effect on ISIS 5320 binding to gp120 (data not shown). Similar experiments using CD4-coated microtiter plates showed that biotinylated ISIS 5320 also associates with CD4; however, the $K_d$ of approximately 25 $\mu$M was considerably weaker than to gp120. The control bound CD4 only when it was added at very high concentrations ($K_d$ approximately 240 $\mu$M). In addition, qualitative gel shift assays performed as described in Fried, M. & Crothers, D. M. (1981) Nucleic Acids Res. 9, 6505–6525, were performed to determine the affinity of ISIS 5320 for other HIV proteins (Tat, p24, reverse transcriptase, vif, protease, gp41), soluble CD4 (sCD4) and non-related proteins (BSA, transferrin and RNase $V_1$). Both monomeric and tetrameric forms of ISIS 5320 bound to BSA and reverse transcriptase. Tetramer-specific binding was observed only to gp120 and sCD4.

Figure 17:
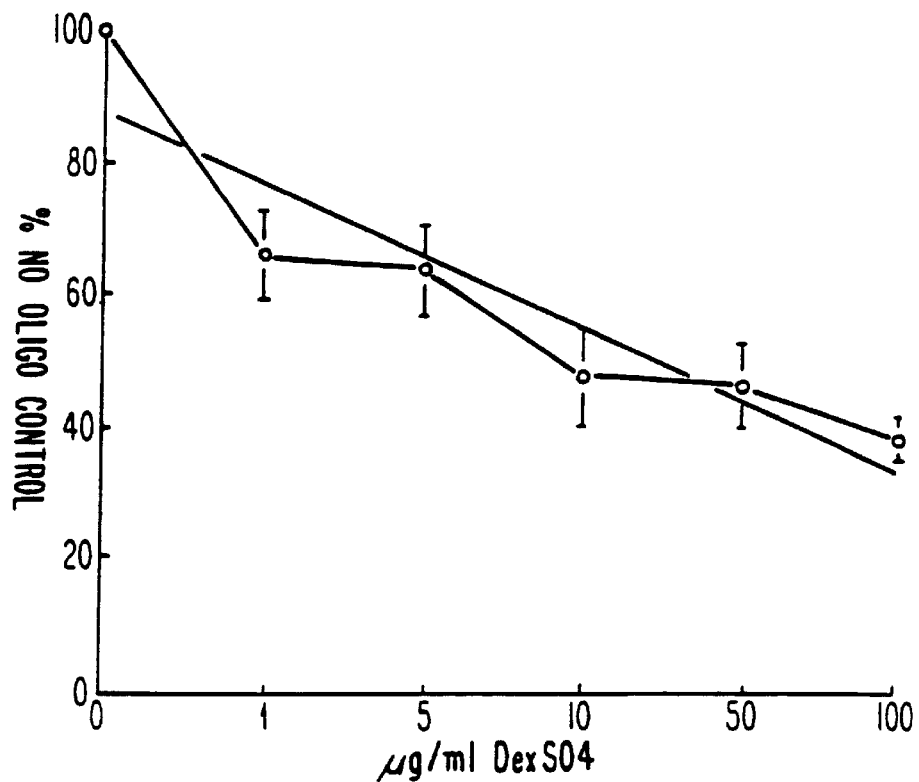
FIG. 17 is a line graph showing that dextran sulfate is a competitive inhibitor of binding of biotinylated ISIS 5320 to gp120.

The V3 loop of gp120 (amino acids 303–338) is considered the principal neutralizing domain of the protein; peptides derived from this region elicit type-specific neutralizing antibodies that block viral infection by blocking fusion. (1992) Human Retroviruses and AIDS 1992, eds. Myers, G. et al. (Theoretical Biology and Biophysics, Los Alamos National Laboratory, Los Alamos, N.M.). The V3 loop of gp120 is also the site of action of anionic polysaccharides, such as dextran sulfate, that inhibit viral binding, replication and syncytium formation. Callahan, L., et al., (1991) J. Virol. 65, 1543–1550. Dextran sulfate is a competitive inhibitor of binding of biotinylated ISIS 5320 to gp120 immobilized on a microtiter plate. About 50% of the tetramer binding was inhibited at a dextran sulfate concentration between 10 and 50 $\mu$g mL$^{-1}$ (FIG. 17). Dextran sulfate has been shown to inhibit binding of gp120-specific antibodies to gp120 in this concentration range. Callahan, L., et al., (1991) J. Virol. 65, 1543–1550.

The oligonucleotide ISIS 5320 also interferes with binding of antisera directed against the V3 loop region of gp120, but not to antisera specific for another region of the protein. Rusche, J. R., et al., (1987) Proc. Natl. Acad. Sci. USA 84, 6924–6928; Matsushita, S., et al., (1988) J. Virol. 62, 2107–2114 and Meuller, W. T., et al., (1986) Science 234, 1392–1395. The control oligonucleotide had no effect on antibody binding.

Figure 18:
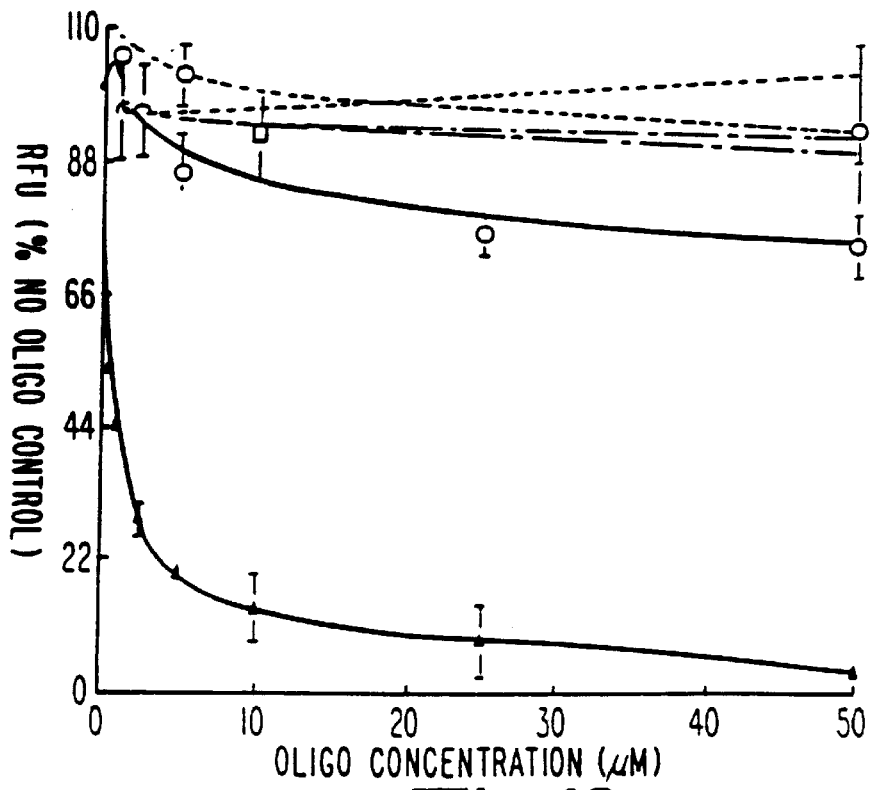
FIG. 18 is a line graph showing that ISIS 5320 blocks binding of an antibody specific for the V3 loop of gp120 (solid line) but not antibodies specific for CD44 (even dashes) or CD4 (uneven dashes), as determined by immunofluorescent flow cytometry.

The tetramer also binds to the V3 loop of gp120 expressed on cells. Binding of a monoclonal antibody specific for the V3 loop of gp120 was inhibited by ISIS 5320 at a concentration of approximately 0.5 $\mu$M ($K_1$) determined using immunofluorescent flow cytometry (FIG. 18). The control oligonucleotide had little effect on binding at concentrations up to 50 $\mu$M. Neither oligonucleotide significantly decreased binding of antibodies directed to human CD44 on the same cells or to CD4; Healey, D., et al., (1990) J. Exp. Med. 172, 1233–1242. on CEM-T4 cells.

Phosphorothioate oligonucleotides of at least 15 nucleotides are known to be non-sequence-specific inhibitors of HIV. Stein, C. A., et al., (1991) J. Acquir. Immune Defic. Syndr. 4, 686–693. In the acute assay system used here, previously tested phosphorothioate oligonucleotides of 18 to 28 nucleotides in length have IC$_{50}$ values between 0.2 and 4 $\mu$M. Vickers, T., et al., (1991) Nucleic Acids Res. 19, 3359–3368. Stein and co-workers have shown that phosphorothioate oligonucleotides of at least 18 nucleotides in length, bind to the V3 loop of gp120 (40), and to the CD4 receptor and other cell surface antigens. Stein, C. A., et al., (1991) J. Acquir. Immune Defic. Syndr. 4, 686–693. Variation in the binding and antiviral activities of long mixed seqence oligonucleotides likely result from folding into unknown structures with varying affinities for membrane surface proteins. In contrast, ISIS 5320 adopts a defined tetrameric structure. The antiviral activity is 2- to 25-fold better, on a weight basis, than that of longer linear oligonucleotides.

ELISA assays were performed to determine whether ISIS 5320 was capable of blocking the interaction between CD4 and gp120 (data not shown). Addition of increasing amounts of ISIS 5320 decreased binding of CD4 to immobilized gp120; 50% of binding was inhibited at a concentration of approximately 2.5 $\mu$M. The control oligonucleotide ($5'$TGTGTGTG$^{3'}$) had no effect on the CD4/gp120 interaction. These results were confirmed in a gp120-capture ELISA assay in which the microtiter plates were coated with CD4 (IC$_{50}$ approximately 20 $\mu$M). Compounds that bind to the V3 loop of gp120 can inhibit fusion without completely blocking the interaction between CD4 and gp120. Callahan, L., et al., (1991) J. Virol. 65, 1543–1550. Unlike ISIS 5320, dextran sulfate does not prevent the gp120/CD4 interaction in an ELISA assay even at concentrations 10,000-fold above its IC$_{50}$. Callahan, L., et al., (1991) J. Virol. 65, 1543–1550.

The tetrameric form of phosphorothioate $T_2G_4T_2$ blocks cell-to-cell and virion-to-cell spread of HIV infection by binding to the gp120 V3 loop. The tetramer provides a rigid, compact structure with a high thio-anionic charge density that may be the basis for its strong interaction with the cationic V3 loop. Although the V3 loop is a hypervariable region, the functional requirement for cationic residues in the V3 loop may limit the virus's capability to become resistant to dense polyanionic inhibitors. Compounds derived from the G-quartet structural motif are potential candidates for use in anti-HIV chemotherapy.

What is claimed is:

1. A chemically modified oligonucleotide having no more than about 27 nucleic acid base units, said oligonucleotide comprising at least one GGGG sequence or at least two GGG sequences and a sufficient number of flanking nucleotides to significantly inhibit the activity of a virus or phospholipase $A_2$.

2. The oligonucleotide of claim 1 wherein significant inhibition of viral or enzyme activity is at least 50% inhibition.

3. The oligonucleotide of claim 1 wherein the virus is human immunodeficiency virus, herpes simplex virus, human cytomegalovirus or influenza virus.

4. The oligonucleotide of claim 1 which has at least one phosphorothioate intersugar (backbone) linkage.

5. The oligonucleotide of claim 1 wherein each of the nucleotides is in the alpha ($\alpha$) anomeric configuration.

6. The oligonucleotide of claim 1 which is a chimeric oligonucleotide.

7. The oligonucleotide of claim 3 wherein the virus is herpes simplex virus.

8. The oligonucleotide of claim 7 wherein the oligonucleotide is selected from the group consisting of: SEQ ID NO: 21, SEQ ID NO: 1, SEQ ID NO: 8, SEQ ID NO: 12, SEQ ID NO: 16, SEQ ID NO: 22, SEQ ID NO: 28, SEQ ID NO: 30, SEQ ID NO: 31, SEQ ID NO: 33, SEQ ID NO: 35, SEQ ID NO: 36, SEQ ID NO: 37, SEQ ID NO: 38, SEQ ID NO: 39, SEQ ID NO: 42, SEQ ID NO: 47, SEQ ID NO: 48 and SEQ ID NO: 50.

9. The oligonucleotide of claim 7 having a sequence shown in Table 8.

10. The oligonucleotide of claim 9 having a sequence selected from the group consisting of SEQ ID NO: 124, SEQ ID NO:126, SEQ ID NO: 127, SEQ ID NO: 128, SEQ ID NO: 129, SEQ ID NO: 130 and SEQ ID NO: 133.

11. A chemically modified oligonucleotide having the sequence $(N_X G_4 N_Y)_Q$ wherein X and Y are independently 1 to 8 and Q is 1 to 4, wherein said oligonucleotide significantly inhibits the activity of a virus or phospholipase $A_2$.

12. The oligonucleotide of claim 11 having the sequence NNGGGGNN.

13. The oligonucleotide of claim 12 which has at least one phosphorothioate intersugar linkage and which has the sequence GNGGGGTN.

14. A chemically modified oligonucleotide having the sequence $(G_4 N_X G_4)_Q$ wherein X is 1 to 8 and Q is 1 to 3, wherein said oligonucleotide significantly inhibits the activity of a virus or phospholipase $A_2$.

15. A chemically modified oligonucleotide having the sequence $(N_X G_{3-4})_Q N_X$ wherein X is 1 to 8 and Q is 1 to 6, wherein said oligonucleotide significantly inhibits the activity of a virus or phospholipase $A_2$.

16. A phosphorothioate oligonucleotide having SEQ ID NO: 21.

17. A phosphorothioate oligonucleotide having the sequence TTGGGGTT.

18. The oligonucleotide of claim 17 wherein each of the nucleotides of the oligonucleotide is in the alpha ($\alpha$) anomeric configuration.

19. A compound comprising a G-quartet structure of phosphorothioate oligonucleotides each oligonucleotide having the sequence TxG4Ty, wherein x is 2 and y is 2, or x is 0 and y is 2, or x is 3 and v is 3.

20. The compound of claim 19 wherein the nucleotides of at least one of the oligonucleotides of the G-quartet structure are in the alpha ($\alpha$) anomeric configuration.

21. The compound of claim 19 wherein x is 2 and y is 2.

22. The compound of claim 19 wherein x is 0 and y is 2.

23. The compound of claim 19 wherein x is 3 and y is 3.

24. A chemically modified oligonucleotide having no more than about 27 nucleic acid base units, said oligonucleotide comprising at least two GGG sequences and a sufficient number of flanking nucleotides to modulate the telomere length of a chromosome.

25. The oligonucleotide of claim 24 which has at least one phosphorothioate intersugar linkage.

26. The oligonucleotide of claim 24 wherein each of the nucleotides is in the alpha ($\alpha$) anomeric configuration.

27. The oligonucleotide of claim 24 which is a chimeric oligonucleotide.

* * * * *

UNITED STATES PATENT AND TRADEMARK OFFICE
CERTIFICATE OF CORRECTION

PATENT NO.   : 5,952,490
DATED        : September 14, 1999
INVENTOR(S)  : Hanecak et al.

It is certified that error appears in the above-identified patent and that said Letters Patent is hereby corrected as shown below:

Title page,
Item [56], OTHER PUBLICATIONS, please delete "Gorup" and insert therefor
-- Group --;

Column 3,
Line 50, please insert a new paragraph after the word "infections" and insert the word
-- Prior -- before the word "attempts" at the start of this new sentence;

Column 4,
Line 23, please delete "Production" and insert therefor -- production --;

Column 7,
Line 21, please delete "1µM" and insert therefor -- 10µM --;

Column 10,
Table 1, no. 3657, please delete "dGG" and insert therefor -- GGG --;

Column 11,
Table 1, no. 5544, please insert -- >3.0 -- under the (EC50µM) column;
Table 1, no. 5739, please insert -- 6 MER -- under the (LENGTH) column;
Table 1, no. 5596, please delete no. "5596" and insert therefor -- 3196 --;

Column 13,
Table 3, no. 5542, please delete "P=s" and insert therefor -- P=S --;
Table 3, no. 5544, please delete "P=s" and insert therefor -- P=S --;
Table 3, no. 4803, please delete the "13" under the "4803" and insert -- 13 --
after ">25," to read -- >25,13 --;
Table 3, no. 5666, please insert -- 5 -- after "16.7" to read -- 16.7,5 --;

Column 36,
Line 16, Table 15, please delete "(91%)" under "0.4(X=T)" and insert therefor
the -- (91%) -- on line 16, under "0.4 (X=C)";
Line 19, under Round 5, please delete "XTG GGG TN 0.4 0.5 0.4 0.5" and insert
therefor -- XTG GGG TN  0.2  0.6  0.3 (94%)  0.3 --;

Column 38,
Line 15, please delete "$T_sT_sG_oG_oG_sT_sT$" and insert therefor
-- $T_sT_sG_oG_oG_oG_sT_sT$ --;

UNITED STATES PATENT AND TRADEMARK OFFICE
CERTIFICATE OF CORRECTION

PATENT NO.    : 5,952,490
DATED         : September 14, 1999
INVENTOR(S)   : Hanecak et al.

It is certified that error appears in the above-identified patent and that said Letters Patent is hereby corrected as shown below:

Column 51,
SEQ. ID. NO. 31, please delete "CGGGGTCG" and insert therefor
-- CACGGGGTCG --;

Column 90,
Line 64, please delete "v" and insert therefor -- y --;

Signed and Sealed this

Twenty-fifth Day of February, 2003

JAMES E. ROGAN
*Director of the United States Patent and Trademark Office*

SEQUENCE LISTING (1) GENERAL INFORMATION:

(iii) NUMBER OF SEQUENCES: 146

(2) INFORMATION FOR SEQ ID NO: 1:

(i) SEQUENCE CHARACTERISTICS:
         (A) LENGTH: 21
         (B) TYPE: nucleic acid
         (C) STRANDEDNESS: single
         (D) TOPOLOGY: linear (xi) SEQUENCE DESCRIPTION: SEQ ID NO: 1:

CACGAAAGGC ATGACCGGGG C                                              21

(2) INFORMATION FOR SEQ ID NO: 2:

(i) SEQUENCE CHARACTERISTICS:
         (A) LENGTH: 18
         (B) TYPE: nucleic acid
         (C) STRANDEDNESS: single
         (D) TOPOLOGY: linear (xi) SEQUENCE DESCRIPTION: SEQ ID NO: 2:

GAAAGGCATG ACCGGGGC                                                  18

(2) INFORMATION FOR SEQ ID NO: 3:

(i) SEQUENCE CHARACTERISTICS:
         (A) LENGTH: 15
         (B) TYPE: nucleic acid
         (C) STRANDEDNESS: single
         (D) TOPOLOGY: linear (xi) SEQUENCE DESCRIPTION: SEQ ID NO: 3:

AGGCATGACC GGGGC                                                     15

(2) INFORMATION FOR SEQ ID NO: 4:

(i) SEQUENCE CHARACTERISTICS:
         (A) LENGTH: 12
         (B) TYPE: nucleic acid
         (C) STRANDEDNESS: single
         (D) TOPOLOGY: linear (xi) SEQUENCE DESCRIPTION: SEQ ID NO: 4:

CATGACCGGG GC                                                        12

(2) INFORMATION FOR SEQ ID NO: 5:

(i) SEQUENCE CHARACTERISTICS:
         (A) LENGTH: 19
         (B) TYPE: nucleic acid
         (C) STRANDEDNESS: single
         (D) TOPOLOGY: linear (xi) SEQUENCE DESCRIPTION: SEQ ID NO: 5:

CACGAAAGGC ATGACCGGG                                                 19

(2) INFORMATION FOR SEQ ID NO: 6:

(i) SEQUENCE CHARACTERISTICS:
         (A) LENGTH: 18
         (B) TYPE: nucleic acid
         (C) STRANDEDNESS: single
         (D) TOPOLOGY: linear (xi) SEQUENCE DESCRIPTION: SEQ ID NO: 6:

CACGAAAGGC ATGACCGG                                              18

(2) INFORMATION FOR SEQ ID NO: 7:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 7:

CACGAAAGGC ATGAC                                                 15

(2) INFORMATION FOR SEQ ID NO: 8:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 8:

CATGGCGGGA CTACGGGGGC C                                          21

(2) INFORMATION FOR SEQ ID NO: 9:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 9:

CATGGCGGGA CTACG                                                 15

(2) INFORMATION FOR SEQ ID NO: 10:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 10:

TGGCGGGACT ACGGGGGC                                              18

(2) INFORMATION FOR SEQ ID NO: 11:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 11:

GGCGGGACTA CGGGG                                                 15

(2) INFORMATION FOR SEQ ID NO: 12:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 12:

```
ACCGCCAGGG GAATCCGTCA T                                              21

(2) INFORMATION FOR SEQ ID NO: 13:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 13:

GCCAGGGGAA TCCGTCAT                                                  18

(2) INFORMATION FOR SEQ ID NO: 14:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 14:

AGGGGAATCC GTCAT                                                     15

(2) INFORMATION FOR SEQ ID NO: 15:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 15:

GCCAGGGGAA TCCGT                                                     15

(2) INFORMATION FOR SEQ ID NO: 16:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 16:

CATCGCCGAT GCGGGGCGAT C                                              21

(2) INFORMATION FOR SEQ ID NO: 17:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 17:

CATCGCCGAT GCGGGGCG                                                  18

(2) INFORMATION FOR SEQ ID NO: 18:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 18:

CATCGCCGAT CGGGG                                                     15
```

(2) INFORMATION FOR SEQ ID NO: 19:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 19:

CGCCGATGCG GGGCG                                      15

(2) INFORMATION FOR SEQ ID NO: 20:

(i) SEQUENCE CHARACTERISTICS:
        (A) LENGTH: 12
        (B) TYPE: nucleic acid
        (C) STRANDEDNESS: single
        (D) TOPOLOGY: linear (xi) SEQUENCE DESCRIPTION: SEQ ID NO: 20:

GCCGATGCGG GG                                        12

(2) INFORMATION FOR SEQ ID NO: 21:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO: 21:

GTTGGAGACC GGGGTTGGGG                              20

(2) INFORMATION FOR SEQ ID NO: 22:

(i) SEQUENCE CHARACTERISTICS:
        (A) LENGTH: 17
        (B) TYPE: nucleic acid
        (C) STRANDEDNESS: single
        (D) TOPOLOGY: linear (xi) SEQUENCE DESCRIPTION: SEQ ID NO: 22:

GGAGACCGGG GTTGGGG                                  17

(2) INFORMATION FOR SEQ ID NO: 23:

(i) SEQUENCE CHARACTERISTICS:
        (A) LENGTH: 16
        (B) TYPE: nucleic acid
        (C) STRANDEDNESS: single
        (D) TOPOLOGY: linear (xi) SEQUENCE DESCRIPTION: SEQ ID NO: 23:

GAGACCGGGG TTGGGG                                 16

(2) INFORMATION FOR SEQ ID NO: 24:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 24:

AGACCGGGGT TGGGG                                    15

(2) INFORMATION FOR SEQ ID NO: 25:

(i) SEQUENCE CHARACTERISTICS:
        (A) LENGTH: 11
        (B) TYPE: nucleic acid
        (C) STRANDEDNESS: single
        (D) TOPOLOGY: linear (xi) SEQUENCE DESCRIPTION: SEQ ID NO: 25:

CGGGGTTGGG G                                                          11

(2) INFORMATION FOR SEQ ID NO: 26:

(i) SEQUENCE CHARACTERISTICS:
        (A) LENGTH: 10
        (B) TYPE: nucleic acid
        (C) STRANDEDNESS: single
        (D) TOPOLOGY: linear (xi) SEQUENCE DESCRIPTION: SEQ ID NO: 26:

GGGGTTGGGG                                                            10

(2) INFORMATION FOR SEQ ID NO: 27:

(i) SEQUENCE CHARACTERISTICS:
        (A) LENGTH: 17
        (B) TYPE: nucleic acid
        (C) STRANDEDNESS: single
        (D) TOPOLOGY: linear (xi) SEQUENCE DESCRIPTION: SEQ ID NO: 27:

GTTGGAGACC GGGGTTG                                                    17

(2) INFORMATION FOR SEQ ID NO: 28:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO: 28:

CACGGGGTCG CCGATGAACC                                                 20

(2) INFORMATION FOR SEQ ID NO: 29:

(i) SEQUENCE CHARACTERISTICS:
        (A) LENGTH: 17
        (B) TYPE: nucleic acid
        (C) STRANDEDNESS: single
        (D) TOPOLOGY: linear (xi) SEQUENCE DESCRIPTION: SEQ ID NO: 29:

GGGGTCGCCG ATGAACC                                                    17

(2) INFORMATION FOR SEQ ID NO: 30:

(i) SEQUENCE CHARACTERISTICS:
        (A) LENGTH: 17
        (B) TYPE: nucleic acid
        (C) STRANDEDNESS: single
        (D) TOPOLOGY: linear (xi) SEQUENCE DESCRIPTION: SEQ ID NO: 30:

CACGGGGTCG CCGATGA                                                    17

(2) INFORMATION FOR SEQ ID NO: 31:

(i) SEQUENCE CHARACTERISTICS:
            (A) LENGTH: 15
            (B) TYPE: nucleic acid
            (C) STRANDEDNESS: single
            (D) TOPOLOGY: linear (xi) SEQUENCE DESCRIPTION: SEQ ID NO: 31:

CGGGGTCG CCGAT                                                                  15

(2) INFORMATION FOR SEQ ID NO: 32:

(i) SEQUENCE CHARACTERISTICS:
            (A) LENGTH: 10
            (B) TYPE: nucleic acid
            (C) STRANDEDNESS: single
            (D) TOPOLOGY: linear (xi) SEQUENCE DESCRIPTION: SEQ ID NO: 32:

CACGGGGTCG                                                                      10

(2) INFORMATION FOR SEQ ID NO: 33:

(i) SEQUENCE CHARACTERISTICS:
            (A) LENGTH: 25
            (B) TYPE: nucleic acid
            (C) STRANDEDNESS: single
            (D) TOPOLOGY: linear (xi) SEQUENCE DESCRIPTION: SEQ ID NO: 33:

TTGGGGTTGG GGTTGGGGTT GGGGG                                                     25

(2) INFORMATION FOR SEQ ID NO: 34:

(i) SEQUENCE CHARACTERISTICS:
            (A) LENGTH: 25
            (B) TYPE: nucleic acid
            (C) STRANDEDNESS: single
            (D) TOPOLOGY: linear (xi) SEQUENCE DESCRIPTION: SEQ ID NO: 34:

TTGGGGTTGG GGTTGGGGTT GGGGG                                                     25

(2) INFORMATION FOR SEQ ID NO: 35:

(i) SEQUENCE CHARACTERISTICS:
            (A) LENGTH: 24
            (B) TYPE: nucleic acid
            (C) STRANDEDNESS: single
            (D) TOPOLOGY: linear (xi) SEQUENCE DESCRIPTION: SEQ ID NO: 35:

TTGGGGTTGG GGTTGGGGTT GGGG                                                      24

(2) INFORMATION FOR SEQ ID NO: 36:

(i) SEQUENCE CHARACTERISTICS:
            (A) LENGTH: 22
            (B) TYPE: nucleic acid
            (C) STRANDEDNESS: single
            (D) TOPOLOGY: linear (xi) SEQUENCE DESCRIPTION: SEQ ID NO: 36:

GGGGTTGGGG TTGGGGTTGG GG                                                        22

(2) INFORMATION FOR SEQ ID NO: 37:

(i) SEQUENCE CHARACTERISTICS:
            (A) LENGTH: 20

(B) TYPE: nucleic acid
            (C) STRANDEDNESS: single
            (D) TOPOLOGY: linear (xi) SEQUENCE DESCRIPTION: SEQ ID NO: 37:

TTGGGGTTGG GGTTGGGGTT                                                    20

(2) INFORMATION FOR SEQ ID NO: 38:

(i) SEQUENCE CHARACTERISTICS:
            (A) LENGTH: 18
            (B) TYPE: nucleic acid
            (C) STRANDEDNESS: single
            (D) TOPOLOGY: linear (xi) SEQUENCE DESCRIPTION: SEQ ID NO: 38:

TTGGGGTTGG GGTTGGGG                                                      18

(2) INFORMATION FOR SEQ ID NO: 39:

(i) SEQUENCE CHARACTERISTICS:
            (A) LENGTH: 16
            (B) TYPE: nucleic acid
            (C) STRANDEDNESS: single
            (D) TOPOLOGY: linear (xi) SEQUENCE DESCRIPTION: SEQ ID NO: 39:

GGGGTTGGGG TTGGGG                                                        16

(2) INFORMATION FOR SEQ ID NO: 40:

(i) SEQUENCE CHARACTERISTICS:
            (A) LENGTH: 14
            (B) TYPE: nucleic acid
            (C) STRANDEDNESS: single
            (D) TOPOLOGY: linear (xi) SEQUENCE DESCRIPTION: SEQ ID NO: 40:

TTGGGGTTGG GGTT                                                          14

(2) INFORMATION FOR SEQ ID NO: 41:

(i) SEQUENCE CHARACTERISTICS:
            (A) LENGTH: 12
            (B) TYPE: nucleic acid
            (C) STRANDEDNESS: single
            (D) TOPOLOGY: linear (xi) SEQUENCE DESCRIPTION: SEQ ID NO: 41:

TTGGGGTTGG GG                                                            12

(2) INFORMATION FOR SEQ ID NO: 42:

(i) SEQUENCE CHARACTERISTICS:
            (A) LENGTH: 21
            (B) TYPE: nucleic acid
            (C) STRANDEDNESS: single
            (D) TOPOLOGY: linear (xi) SEQUENCE DESCRIPTION: SEQ ID NO: 42:

GGGGCGGGGC GGGGCGGGGC G                                                  21

(2) INFORMATION FOR SEQ ID NO: 43:

(i) SEQUENCE CHARACTERISTICS:
            (A) LENGTH: 24
            (B) TYPE: nucleic acid
            (C) STRANDEDNESS: single (D) TOPOLOGY: linear (xi) SEQUENCE DESCRIPTION: SEQ ID NO: 43:

TTGGGGTTGG GGTTGGGGTT GGGG                                              24

(2) INFORMATION FOR SEQ ID NO: 44:

(i) SEQUENCE CHARACTERISTICS:
        (A) LENGTH: 22
        (B) TYPE: nucleic acid
        (C) STRANDEDNESS: single
        (D) TOPOLOGY: linear (xi) SEQUENCE DESCRIPTION: SEQ ID NO: 44:

GGGGTTGGGG TTGGGGTTGG GG                                                22

(2) INFORMATION FOR SEQ ID NO: 45:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO: 45:

TTGGGGTTGG GGTTGGGGTT                                                   20

(2) INFORMATION FOR SEQ ID NO: 46:

(i) SEQUENCE CHARACTERISTICS:
        (A) LENGTH: 10
        (B) TYPE: nucleic acid
        (C) STRANDEDNESS: single
        (D) TOPOLOGY: linear (xi) SEQUENCE DESCRIPTION: SEQ ID NO: 46:

GGGGTTGGGG                                                              10

(2) INFORMATION FOR SEQ ID NO: 47:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 47:

GGGTGGGTAT AGAAGGGCTC C                                                 21

(2) INFORMATION FOR SEQ ID NO: 48:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 48:

GGGTGGGTAT AGAAGGGC                                                     18

(2) INFORMATION FOR SEQ ID NO: 49:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 49:

GGGTGGGTAT AGAAG                                                15

(2) INFORMATION FOR SEQ ID NO: 50:

(i) SEQUENCE CHARACTERISTICS:
        (A) LENGTH: 12
        (B) TYPE: nucleic acid
        (C) STRANDEDNESS: single
        (D) TOPOLOGY: linear (xi) SEQUENCE DESCRIPTION: SEQ ID NO: 50:

GGGTGGGTAT AG                                                   12

(2) INFORMATION FOR SEQ ID NO: 51:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 51:

TGGGTATAGA AGGGCTCC                                             18

(2) INFORMATION FOR SEQ ID NO: 52:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 52:

GTATAGAAGG GCTCC                                                15

(2) INFORMATION FOR SEQ ID NO: 53:

(i) SEQUENCE CHARACTERISTICS:
        (A) LENGTH: 12
        (B) TYPE: nucleic acid
        (C) STRANDEDNESS: single
        (D) TOPOLOGY: linear (xi) SEQUENCE DESCRIPTION: SEQ ID NO: 53:

TAGAAGGGCT CC                                                   12

(2) INFORMATION FOR SEQ ID NO: 54:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 54:

TTGGGGTTGG GGTTGGGG                                             18

(2) INFORMATION FOR SEQ ID NO: 55:

(i) SEQUENCE CHARACTERISTICS:
        (A) LENGTH: 16
        (B) TYPE: nucleic acid
        (C) STRANDEDNESS: single
        (D) TOPOLOGY: linear (xi) SEQUENCE DESCRIPTION: SEQ ID NO: 55:

```
GGGGTTGGGG TTGGGG                                                    16
```

(2) INFORMATION FOR SEQ ID NO: 56:

(i) SEQUENCE CHARACTERISTICS:
        (A) LENGTH: 14
        (B) TYPE: nucleic acid
        (C) STRANDEDNESS: single
        (D) TOPOLOGY: linear (xi) SEQUENCE DESCRIPTION: SEQ ID NO: 56:

```
TTGGGGTTGG GGTT                                                      14
```

(2) INFORMATION FOR SEQ ID NO: 57:

(i) SEQUENCE CHARACTERISTICS:
        (A) LENGTH: 12
        (B) TYPE: nucleic acid
        (C) STRANDEDNESS: single
        (D) TOPOLOGY: linear (xi) SEQUENCE DESCRIPTION: SEQ ID NO: 57:

```
TTGGGGTTGG GG                                                        12
```

(2) INFORMATION FOR SEQ ID NO: 58:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 58:

```
TCTGCCCCGG CCGTCGCTCC C                                              21
```

(2) INFORMATION FOR SEQ ID NO: 59:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 59:

```
CAGAGGACTC CAGAGTTGTA T                                              21
```

(2) INFORMATION FOR SEQ ID NO: 60:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 60:

```
TTCATGGTAA GAGTTCTTGG G                                              21
```

(2) INFORMATION FOR SEQ ID NO: 61:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 61:

```
CAAAGATCAT GATCACTGCC A                                              21
```

(2) INFORMATION FOR SEQ ID NO: 62:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 62:

TCCCATGGGC CTGCAGTAGG C                                            21

(2) INFORMATION FOR SEQ ID NO: 63:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 63:

GGAAGGTTTC CAGGGAAGAG G                                            21

(2) INFORMATION FOR SEQ ID NO: 64:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 64:

CCTGCAGTAG GCCTGGAAGG A                                            21

(2) INFORMATION FOR SEQ ID NO: 65:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 65:

GGGACTCAGC AACGAGGGGT G                                            21

(2) INFORMATION FOR SEQ ID NO: 66:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 66:

GTAGGGAGGG AGGGTATGAG A                                            21

(2) INFORMATION FOR SEQ ID NO: 67:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 67:

AAGGAACTTG GTTAGGGTAG G                                            21

(2) INFORMATION FOR SEQ ID NO: 68:

(i) SEQUENCE CHARACTERISTICS:
    (A) LENGTH: 21
    (B) TYPE: nucleic acid
    (C) STRANDEDNESS: single
    (D) TOPOLOGY: linear (xi) SEQUENCE DESCRIPTION: SEQ ID NO: 68:

TGGGTGAGGG ATGCTTTCTG C                    21

(2) INFORMATION FOR SEQ ID NO: 69:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 69:

CTGCCTGGCC TCTAGGATGG G                    21

(2) INFORMATION FOR SEQ ID NO: 70:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 70:

ATAGAAGGGC TCCTGCCTGG C                    21

(2) INFORMATION FOR SEQ ID NO: 71:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 71:

TCTCATTCTG GGTGGGTATA G                    21

(2) INFORMATION FOR SEQ ID NO: 72:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 72:

GCTGGAAATC TGCTGGATGT C                    21

(2) INFORMATION FOR SEQ ID NO: 73:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 73:

GTGGAGGAGA GCAGTAGAAG G                    21

(2) INFORMATION FOR SEQ ID NO: 74:

(i) SEQUENCE CHARACTERISTICS:

(A) LENGTH: 21
        (B) TYPE: nucleic acid
        (C) STRANDEDNESS: single
        (D) TOPOLOGY: linear (xi) SEQUENCE DESCRIPTION: SEQ ID NO: 74:

TGGTTAAGCA CGGAGTTGAG G                                              21

(2) INFORMATION FOR SEQ ID NO: 75:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 75:

CCGGAGTACA GCTTCTTTGG T                                              21

(2) INFORMATION FOR SEQ ID NO: 76:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 76:

TTGCTTTATT CAGAAGAGAC C                                              21

(2) INFORMATION FOR SEQ ID NO: 77:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 77:

TTTTTGATTT GCTAATTGCT T                                              21

(2) INFORMATION FOR SEQ ID NO: 78:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 78:

GGAGCCCTTC TATACCCACC C                                              21

(2) INFORMATION FOR SEQ ID NO: 79:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 79:

CACCCCTCGT TGCTGAGTCC C                                              21

(2) INFORMATION FOR SEQ ID NO: 80:

(i) SEQUENCE CHARACTERISTICS:
        (A) LENGTH: 21
        (B) TYPE: nucleic acid

```
        (C) STRANDEDNESS: single
        (D) TOPOLOGY: linear (xi) SEQUENCE DESCRIPTION: SEQ ID NO: 80:

TCTCATACCC TCCCTCCCTA C                                              21

(2) INFORMATION FOR SEQ ID NO: 81:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 81:

AGGTCGAGGA GTGGTCTGAG C                                              21

(2) INFORMATION FOR SEQ ID NO: 82:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 82:

CCAGGAGAGG TCGGTAAGGC G                                              21

(2) INFORMATION FOR SEQ ID NO: 83:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 83:

GTAGGGATGG GAGTGAAGGA G                                              21

(2) INFORMATION FOR SEQ ID NO: 84:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 84:

TGCTCCTCCT TGGTGGCTCT C                                              21

(2) INFORMATION FOR SEQ ID NO: 85:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 85:

CTCTGCTGGG TGGTCTCAAC T                                              21

(2) INFORMATION FOR SEQ ID NO: 86:

(i) SEQUENCE CHARACTERISTICS:
        (A) LENGTH: 21
        (B) TYPE: nucleic acid
        (C) STRANDEDNESS: single
        (D) TOPOLOGY: linear
```

(xi) SEQUENCE DESCRIPTION: SEQ ID NO: 86:

GGACTGGCCT AGCTCCTCTG C                                              21

(2) INFORMATION FOR SEQ ID NO: 87:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 87:

GGTGACAAAT GCAGATGGAC T                                              21

(2) INFORMATION FOR SEQ ID NO: 88:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 88:

TAGGAGGGTC TTCATGGTAA G                                              21

(2) INFORMATION FOR SEQ ID NO: 89:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 89:

AGCTCTTACC AAAGATCATG A                                              21

(2) INFORMATION FOR SEQ ID NO: 90:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 90:

AGTAGGCCTG GAAGGAAATT T                                              21

(2) INFORMATION FOR SEQ ID NO: 91:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 91:

TGGCCTCACC GATCCGTTGC A                                              21

(2) INFORMATION FOR SEQ ID NO: 92:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 92:

```
ACAGCAGCTG TGAGGAGACA C                                              21

(2) INFORMATION FOR SEQ ID NO: 93:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 93:

ACTCTTACCA CAGGTGATTC T                                              21

(2) INFORMATION FOR SEQ ID NO: 94:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 94:

AGGAGTCCTG TTTTGAAATC A                                              21

(2) INFORMATION FOR SEQ ID NO: 95:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 95:

AGTGCACGTT GAGTATGTGA G                                              21

(2) INFORMATION FOR SEQ ID NO: 96:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 96:

CTACGGCAGA GACGAGATAG C                                              21

(2) INFORMATION FOR SEQ ID NO: 97:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 97:

GGGTGGGTAT AGAAGGGC                                                  18

(2) INFORMATION FOR SEQ ID NO: 98:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 98:

GGGTGGGTAT AGAAG                                                     15
```

(2) INFORMATION FOR SEQ ID NO: 99:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 99:

TGGGTATAGA AGGGCTCC                                                      18

(2) INFORMATION FOR SEQ ID NO: 100:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 100:

GTATAGAAGG GCTCC                                                         15

(2) INFORMATION FOR SEQ ID NO: 101:

(i) SEQUENCE CHARACTERISTICS:
        (A) LENGTH: 12
        (B) TYPE: nucleic acid
        (C) STRANDEDNESS: single
        (D) TOPOLOGY: linear (xi) SEQUENCE DESCRIPTION: SEQ ID NO: 101:

TAGAAGGGCT CC                                                            12

(2) INFORMATION FOR SEQ ID NO: 102:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 102:

TGGGTATAGA AGGGC                                                         15

(2) INFORMATION FOR SEQ ID NO: 103:

(i) SEQUENCE CHARACTERISTICS:
        (A) LENGTH: 12
        (B) TYPE: nucleic acid
        (C) STRANDEDNESS: single
        (D) TOPOLOGY: linear (xi) SEQUENCE DESCRIPTION: SEQ ID NO: 103:

AGGTGGGTAT AG                                                            12

(2) INFORMATION FOR SEQ ID NO: 104:

(i) SEQUENCE CHARACTERISTICS:
        (A) LENGTH: 12
        (B) TYPE: nucleic acid
        (C) STRANDEDNESS: single
        (D) TOPOLOGY: linear (xi) SEQUENCE DESCRIPTION: SEQ ID NO: 104:

GGGAGGGTAT AG                                                            12

(2) INFORMATION FOR SEQ ID NO: 105:

(i) SEQUENCE CHARACTERISTICS:
        (A) LENGTH: 12
        (B) TYPE: nucleic acid
        (C) STRANDEDNESS: single
        (D) TOPOLOGY: linear (xi) SEQUENCE DESCRIPTION: SEQ ID NO: 105:

GGGCGGGTAT AG                                    12

(2) INFORMATION FOR SEQ ID NO: 106:

(i) SEQUENCE CHARACTERISTICS:
        (A) LENGTH: 12
        (B) TYPE: nucleic acid
        (C) STRANDEDNESS: single
        (D) TOPOLOGY: linear (xi) SEQUENCE DESCRIPTION: SEQ ID NO: 106:

GGGTGGATAT AG                                    12

(2) INFORMATION FOR SEQ ID NO: 107:

(i) SEQUENCE CHARACTERISTICS:
        (A) LENGTH: 12
        (B) TYPE: nucleic acid
        (C) STRANDEDNESS: single
        (D) TOPOLOGY: linear (xi) SEQUENCE DESCRIPTION: SEQ ID NO: 107:

GGGTGGGAAT AG                                    12

(2) INFORMATION FOR SEQ ID NO: 108:

(i) SEQUENCE CHARACTERISTICS:
        (A) LENGTH: 10
        (B) TYPE: nucleic acid
        (C) STRANDEDNESS: single
        (D) TOPOLOGY: linear (xi) SEQUENCE DESCRIPTION: SEQ ID NO: 108:

GGGTGGGTAT                                        10

(2) INFORMATION FOR SEQ ID NO: 109:

(i) SEQUENCE CHARACTERISTICS:
        (A) LENGTH: 24
        (B) TYPE: nucleic acid
        (C) STRANDEDNESS: single
        (D) TOPOLOGY: linear (xi) SEQUENCE DESCRIPTION: SEQ ID NO: 109:

TTGGGGTTGG GGTTGGGGTT GGGG                        24

(2) INFORMATION FOR SEQ ID NO: 110:

(i) SEQUENCE CHARACTERISTICS:
        (A) LENGTH: 22
        (B) TYPE: nucleic acid
        (C) STRANDEDNESS: single
        (D) TOPOLOGY: linear (xi) SEQUENCE DESCRIPTION: SEQ ID NO: 110:

GGGGTTGGGG TTGGGGTTGG GG                          22

(2) INFORMATION FOR SEQ ID NO: 111:

(i) SEQUENCE CHARACTERISTICS:
    (A) LENGTH: 18
    (B) TYPE: nucleic acid
    (C) STRANDEDNESS: single
    (D) TOPOLOGY: linear (xi) SEQUENCE DESCRIPTION: SEQ ID NO: 111:

TTGGGGTTGG GGTTGGGG                                             18

(2) INFORMATION FOR SEQ ID NO: 112:

(i) SEQUENCE CHARACTERISTICS:
        (A) LENGTH: 16
        (B) TYPE: nucleic acid
        (C) STRANDEDNESS: single
        (D) TOPOLOGY: linear (xi) SEQUENCE DESCRIPTION: SEQ ID NO: 112:

GGGGTTGGGG TTGGGG                                               16

(2) INFORMATION FOR SEQ ID NO: 113:

(i) SEQUENCE CHARACTERISTICS:
        (A) LENGTH: 12
        (B) TYPE: nucleic acid
        (C) STRANDEDNESS: single
        (D) TOPOLOGY: linear (xi) SEQUENCE DESCRIPTION: SEQ ID NO: 113:

TTGGGGTTGG GG                                                   12

(2) INFORMATION FOR SEQ ID NO: 114:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO: 114:

TTGGGGTTGG GGTTGGGGTT                                           20

(2) INFORMATION FOR SEQ ID NO: 115:

(i) SEQUENCE CHARACTERISTICS:
        (A) LENGTH: 14
        (B) TYPE: nucleic acid
        (C) STRANDEDNESS: single
        (D) TOPOLOGY: linear (xi) SEQUENCE DESCRIPTION: SEQ ID NO: 115:

TTGGGGTTGG GGTT                                                 14

(2) INFORMATION FOR SEQ ID NO: 116:

(i) SEQUENCE CHARACTERISTICS:
        (A) LENGTH: 24
        (B) TYPE: nucleic acid
        (C) STRANDEDNESS: single
        (D) TOPOLOGY: linear (xi) SEQUENCE DESCRIPTION: SEQ ID NO: 116:

TTGGGGTTGG GGTTGGGGTT GGGG                                      24

(2) INFORMATION FOR SEQ ID NO: 117:

(i) SEQUENCE CHARACTERISTICS:
        (A) LENGTH: 22

```
        (B) TYPE: nucleic acid
        (C) STRANDEDNESS: single
        (D) TOPOLOGY: linear (xi) SEQUENCE DESCRIPTION: SEQ ID NO: 117:

GGGGTTGGGG TTGGGGTTGG GG                                            22

(2) INFORMATION FOR SEQ ID NO: 118:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO: 118:

TTGGGGTTGG GGTTGGGGTT                                               20

(2) INFORMATION FOR SEQ ID NO: 119:

(i) SEQUENCE CHARACTERISTICS:
        (A) LENGTH: 10
        (B) TYPE: nucleic acid
        (C) STRANDEDNESS: single
        (D) TOPOLOGY: linear (xi) SEQUENCE DESCRIPTION: SEQ ID NO: 119:

GGGGTTGGGG                                                          10

(2) INFORMATION FOR SEQ ID NO: 120:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 120:

GAGGCTGAGG TGGGAGGA                                                 18

(2) INFORMATION FOR SEQ ID NO: 121:

(i) SEQUENCE CHARACTERISTICS:
        (A) LENGTH: 39
        (B) TYPE: nucleic acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: N is A or C or G or T/U (ix) FEATURE:
        (A) NAME/KEY: Modified-site
        (B) LOCATION: 2
        (D) OTHER INFORMATION: N is A or C or G or T/U (ix) FEATURE:
        (A) NAME/KEY: Modified-site
        (B) LOCATION: 3
        (D) OTHER INFORMATION: N is A or C or G or T/U (xi) SEQUENCE DESCRIPTION: SEQ ID NO: 121:

NNNGGGGTTT TGGGGTTTTG GGGTTTTGGG GTTTTGGGG                           39

(2) INFORMATION FOR SEQ ID NO: 122:

(i) SEQUENCE CHARACTERISTICS:
        (A) LENGTH: 21
```

(B) TYPE: nucleic acid
            (C) STRANDEDNESS: single
            (D) TOPOLOGY: linear (xi) SEQUENCE DESCRIPTION: SEQ ID NO: 122:

TGGGCACGTG CCTGACACGG C                                          21

(2) INFORMATION FOR SEQ ID NO: 123:

(i) SEQUENCE CHARACTERISTICS:
            (A) LENGTH: 20
            (B) TYPE: nucleic acid
            (C) STRANDEDNESS: single
            (D) TOPOLOGY: linear (xi) SEQUENCE DESCRIPTION: SEQ ID NO: 123:

GAGGTGGGCT GTGGTGGTGA                                            20

(2) INFORMATION FOR SEQ ID NO: 124:

(i) SEQUENCE CHARACTERISTICS:
            (A) LENGTH: 20
            (B) TYPE: nucleic acid
            (C) STRANDEDNESS: single
            (D) TOPOLOGY: linear (xi) SEQUENCE DESCRIPTION: SEQ ID NO: 124:

GGGGTTGGGG AATGAATCCC                                            20

(2) INFORMATION FOR SEQ ID NO: 125:

(i) SEQUENCE CHARACTERISTICS:
            (A) LENGTH: 20
            (B) TYPE: nucleic acid
            (C) STRANDEDNESS: single
            (D) TOPOLOGY: linear (xi) SEQUENCE DESCRIPTION: SEQ ID NO: 125:

GGGTTGGAGA CCGGGGTTGG                                            20

(2) INFORMATION FOR SEQ ID NO: 126:

(i) SEQUENCE CHARACTERISTICS:
            (A) LENGTH: 20
            (B) TYPE: nucleic acid
            (C) STRANDEDNESS: single
            (D) TOPOLOGY: linear (xi) SEQUENCE DESCRIPTION: SEQ ID NO: 126:

GGTTGGAGAC CGGGGTTGGG                                            20

(2) INFORMATION FOR SEQ ID NO: 127:

(i) SEQUENCE CHARACTERISTICS:
            (A) LENGTH: 20
            (B) TYPE: nucleic acid
            (C) STRANDEDNESS: single
            (D) TOPOLOGY: linear (xi) SEQUENCE DESCRIPTION: SEQ ID NO: 127:

TGGAGACCGG GGTTGGGGAA                                            20

(2) INFORMATION FOR SEQ ID NO: 128:

(i) SEQUENCE CHARACTERISTICS:
            (A) LENGTH: 20
            (B) TYPE: nucleic acid
            (C) STRANDEDNESS: single (D) TOPOLOGY: linear (xi) SEQUENCE DESCRIPTION: SEQ ID NO: 128:

TTGGAGACCG GGGTTGGGGA                                               20

(2) INFORMATION FOR SEQ ID NO: 129:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 129:

GACGGTCAAG GGGAGGGTTG G                                             21

(2) INFORMATION FOR SEQ ID NO: 130:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO: 130:

GGGGAGACCG AAACCGCAAA                                               20

(2) INFORMATION FOR SEQ ID NO: 131:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO: 131:

CCTGGATGAT GCTGGGGTAC                                               20

(2) INFORMATION FOR SEQ ID NO: 132:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO: 132:

GACTGGGGCG AGGTAGGGGT                                               20

(2) INFORMATION FOR SEQ ID NO: 133:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO: 133:

GTCCCGACTG GGGCGAGGAT                                               20

(2) INFORMATION FOR SEQ ID NO: 134:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 134:

GCCGAGGTCC ATGTCGTACG C                                                      21

(2) INFORMATION FOR SEQ ID NO: 135:

(i) SEQUENCE CHARACTERISTICS:
        (A) LENGTH: 21
        (B) TYPE: nucleic acid
        (C) STRANDEDNESS: single
        (D) TOPOLOGY: linear (ix) FEATURE:
        (A) NAME/KEY: Modified-site
        (B) LOCATION: 18
        (D) OTHER INFORMATION: N is inosine (xi) SEQUENCE DESCRIPTION: SEQ ID NO: 135:

CACGAAAGGC ATGACCGNGG C                                                      21

(2) INFORMATION FOR SEQ ID NO: 136:

(i) SEQUENCE CHARACTERISTICS:
        (A) LENGTH: 21
        (B) TYPE: nucleic acid
        (C) STRANDEDNESS: single
        (D) TOPOLOGY: linear (ix) FEATURE:
        (A) NAME/KEY: Modified-site
        (B) LOCATION: 20
        (D) OTHER INFORMATION: N is inosine (xi) SEQUENCE DESCRIPTION: SEQ ID NO: 136:

CACGAAAGGC ATGACCGGGN C                                                      21

(2) INFORMATION FOR SEQ ID NO: 137:

(i) SEQUENCE CHARACTERISTICS:
        (A) LENGTH: 20
        (B) TYPE: nucleic acid
        (C) STRANDEDNESS: single
        (D) TOPOLOGY: linear (ix) FEATURE:
        (A) NAME/KEY: Modified-site
        (B) LOCATION: 13
        (D) OTHER INFORMATION: N is inosine (ix) FEATURE:
        (A) NAME/KEY: Modified-site
        (B) LOCATION: 19
        (D) OTHER INFORMATION: N is inosine (xi) SEQUENCE DESCRIPTION: SEQ ID NO: 137:

GTTGGAGACC GGNGTTGGNG                                                        20

(2) INFORMATION FOR SEQ ID NO: 138:

(i) SEQUENCE CHARACTERISTICS:
        (A) LENGTH: 20
        (B) TYPE: nucleic acid
        (C) STRANDEDNESS: single
        (D) TOPOLOGY: linear (ix) FEATURE:
        (A) NAME/KEY: Modified-site
        (B) LOCATION: 14
        (D) OTHER INFORMATION: N is inosine (xi) SEQUENCE DESCRIPTION: SEQ ID NO: 138:

GTTGGAGACC GGGNTTGGGG                                                        20

(2) INFORMATION FOR SEQ ID NO: 139:

(i) SEQUENCE CHARACTERISTICS:
        (A) LENGTH: 20
        (B) TYPE: nucleic acid
        (C) STRANDEDNESS: single
        (D) TOPOLOGY: linear (ix) FEATURE:
        (A) NAME/KEY: Modified-site
        (B) LOCATION: 19
        (D) OTHER INFORMATION: N is inosine (xi) SEQUENCE DESCRIPTION: SEQ ID NO: 139:

GTTGGAGACC GGGTTTGGNG                                                          20

(2) INFORMATION FOR SEQ ID NO: 140:

(i) SEQUENCE CHARACTERISTICS:
        (A) LENGTH: 20
        (B) TYPE: nucleic acid
        (C) STRANDEDNESS: single
        (D) TOPOLOGY: linear (ix) FEATURE:
        (A) NAME/KEY: Modified-site
        (B) LOCATION: 12
        (D) OTHER INFORMATION: N is inosine (xi) SEQUENCE DESCRIPTION: SEQ ID NO: 140:

GTTGGAGACC GNGGTTGGGG                                                          20

(2) INFORMATION FOR SEQ ID NO: 141:

(i) SEQUENCE CHARACTERISTICS:
        (A) LENGTH: 20
        (B) TYPE: nucleic acid
        (C) STRANDEDNESS: single
        (D) TOPOLOGY: linear (ix) FEATURE:
        (A) NAME/KEY: Modified-site
        (B) LOCATION: 20
        (D) OTHER INFORMATION: N is inosine (xi) SEQUENCE DESCRIPTION: SEQ ID NO: 141:

GTTGGAGACC GGGGTTGGGN                                                          20

(2) INFORMATION FOR SEQ ID NO: 142:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 142:

TTTTTTTTTT TTTGGGGTTT T                                                        21

(2) INFORMATION FOR SEQ ID NO: 143:

(i) SEQUENCE CHARACTERISTICS:
        (A) LENGTH: 12
        (B) TYPE: nucleic acid
        (C) STRANDEDNESS: single
        (D) TOPOLOGY: linear (xi) SEQUENCE DESCRIPTION: SEQ ID NO: 143:

GGGGTTTTGG GG                                                                   12

(2) INFORMATION FOR SEQ ID NO: 144:

(i) SEQUENCE CHARACTERISTICS:
        (A) LENGTH: 10
        (B) TYPE: nucleic acid
        (C) STRANDEDNESS: single
        (D) TOPOLOGY: linear (xi) SEQUENCE DESCRIPTION: SEQ ID NO: 144:

GGGTTTTGGG                                              10

(2) INFORMATION FOR SEQ ID NO: 145:

(i) SEQUENCE CHARACTERISTICS:
        (A) LENGTH: 10
        (B) TYPE: nucleic acid
        (C) STRANDEDNESS: single
        (D) TOPOLOGY: linear (xi) SEQUENCE DESCRIPTION: SEQ ID NO: 145:

GGGGGTTTTT                                              10

(2) INFORMATION FOR SEQ ID NO: 146:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 146:

TTTTTTTTTT TTTGGGGGGG G                                21